US011278571B2

(12) United States Patent
Schuster et al.

(10) Patent No.: US 11,278,571 B2
(45) Date of Patent: Mar. 22, 2022

(54) PEPTIDES AND COMBINATION OF PEPTIDES FOR USE IN IMMUNOTHERAPY AGAINST EPITHELIAL OVARIAN CANCER AND OTHER CANCERS

(71) Applicant: Immatics Biotechnologies GmbH, Tuebingen (DE)

(72) Inventors: Heiko Schuster, Tuebingen (DE); Janet Peper, Tuebingen (DE); Philipp Wagner, Stuttgart (DE); Hans-Georg Rammensee, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 17/245,076

(22) Filed: Apr. 30, 2021

(65) Prior Publication Data

US 2021/0252065 A1   Aug. 19, 2021

Related U.S. Application Data

(63) Continuation of application No. 17/123,585, filed on Dec. 16, 2020, which is a continuation of application No. 16/905,550, filed on Jun. 18, 2020, now Pat. No. 10,888,587, which is a continuation of application No. 16/777,919, filed on Jan. 31, 2020, now Pat. No. 10,722,538, which is a continuation of application No. 16/556,549, filed on Aug. 30, 2019, now Pat. No. 10,639,331, which is a continuation of application No. 15/813,610, filed on Nov. 15, 2017, now Pat. No. 10,463,696, which is a continuation of application No. 15/209,845, filed on Jul. 14, 2016, now Pat. No. 9,889,159.

(60) Provisional application No. 62/192,670, filed on Jul. 15, 2015.

(30) Foreign Application Priority Data

Jul. 15, 2015  (GB) .................................. 1512369

(51) Int. Cl.
| | |
|---|---|
| A61K 39/00 | (2006.01) |
| A61K 35/17 | (2015.01) |
| C07K 14/47 | (2006.01) |
| C07K 7/06 | (2006.01) |
| C07K 7/08 | (2006.01) |
| C07K 14/725 | (2006.01) |
| C07K 16/30 | (2006.01) |
| C12N 15/115 | (2010.01) |
| C12P 21/02 | (2006.01) |
| C12Q 1/6881 | (2018.01) |
| C12Q 1/6886 | (2018.01) |
| G01N 33/574 | (2006.01) |

(52) U.S. Cl.
CPC .......... *A61K 35/17* (2013.01); *A61K 39/0011* (2013.01); *C07K 7/06* (2013.01); *C07K 7/08* (2013.01); *C07K 14/4727* (2013.01); *C07K 14/4748* (2013.01); *C07K 14/7051* (2013.01); *C07K 16/30* (2013.01); *C12N 15/115* (2013.01); *C12P 21/02* (2013.01); *C12Q 1/6881* (2013.01); *C12Q 1/6886* (2013.01); *G01N 33/57484* (2013.01); *A61K 2039/5158* (2013.01); *C12N 2310/16* (2013.01); *C12Q 2600/136* (2013.01); *C12Q 2600/156* (2013.01); *C12Q 2600/158* (2013.01); *G01N 2333/70539* (2013.01); *G01N 2500/04* (2013.01)

(58) Field of Classification Search
CPC ...... A61K 35/17; A61K 39/0011; C07K 7/06; C07K 7/08; C07K 14/4748; C07K 16/30; C12Q 1/6886
See application file for complete search history.

(56) References Cited

U.S. PATENT DOCUMENTS

| | | | | |
|---|---|---|---|---|
| 9,802,997 | B2 * | 10/2017 | Mahr | ..................... C07K 16/18 |
| 9,840,548 | B2 * | 12/2017 | Mahr | ................. G01N 33/5088 |
| 9,932,384 | B2 * | 4/2018 | Mahr | ....................... C07K 7/06 |
| 9,951,119 | B2 * | 4/2018 | Mahr | ..................... A61P 35/02 |
| 9,982,030 | B2 * | 5/2018 | Mahr | ..................... A01N 37/46 |
| 9,982,031 | B2 * | 5/2018 | Mahr | ..................... A61K 38/08 |
| 9,988,432 | B2 * | 6/2018 | Mahr | ..................... A61P 35/02 |

(Continued)

FOREIGN PATENT DOCUMENTS

| | | |
|---|---|---|
| WO | 2007/028573 A1 | 3/2007 |
| WO | 2014/011465 A2 | 1/2014 |

OTHER PUBLICATIONS

Combined Search and Exam Report dated May 27, 2016, in counterpart Application No. GB 1512369.8.

(Continued)

*Primary Examiner* — Sheela J. Huff
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 8 Drawing Sheets

Specification includes a Sequence Listing.

(56) References Cited

U.S. PATENT DOCUMENTS

| | | | | |
|---|---|---|---|---|
| 9,994,628 B2 * | 6/2018 | Mahr | ................ | A61K 39/0005 |
| 10,000,547 B2 * | 6/2018 | Mahr | ................ | C12N 9/6491 |
| 10,005,828 B2 * | 6/2018 | Mahr | ................ | A61K 39/0005 |
| 10,059,755 B2 * | 8/2018 | Mahr | ................ | C07K 14/4702 |
| 10,066,003 B1 * | 9/2018 | Mahr | ................ | A61K 38/06 |
| 10,072,063 B2 * | 9/2018 | Mahr | ................ | A61P 35/02 |
| 10,081,664 B2 * | 9/2018 | Mahr | ................ | C07K 16/30 |
| 10,081,665 B2 * | 9/2018 | Mahr | ................ | A61K 39/0011 |
| 10,106,593 B2 * | 10/2018 | Mahr | ................ | A61K 45/06 |
| 10,106,594 B2 * | 10/2018 | Mahr | ................ | C07K 14/70539 |
| 10,131,703 B2 * | 11/2018 | Mahr | ................ | A01N 37/46 |
| 10,138,288 B2 * | 11/2018 | Mahr | ................ | A61K 39/0005 |
| 10,155,801 B1 * | 12/2018 | Mahr | ................ | C07K 14/70539 |
| 10,183,982 B2 * | 1/2019 | Mahr | ................ | A61P 35/02 |
| 10,202,436 B2 * | 2/2019 | Mahr | ................ | C12N 5/0638 |
| 10,336,809 B2 * | 7/2019 | Mahr | ................ | G01N 33/566 |
| 10,370,429 B2 * | 8/2019 | Mahr | ................ | C07K 14/47 |
| 10,450,362 B2 * | 10/2019 | Mahr | ................ | A61P 35/02 |
| 10,479,823 B2 * | 11/2019 | Mahr | ................ | A61P 35/02 |
| 10,487,131 B2 * | 11/2019 | Mahr | ................ | C07K 16/2833 |
| 10,501,522 B2 * | 12/2019 | Mahr | ................ | C07K 14/001 |
| 10,519,215 B2 * | 12/2019 | Mahr | ................ | A01N 37/46 |
| 10,723,781 B2 * | 7/2020 | Mahr | ................ | C07K 7/02 |
| 10,745,460 B2 * | 8/2020 | Mahr | ................ | A61K 39/001102 |
| 10,766,944 B2 * | 9/2020 | Mahr | ................ | A61K 38/06 |
| 10,934,338 B2 * | 3/2021 | Mahr | ................ | A61K 38/06 |
| 10,947,293 B2 * | 3/2021 | Mahr | ................ | A61K 38/1774 |
| 10,947,294 B2 * | 3/2021 | Mahr | ................ | A61K 38/1774 |
| 2008/0085266 A1 | 4/2008 | Santin et al. | | |
| 2009/0274714 A1 | 11/2009 | Singh et al. | | |
| 2011/0229481 A1 | 9/2011 | Okubo et al. | | |
| 2016/0279215 A1 * | 9/2016 | Mahr | ................ | A01N 37/46 |
| 2016/0279216 A1 * | 9/2016 | Mahr | ................ | C07K 16/2833 |
| 2016/0279218 A1 * | 9/2016 | Mahr | ................ | A01N 37/46 |
| 2017/0305992 A1 * | 10/2017 | Mahr | ................ | A01N 37/46 |
| 2018/0037628 A1 * | 2/2018 | Mahr | ................ | C07K 16/2833 |
| 2018/0251517 A1 * | 9/2018 | Mahr | ................ | G01N 33/505 |
| 2018/0327475 A1 * | 11/2018 | Mahr | ................ | A61K 39/0005 |
| 2019/0119352 A1 * | 4/2019 | Mahr | ................ | A61P 35/00 |
| 2019/0185540 A1 * | 6/2019 | Mahr | ................ | G01N 33/56977 |
| 2020/0024325 A1 * | 1/2020 | Mahr | ................ | C12N 5/0636 |
| 2020/0040060 A1 * | 2/2020 | Mahr | ................ | G01N 33/56977 |
| 2020/0087378 A1 * | 3/2020 | Mahr | ................ | A61K 38/08 |
| 2021/0179691 A1 * | 6/2021 | Mahr | ................ | C07K 14/47 |
| 2021/0188943 A1 * | 6/2021 | Mahr | ................ | A61P 39/00 |
| 2021/0188944 A1 * | 6/2021 | Mahr | ................ | C07K 14/4748 |

OTHER PUBLICATIONS

Bellone et al., "Generation of CA125 specific cytotoxic t lymphocytes . . . " American Journal of Obstetrics and Gynecology. (2009) 75.E1-75.E10.

Michal Bassani-Sternberg et al., "Mass spectrometry of human leukocyte antigen class I peptidomes reveals strong effects of protein abundance and turnover on antigen presentation," Molecular & Cellular Proteomics, vol. 14, No. 3, Mar. 2, 2015, pp. 658-673. XP055272560. ISSN: 1535-9476. DOI: 10.1074/mcp.M114. 042812.

International Search Report issued in counterpart application No. PCT/EP2016/066706, dated Dec. 22, 2016.

* cited by examiner

SEQUENCE LISTING

```
<160> NUMBER OF SEQ ID NOS: 559

<210> SEQ ID NO 1
<211> LENGTH: 9
<212> TYPE: PRT
<213> ORGANISM: Homo sapiens

<400> SEQUENCE: 1

Gln Phe Ile Thr Ser Thr Asn Thr Phe
1               5

<210> SEQ ID NO 2
<211> LENGTH: 9
<212> TYPE: PRT
<213> ORGANISM: Homo sapiens

<400> SEQUENCE: 2

Ser Thr Glu Thr Ser Thr Val Leu Tyr
1               5

<210> SEQ ID NO 3
<211> LENGTH: 9
<212> TYPE: PRT
<213> ORGANISM: Homo sapiens

<400> SEQUENCE: 3

Ala His Ser Lys Ile Thr Thr Ala Met
1               5
```

```
<210> SEQ ID NO 4
<211> LENGTH: 11
<212> TYPE: PRT
<213> ORGANISM: Homo sapiens

<400> SEQUENCE: 4

Ala Val Lys Thr Glu Thr Ser Thr Ser Glu Arg
1               5                   10

<210> SEQ ID NO 5
<211> LENGTH: 9
<212> TYPE: PRT
<213> ORGANISM: Homo sapiens

<400> SEQUENCE: 5

Ala Val Thr Asn Val Arg Thr Ser Ile
1               5

<210> SEQ ID NO 6
<211> LENGTH: 9
<212> TYPE: PRT
<213> ORGANISM: Homo sapiens

<400> SEQUENCE: 6

Asp Ala Leu Thr Pro Leu Val Thr Ile
1               5

<210> SEQ ID NO 7
<211> LENGTH: 8
<212> TYPE: PRT
<213> ORGANISM: Homo sapiens

<400> SEQUENCE: 7

Asp Ala Leu Val Leu Lys Thr Val
1               5

<210> SEQ ID NO 8
<211> LENGTH: 9
<212> TYPE: PRT
<213> ORGANISM: Homo sapiens

<400> SEQUENCE: 8

Asp Pro Tyr Lys Ala Thr Ser Ala Val
1               5

<210> SEQ ID NO 9
<211> LENGTH: 11
<212> TYPE: PRT
<213> ORGANISM: Homo sapiens

<400> SEQUENCE: 9

Glu Pro Glu Thr Thr Thr Ser Phe Ile Thr Tyr
1               5                   10

<210> SEQ ID NO 10
<211> LENGTH: 9
<212> TYPE: PRT
<213> ORGANISM: Homo sapiens

<400> SEQUENCE: 10

Glu Arg Ser Pro Val Ile Gln Thr Leu
1               5

<210> SEQ ID NO 11
```

```
<211> LENGTH: 9
<212> TYPE: PRT
<213> ORGANISM: Homo sapiens

<400> SEQUENCE: 11

Glu Thr Ile Leu Thr Phe His Ala Phe
1               5

<210> SEQ ID NO 12
<211> LENGTH: 10
<212> TYPE: PRT
<213> ORGANISM: Homo sapiens

<400> SEQUENCE: 12

Glu Val Ile Ser Ser Arg Gly Thr Ser Met
1               5                   10

<210> SEQ ID NO 13
<211> LENGTH: 10
<212> TYPE: PRT
<213> ORGANISM: Homo sapiens

<400> SEQUENCE: 13

Glu Val Ile Thr Ser Ser Arg Thr Thr Ile
1               5                   10

<210> SEQ ID NO 14
<211> LENGTH: 10
<212> TYPE: PRT
<213> ORGANISM: Homo sapiens

<400> SEQUENCE: 14

Glu Val Thr Ser Ser Gly Arg Thr Ser Ile
1               5                   10

<210> SEQ ID NO 15
<211> LENGTH: 9
<212> TYPE: PRT
<213> ORGANISM: Homo sapiens

<400> SEQUENCE: 15

Phe Pro Glu Lys Thr Thr His Ser Phe
1               5

<210> SEQ ID NO 16
<211> LENGTH: 10
<212> TYPE: PRT
<213> ORGANISM: Homo sapiens

<400> SEQUENCE: 16

Phe Pro His Ser Glu Glu Thr Thr Thr Met
1               5                   10

<210> SEQ ID NO 17
<211> LENGTH: 9
<212> TYPE: PRT
<213> ORGANISM: Homo sapiens

<400> SEQUENCE: 17

Phe Pro His Ser Glu Ile Thr Thr Leu
1               5

<210> SEQ ID NO 18
<211> LENGTH: 9
<212> TYPE: PRT
```

```
<213> ORGANISM: Homo sapiens

<400> SEQUENCE: 18

Phe Gln Arg Gln Gly Gln Thr Ala Leu
1               5

<210> SEQ ID NO 19
<211> LENGTH: 9
<212> TYPE: PRT
<213> ORGANISM: Homo sapiens

<400> SEQUENCE: 19

Gly Asp Val Pro Arg Pro Ser Ser Leu
1               5

<210> SEQ ID NO 20
<211> LENGTH: 9
<212> TYPE: PRT
<213> ORGANISM: Homo sapiens

<400> SEQUENCE: 20

Gly His Glu Ser His Ser Pro Ala Leu
1               5

<210> SEQ ID NO 21
<211> LENGTH: 9
<212> TYPE: PRT
<213> ORGANISM: Homo sapiens

<400> SEQUENCE: 21

Gly His Thr Thr Val Ser Thr Ser Met
1               5

<210> SEQ ID NO 22
<211> LENGTH: 9
<212> TYPE: PRT
<213> ORGANISM: Homo sapiens

<400> SEQUENCE: 22

Gly Thr His Ser Pro Val Thr Gln Arg
1               5

<210> SEQ ID NO 23
<211> LENGTH: 9
<212> TYPE: PRT
<213> ORGANISM: Homo sapiens

<400> SEQUENCE: 23

Gly Thr Ser Gly Thr Pro Val Ser Lys
1               5

<210> SEQ ID NO 24
<211> LENGTH: 9
<212> TYPE: PRT
<213> ORGANISM: Homo sapiens

<400> SEQUENCE: 24

His Pro Asp Pro Gln Ser Pro Gly Leu
1               5

<210> SEQ ID NO 25
<211> LENGTH: 9
<212> TYPE: PRT
<213> ORGANISM: Homo sapiens
```

```
<400> SEQUENCE: 25

Ile Pro Arg Val Phe Thr Ser Ser Ile
1               5

<210> SEQ ID NO 26
<211> LENGTH: 9
<212> TYPE: PRT
<213> ORGANISM: Homo sapiens

<400> SEQUENCE: 26

Ile Ser Asp Glu Val Val Thr Arg Leu
1               5

<210> SEQ ID NO 27
<211> LENGTH: 9
<212> TYPE: PRT
<213> ORGANISM: Homo sapiens

<400> SEQUENCE: 27

Ile Ser Ile Gly Thr Ile Pro Arg Ile
1               5

<210> SEQ ID NO 28
<211> LENGTH: 9
<212> TYPE: PRT
<213> ORGANISM: Homo sapiens

<400> SEQUENCE: 28

Ile Ser Lys Glu Asp Val Thr Ser Ile
1               5

<210> SEQ ID NO 29
<211> LENGTH: 9
<212> TYPE: PRT
<213> ORGANISM: Homo sapiens

<400> SEQUENCE: 29

Ile Thr Glu Thr Ser Ala Val Leu Tyr
1               5

<210> SEQ ID NO 30
<211> LENGTH: 9
<212> TYPE: PRT
<213> ORGANISM: Homo sapiens

<400> SEQUENCE: 30

Ile Thr Arg Leu Pro Thr Ser Ser Ile
1               5

<210> SEQ ID NO 31
<211> LENGTH: 9
<212> TYPE: PRT
<213> ORGANISM: Homo sapiens

<400> SEQUENCE: 31

Lys Asp Thr Ala His Thr Glu Ala Met
1               5

<210> SEQ ID NO 32
<211> LENGTH: 9
<212> TYPE: PRT
<213> ORGANISM: Homo sapiens

<400> SEQUENCE: 32
```

Lys Glu Asp Ser Thr Ala Leu Val Met
1               5

<210> SEQ ID NO 33
<211> LENGTH: 10
<212> TYPE: PRT
<213> ORGANISM: Homo sapiens

<400> SEQUENCE: 33

Lys Glu Val Thr Ser Ser Ser Val Leu
1               5                   10

<210> SEQ ID NO 34
<211> LENGTH: 9
<212> TYPE: PRT
<213> ORGANISM: Homo sapiens

<400> SEQUENCE: 34

Leu Pro His Ser Glu Ile Thr Thr Leu
1               5

<210> SEQ ID NO 35
<211> LENGTH: 9
<212> TYPE: PRT
<213> ORGANISM: Homo sapiens

<400> SEQUENCE: 35

Leu Thr Ile Ser Thr His Lys Thr Ile
1               5

<210> SEQ ID NO 36
<211> LENGTH: 9
<212> TYPE: PRT
<213> ORGANISM: Homo sapiens

<400> SEQUENCE: 36

Leu Thr Lys Ser Glu Glu Arg Thr Ile
1               5

<210> SEQ ID NO 37
<211> LENGTH: 9
<212> TYPE: PRT
<213> ORGANISM: Homo sapiens

<400> SEQUENCE: 37

Arg Asp Ser Leu Tyr Val Asn Gly Phe
1               5

<210> SEQ ID NO 38
<211> LENGTH: 9
<212> TYPE: PRT
<213> ORGANISM: Homo sapiens

<400> SEQUENCE: 38

Arg Glu Thr Ser Thr Ser Gln Lys Ile
1               5

<210> SEQ ID NO 39
<211> LENGTH: 9
<212> TYPE: PRT
<213> ORGANISM: Homo sapiens

<400> SEQUENCE: 39

Arg Ser Ser Gly Val Thr Phe Ser Arg
1               5

<210> SEQ ID NO 40
<211> LENGTH: 9
<212> TYPE: PRT
<213> ORGANISM: Homo sapiens

<400> SEQUENCE: 40

Ser Ala Phe Glu Ser His Ser Thr Val
1               5

<210> SEQ ID NO 41
<211> LENGTH: 9
<212> TYPE: PRT
<213> ORGANISM: Homo sapiens

<400> SEQUENCE: 41

Ser Ala Thr Glu Arg Ser Ala Ser Leu
1               5

<210> SEQ ID NO 42
<211> LENGTH: 9
<212> TYPE: PRT
<213> ORGANISM: Homo sapiens

<400> SEQUENCE: 42

Ser Glu Asn Ser Glu Thr Thr Ala Leu
1               5

<210> SEQ ID NO 43
<211> LENGTH: 9
<212> TYPE: PRT
<213> ORGANISM: Homo sapiens

<400> SEQUENCE: 43

Ser Glu Gln Arg Thr Ser Pro Ser Leu
1               5

<210> SEQ ID NO 44
<211> LENGTH: 9
<212> TYPE: PRT
<213> ORGANISM: Homo sapiens

<400> SEQUENCE: 44

Ser Glu Ser Pro Ser Thr Ile Lys Leu
1               5

<210> SEQ ID NO 45
<211> LENGTH: 9
<212> TYPE: PRT
<213> ORGANISM: Homo sapiens

<400> SEQUENCE: 45

Ser Pro Ala Gly Glu Ala His Ser Leu
1               5

<210> SEQ ID NO 46
<211> LENGTH: 11
<212> TYPE: PRT
<213> ORGANISM: Homo sapiens

<400> SEQUENCE: 46

Ser Pro Ala Gly Glu Ala His Ser Leu Leu Ala
1               5                   10

<210> SEQ ID NO 47
<211> LENGTH: 9
<212> TYPE: PRT
<213> ORGANISM: Homo sapiens

<400> SEQUENCE: 47

Ser Pro His Pro Val Ser Thr Thr Phe
1               5

<210> SEQ ID NO 48
<211> LENGTH: 9
<212> TYPE: PRT
<213> ORGANISM: Homo sapiens

<400> SEQUENCE: 48

Ser Pro His Pro Val Thr Ala Leu Leu
1               5

<210> SEQ ID NO 49
<211> LENGTH: 9
<212> TYPE: PRT
<213> ORGANISM: Homo sapiens

<400> SEQUENCE: 49

Ser Pro Leu Phe Gln Arg Ser Ser Leu
1               5

<210> SEQ ID NO 50
<211> LENGTH: 9
<212> TYPE: PRT
<213> ORGANISM: Homo sapiens

<400> SEQUENCE: 50

Ser Pro Gln Asn Leu Arg Asn Thr Leu
1               5

<210> SEQ ID NO 51
<211> LENGTH: 12
<212> TYPE: PRT
<213> ORGANISM: Homo sapiens

<400> SEQUENCE: 51

Ser Pro Arg Leu Asn Thr Gln Gly Asn Thr Ala Leu
1               5                   10

<210> SEQ ID NO 52
<211> LENGTH: 9
<212> TYPE: PRT
<213> ORGANISM: Homo sapiens

<400> SEQUENCE: 52

Ser Pro Ser Glu Ala Ile Thr Arg Leu
1               5

<210> SEQ ID NO 53
<211> LENGTH: 9
<212> TYPE: PRT
<213> ORGANISM: Homo sapiens

<400> SEQUENCE: 53

Ser Pro Ser Lys Ala Phe Ala Ser Leu
1               5

<210> SEQ ID NO 54
<211> LENGTH: 9

```
<212> TYPE: PRT
<213> ORGANISM: Homo sapiens

<400> SEQUENCE: 54

Ser Pro Ser Ser Pro Thr Pro Lys Val
1               5

<210> SEQ ID NO 55
<211> LENGTH: 9
<212> TYPE: PRT
<213> ORGANISM: Homo sapiens

<400> SEQUENCE: 55

Ser Pro Ser Ser Gln Ala Pro Val Leu
1               5

<210> SEQ ID NO 56
<211> LENGTH: 9
<212> TYPE: PRT
<213> ORGANISM: Homo sapiens

<400> SEQUENCE: 56

Ser Gln Gly Phe Ser His Ser Gln Met
1               5

<210> SEQ ID NO 57
<211> LENGTH: 9
<212> TYPE: PRT
<213> ORGANISM: Homo sapiens

<400> SEQUENCE: 57

Ser Arg Thr Glu Val Ile Ser Ser Arg
1               5

<210> SEQ ID NO 58
<211> LENGTH: 9
<212> TYPE: PRT
<213> ORGANISM: Homo sapiens

<400> SEQUENCE: 58

Ser Ser Ala Val Ser Thr Thr Thr Ile
1               5

<210> SEQ ID NO 59
<211> LENGTH: 9
<212> TYPE: PRT
<213> ORGANISM: Homo sapiens

<400> SEQUENCE: 59

Ser Ser Pro Leu Arg Val Thr Ser Leu
1               5

<210> SEQ ID NO 60
<211> LENGTH: 9
<212> TYPE: PRT
<213> ORGANISM: Homo sapiens

<400> SEQUENCE: 60

Ser Thr Ala Ser Ser Ser Leu Ser Lys
1               5

<210> SEQ ID NO 61
<211> LENGTH: 9
<212> TYPE: PRT
<213> ORGANISM: Homo sapiens
```

<400> SEQUENCE: 61

Ser Thr Gln Arg Val Thr Thr Ser Met
1               5

<210> SEQ ID NO 62
<211> LENGTH: 11
<212> TYPE: PRT
<213> ORGANISM: Homo sapiens

<400> SEQUENCE: 62

Ser Thr Ser Gln Glu Ile His Ser Ala Thr Lys
1               5                   10

<210> SEQ ID NO 63
<211> LENGTH: 10
<212> TYPE: PRT
<213> ORGANISM: Homo sapiens

<400> SEQUENCE: 63

Ser Val Leu Ala Asp Leu Val Thr Thr Lys
1               5                   10

<210> SEQ ID NO 64
<211> LENGTH: 10
<212> TYPE: PRT
<213> ORGANISM: Homo sapiens

<400> SEQUENCE: 64

Ser Val Pro Asp Ile Leu Ser Thr Ser Trp
1               5                   10

<210> SEQ ID NO 65
<211> LENGTH: 9
<212> TYPE: PRT
<213> ORGANISM: Homo sapiens

<400> SEQUENCE: 65

Thr Ala Gly Pro Thr Thr His Gln Phe
1               5

<210> SEQ ID NO 66
<211> LENGTH: 10
<212> TYPE: PRT
<213> ORGANISM: Homo sapiens

<400> SEQUENCE: 66

Thr Glu Ile Ser Ser Ser Arg Thr Ser Ile
1               5                   10

<210> SEQ ID NO 67
<211> LENGTH: 9
<212> TYPE: PRT
<213> ORGANISM: Homo sapiens

<400> SEQUENCE: 67

Thr Glu Asn Thr Gly Lys Glu Lys Leu
1               5

<210> SEQ ID NO 68
<211> LENGTH: 9
<212> TYPE: PRT
<213> ORGANISM: Homo sapiens

<400> SEQUENCE: 68

```
Thr Glu Thr Glu Ala Ile His Val Phe
1               5

<210> SEQ ID NO 69
<211> LENGTH: 9
<212> TYPE: PRT
<213> ORGANISM: Homo sapiens

<400> SEQUENCE: 69

Thr Glu Val Ser Arg Thr Glu Val Ile
1               5

<210> SEQ ID NO 70
<211> LENGTH: 9
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be Ser, Arg or Gly

<400> SEQUENCE: 70

Thr Glu Xaa Val Leu Gln Gly Leu Leu
1               5

<210> SEQ ID NO 71
<211> LENGTH: 9
<212> TYPE: PRT
<213> ORGANISM: Homo sapiens

<400> SEQUENCE: 71

Thr Pro Gly Gly Thr Arg Gln Ser Leu
1               5

<210> SEQ ID NO 72
<211> LENGTH: 9
<212> TYPE: PRT
<213> ORGANISM: Homo sapiens

<400> SEQUENCE: 72

Thr Pro Gly Asn Arg Ala Ile Ser Leu
1               5

<210> SEQ ID NO 73
<211> LENGTH: 10
<212> TYPE: PRT
<213> ORGANISM: Homo sapiens

<400> SEQUENCE: 73

Thr Pro Asn Ser Arg Gly Glu Thr Ser Leu
1               5                   10

<210> SEQ ID NO 74
<211> LENGTH: 9
<212> TYPE: PRT
<213> ORGANISM: Homo sapiens

<400> SEQUENCE: 74

Thr Ser Gly Pro Val Thr Glu Lys Tyr
1               5

<210> SEQ ID NO 75
<211> LENGTH: 10
<212> TYPE: PRT
<213> ORGANISM: Homo sapiens
```

<400> SEQUENCE: 75

Thr Ser Pro Ala Gly Glu Ala His Ser Leu
1               5                   10

<210> SEQ ID NO 76
<211> LENGTH: 9
<212> TYPE: PRT
<213> ORGANISM: Homo sapiens

<400> SEQUENCE: 76

Val His Glu Ser His Ser Ser Val Leu
1               5

<210> SEQ ID NO 77
<211> LENGTH: 9
<212> TYPE: PRT
<213> ORGANISM: Homo sapiens

<400> SEQUENCE: 77

Val Pro Arg Ser Ala Ala Thr Thr Leu
1               5

<210> SEQ ID NO 78
<211> LENGTH: 9
<212> TYPE: PRT
<213> ORGANISM: Homo sapiens

<400> SEQUENCE: 78

Val Thr Ser Ala Pro Gly Arg Ser Ile
1               5

<210> SEQ ID NO 79
<211> LENGTH: 9
<212> TYPE: PRT
<213> ORGANISM: Homo sapiens

<400> SEQUENCE: 79

Val Thr Ser Ser Ser Arg Thr Ser Ile
1               5

<210> SEQ ID NO 80
<211> LENGTH: 11
<212> TYPE: PRT
<213> ORGANISM: Homo sapiens

<400> SEQUENCE: 80

Tyr Pro Asp Pro Ser Lys Ala Ser Ser Ala Met
1               5                   10

<210> SEQ ID NO 81
<211> LENGTH: 9
<212> TYPE: PRT
<213> ORGANISM: Homo sapiens

<400> SEQUENCE: 81

Ala Ala Trp Leu Arg Ser Ala Ala Ala
1               5

<210> SEQ ID NO 82
<211> LENGTH: 10
<212> TYPE: PRT
<213> ORGANISM: Homo sapiens

<400> SEQUENCE: 82

Ala Pro Ala Ala Trp Leu Arg Ser Ala Ala
1               5                   10

<210> SEQ ID NO 83
<211> LENGTH: 11
<212> TYPE: PRT
<213> ORGANISM: Homo sapiens

<400> SEQUENCE: 83

Ala Pro Ala Ala Trp Leu Arg Ser Ala Ala Ala
1               5                   10

<210> SEQ ID NO 84
<211> LENGTH: 9
<212> TYPE: PRT
<213> ORGANISM: Homo sapiens

<400> SEQUENCE: 84

Leu Pro Ser Pro Val Asp Ala Ala Phe
1               5

<210> SEQ ID NO 85
<211> LENGTH: 11
<212> TYPE: PRT
<213> ORGANISM: Homo sapiens

<400> SEQUENCE: 85

Arg Gly Val Pro Ser Glu Ile Asp Ala Ala Phe
1               5                   10

<210> SEQ ID NO 86
<211> LENGTH: 9
<212> TYPE: PRT
<213> ORGANISM: Homo sapiens

<400> SEQUENCE: 86

Glu Ala Gly Pro Pro Ala Phe Tyr Arg
1               5

<210> SEQ ID NO 87
<211> LENGTH: 9
<212> TYPE: PRT
<213> ORGANISM: Homo sapiens

<400> SEQUENCE: 87

Ser Thr Ser Ser His Ser Leu Gln Lys
1               5

<210> SEQ ID NO 88
<211> LENGTH: 8
<212> TYPE: PRT
<213> ORGANISM: Homo sapiens

<400> SEQUENCE: 88

Ala Pro His Leu His Leu Ser Ala
1               5

<210> SEQ ID NO 89
<211> LENGTH: 9
<212> TYPE: PRT
<213> ORGANISM: Homo sapiens

<400> SEQUENCE: 89

Ala Pro His Leu His Leu Ser Ala Ala

```
1               5

<210> SEQ ID NO 90
<211> LENGTH: 9
<212> TYPE: PRT
<213> ORGANISM: Homo sapiens

<400> SEQUENCE: 90

Arg Ala Leu Ala Lys Leu Leu Pro Leu
1               5

<210> SEQ ID NO 91
<211> LENGTH: 9
<212> TYPE: PRT
<213> ORGANISM: Homo sapiens

<400> SEQUENCE: 91

Ser Ala Ala Ser Gly Ala Arg Ala Leu
1               5

<210> SEQ ID NO 92
<211> LENGTH: 9
<212> TYPE: PRT
<213> ORGANISM: Homo sapiens

<400> SEQUENCE: 92

Val Leu Val Asp Gln Ser Trp Val Leu
1               5

<210> SEQ ID NO 93
<211> LENGTH: 9
<212> TYPE: PRT
<213> ORGANISM: Homo sapiens

<400> SEQUENCE: 93

Asp Tyr Leu Lys Arg Phe Tyr Leu Tyr
1               5

<210> SEQ ID NO 94
<211> LENGTH: 9
<212> TYPE: PRT
<213> ORGANISM: Homo sapiens

<400> SEQUENCE: 94

Ser Glu Thr Lys Asn Ala Asn Ser Leu
1               5

<210> SEQ ID NO 95
<211> LENGTH: 9
<212> TYPE: PRT
<213> ORGANISM: Homo sapiens

<400> SEQUENCE: 95

Ser Ser Asp Pro Asn Ala Val Met Tyr
1               5

<210> SEQ ID NO 96
<211> LENGTH: 10
<212> TYPE: PRT
<213> ORGANISM: Homo sapiens

<400> SEQUENCE: 96

Tyr Pro Phe Asp Gly Pro Gly Asn Thr Leu
1               5                   10
```

```
<210> SEQ ID NO 97
<211> LENGTH: 12
<212> TYPE: PRT
<213> ORGANISM: Homo sapiens

<400> SEQUENCE: 97

Tyr Pro Phe Asp Gly Pro Gly Asn Thr Leu Ala His
1               5                   10

<210> SEQ ID NO 98
<211> LENGTH: 9
<212> TYPE: PRT
<213> ORGANISM: Homo sapiens

<400> SEQUENCE: 98

Asn Glu Ile Glu Arg Val Phe Val Trp
1               5

<210> SEQ ID NO 99
<211> LENGTH: 10
<212> TYPE: PRT
<213> ORGANISM: Homo sapiens

<400> SEQUENCE: 99

Asn Val Gly Gly Leu Ile Gly Thr Pro Lys
1               5                   10

<210> SEQ ID NO 100
<211> LENGTH: 9
<212> TYPE: PRT
<213> ORGANISM: Homo sapiens

<400> SEQUENCE: 100

Arg Val Lys Glu Met Tyr Asn Thr Tyr
1               5

<210> SEQ ID NO 101
<211> LENGTH: 9
<212> TYPE: PRT
<213> ORGANISM: Homo sapiens

<400> SEQUENCE: 101

Ser Ala Pro Leu Arg Val Ser Gln Leu
1               5

<210> SEQ ID NO 102
<211> LENGTH: 9
<212> TYPE: PRT
<213> ORGANISM: Homo sapiens

<400> SEQUENCE: 102

Asp Thr Asp Glu Tyr Val Leu Lys Tyr
1               5

<210> SEQ ID NO 103
<211> LENGTH: 8
<212> TYPE: PRT
<213> ORGANISM: Homo sapiens

<400> SEQUENCE: 103

Lys Asp Ser Thr Lys Thr Ala Phe
1               5

<210> SEQ ID NO 104
```

```
<211> LENGTH: 8
<212> TYPE: PRT
<213> ORGANISM: Homo sapiens

<400> SEQUENCE: 104

Ser Lys Ala Pro Val Leu Thr Tyr
1               5

<210> SEQ ID NO 105
<211> LENGTH: 10
<212> TYPE: PRT
<213> ORGANISM: Homo sapiens

<400> SEQUENCE: 105

Ala Glu Tyr Thr Asp Val Leu Gln Lys Ile
1               5                   10

<210> SEQ ID NO 106
<211> LENGTH: 9
<212> TYPE: PRT
<213> ORGANISM: Homo sapiens

<400> SEQUENCE: 106

Glu Tyr Thr Asp Val Leu Gln Lys Ile
1               5

<210> SEQ ID NO 107
<211> LENGTH: 8
<212> TYPE: PRT
<213> ORGANISM: Homo sapiens

<400> SEQUENCE: 107

Arg Pro His Leu Thr Ser Asp Ala
1               5

<210> SEQ ID NO 108
<211> LENGTH: 9
<212> TYPE: PRT
<213> ORGANISM: Homo sapiens

<400> SEQUENCE: 108

Arg Pro His Leu Thr Ser Asp Ala Val
1               5

<210> SEQ ID NO 109
<211> LENGTH: 10
<212> TYPE: PRT
<213> ORGANISM: Homo sapiens

<400> SEQUENCE: 109

Arg Pro His Leu Thr Ser Asp Ala Val Ala
1               5                   10

<210> SEQ ID NO 110
<211> LENGTH: 9
<212> TYPE: PRT
<213> ORGANISM: Homo sapiens

<400> SEQUENCE: 110

Ser Ala Lys Ser Ile Tyr Glu Gln Arg
1               5

<210> SEQ ID NO 111
<211> LENGTH: 9
<212> TYPE: PRT
```

<213> ORGANISM: Homo sapiens

<400> SEQUENCE: 111

Ser Pro Glu Glu Gly Ala Arg Val Tyr
1               5

<210> SEQ ID NO 112
<211> LENGTH: 9
<212> TYPE: PRT
<213> ORGANISM: Homo sapiens

<400> SEQUENCE: 112

Ser Gln Tyr Pro Val Asn His Leu Val
1               5

<210> SEQ ID NO 113
<211> LENGTH: 9
<212> TYPE: PRT
<213> ORGANISM: Homo sapiens

<400> SEQUENCE: 113

Tyr Pro Val Asn His Leu Val Thr Phe
1               5

<210> SEQ ID NO 114
<211> LENGTH: 9
<212> TYPE: PRT
<213> ORGANISM: Homo sapiens

<400> SEQUENCE: 114

Ala Ala Ala Ser Ala Ile Lys Val Ile
1               5

<210> SEQ ID NO 115
<211> LENGTH: 11
<212> TYPE: PRT
<213> ORGANISM: Homo sapiens

<400> SEQUENCE: 115

Ile His Asp His Val Asn Pro Lys Ala Phe Phe
1               5                   10

<210> SEQ ID NO 116
<211> LENGTH: 9
<212> TYPE: PRT
<213> ORGANISM: Homo sapiens

<400> SEQUENCE: 116

Asn Pro Lys Ala Phe Phe Ser Val Leu
1               5

<210> SEQ ID NO 117
<211> LENGTH: 9
<212> TYPE: PRT
<213> ORGANISM: Homo sapiens

<400> SEQUENCE: 117

Asn Pro Ser Val Arg Glu Phe Val Leu
1               5

<210> SEQ ID NO 118
<211> LENGTH: 10
<212> TYPE: PRT
<213> ORGANISM: Homo sapiens

<400> SEQUENCE: 118

Arg Ser Tyr His Leu Gln Ile Val Thr Lys
1               5                   10

<210> SEQ ID NO 119
<211> LENGTH: 10
<212> TYPE: PRT
<213> ORGANISM: Homo sapiens

<400> SEQUENCE: 119

Arg Tyr Met Pro Pro Ala His Arg Asn Phe
1               5                   10

<210> SEQ ID NO 120
<211> LENGTH: 9
<212> TYPE: PRT
<213> ORGANISM: Homo sapiens

<400> SEQUENCE: 120

Thr Glu Phe Glu Gln Tyr Leu His Phe
1               5

<210> SEQ ID NO 121
<211> LENGTH: 10
<212> TYPE: PRT
<213> ORGANISM: Homo sapiens

<400> SEQUENCE: 121

Val Ser Asp Ala Ser Ser Ala Val Tyr Tyr
1               5                   10

<210> SEQ ID NO 122
<211> LENGTH: 9
<212> TYPE: PRT
<213> ORGANISM: Homo sapiens

<400> SEQUENCE: 122

Ala Glu Ile Glu Ala Asp Arg Ser Tyr
1               5

<210> SEQ ID NO 123
<211> LENGTH: 9
<212> TYPE: PRT
<213> ORGANISM: Homo sapiens

<400> SEQUENCE: 123

Ala Gln Lys Val Asp Thr Arg Ala Lys
1               5

<210> SEQ ID NO 124
<211> LENGTH: 9
<212> TYPE: PRT
<213> ORGANISM: Homo sapiens

<400> SEQUENCE: 124

His Pro Ser Ala His Asp Val Ile Leu
1               5

<210> SEQ ID NO 125
<211> LENGTH: 9
<212> TYPE: PRT
<213> ORGANISM: Homo sapiens

<400> SEQUENCE: 125

Arg Ile Lys Gln Lys Ala Asp Ser Leu
1               5

<210> SEQ ID NO 126
<211> LENGTH: 10
<212> TYPE: PRT
<213> ORGANISM: Homo sapiens

<400> SEQUENCE: 126

Ser Glu Gly Ala Ser Arg Ser Leu Gly Leu
1               5                   10

<210> SEQ ID NO 127
<211> LENGTH: 10
<212> TYPE: PRT
<213> ORGANISM: Homo sapiens

<400> SEQUENCE: 127

Ser Val Asp Glu Glu Gly Leu Val Leu Leu
1               5                   10

<210> SEQ ID NO 128
<211> LENGTH: 9
<212> TYPE: PRT
<213> ORGANISM: Homo sapiens

<400> SEQUENCE: 128

Ser Val His Lys Ile Thr Ser Thr Phe
1               5

<210> SEQ ID NO 129
<211> LENGTH: 9
<212> TYPE: PRT
<213> ORGANISM: Homo sapiens

<400> SEQUENCE: 129

Thr Arg Glu Ala Thr Gln Ala Glu Ile
1               5

<210> SEQ ID NO 130
<211> LENGTH: 9
<212> TYPE: PRT
<213> ORGANISM: Homo sapiens

<400> SEQUENCE: 130

Val Tyr Phe Val Ala Pro Ala Lys Phe
1               5

<210> SEQ ID NO 131
<211> LENGTH: 9
<212> TYPE: PRT
<213> ORGANISM: Homo sapiens

<400> SEQUENCE: 131

Ala Pro Gln Ser Ala His Ala Ala Phe
1               5

<210> SEQ ID NO 132
<211> LENGTH: 9
<212> TYPE: PRT
<213> ORGANISM: Homo sapiens

<400> SEQUENCE: 132

Glu Thr Ile Ile Ile Phe His Ser Leu
1               5

<210> SEQ ID NO 133
<211> LENGTH: 8
<212> TYPE: PRT
<213> ORGANISM: Homo sapiens

<400> SEQUENCE: 133

Thr Glu Leu Leu Val Lys Ala Tyr
1               5

<210> SEQ ID NO 134
<211> LENGTH: 11
<212> TYPE: PRT
<213> ORGANISM: Homo sapiens

<400> SEQUENCE: 134

Trp Gln Glu Gly Arg Ala Ser Gly Thr Val Tyr
1               5                   10

<210> SEQ ID NO 135
<211> LENGTH: 9
<212> TYPE: PRT
<213> ORGANISM: Homo sapiens

<400> SEQUENCE: 135

Ile Arg Ser Glu Asn Phe Glu Glu Leu
1               5

<210> SEQ ID NO 136
<211> LENGTH: 9
<212> TYPE: PRT
<213> ORGANISM: Homo sapiens

<400> SEQUENCE: 136

Lys Ile Ala Val Ala Ala Ala Ser Lys
1               5

<210> SEQ ID NO 137
<211> LENGTH: 9
<212> TYPE: PRT
<213> ORGANISM: Homo sapiens

<400> SEQUENCE: 137

Asn Val Met Leu Arg Lys Ile Ala Val
1               5

<210> SEQ ID NO 138
<211> LENGTH: 11
<212> TYPE: PRT
<213> ORGANISM: Homo sapiens

<400> SEQUENCE: 138

Arg Glu Leu Thr Asn Asp Gly Glu Leu Ile Leu
1               5                   10

<210> SEQ ID NO 139
<211> LENGTH: 9
<212> TYPE: PRT
<213> ORGANISM: Homo sapiens

<400> SEQUENCE: 139

Val Ala Ala Ala Ser Lys Pro Ala Val
1               5

```
<210> SEQ ID NO 140
<211> LENGTH: 9
<212> TYPE: PRT
<213> ORGANISM: Homo sapiens

<400> SEQUENCE: 140

Ser Pro Asn Ala Ile Phe Lys Ala Leu
1               5

<210> SEQ ID NO 141
<211> LENGTH: 10
<212> TYPE: PRT
<213> ORGANISM: Homo sapiens

<400> SEQUENCE: 141

Ser Ser Lys Asn Lys Pro His Val Lys Arg
1               5                   10

<210> SEQ ID NO 142
<211> LENGTH: 9
<212> TYPE: PRT
<213> ORGANISM: Homo sapiens

<400> SEQUENCE: 142

Thr Pro Ala Ser Ala Gly His Val Trp
1               5

<210> SEQ ID NO 143
<211> LENGTH: 10
<212> TYPE: PRT
<213> ORGANISM: Homo sapiens

<400> SEQUENCE: 143

Tyr Thr Asp His Gln Asn Ser Ser Ser Tyr
1               5                   10

<210> SEQ ID NO 144
<211> LENGTH: 8
<212> TYPE: PRT
<213> ORGANISM: Homo sapiens

<400> SEQUENCE: 144

Ala Glu Val Leu Leu Pro Arg Leu
1               5

<210> SEQ ID NO 145
<211> LENGTH: 12
<212> TYPE: PRT
<213> ORGANISM: Homo sapiens

<400> SEQUENCE: 145

Ala Val Leu Pro Leu Thr Val Ala Glu Val Gln Lys
1               5                   10

<210> SEQ ID NO 146
<211> LENGTH: 8
<212> TYPE: PRT
<213> ORGANISM: Homo sapiens

<400> SEQUENCE: 146

Leu Pro Thr Ala Arg Pro Leu Leu
1               5

<210> SEQ ID NO 147
<211> LENGTH: 9
```

```
<212> TYPE: PRT
<213> ORGANISM: Homo sapiens

<400> SEQUENCE: 147

Arg Val Arg Glu Leu Ala Val Ala Leu
1               5

<210> SEQ ID NO 148
<211> LENGTH: 9
<212> TYPE: PRT
<213> ORGANISM: Homo sapiens

<400> SEQUENCE: 148

Asn Leu Pro Ile Phe Leu Pro Arg Val
1               5

<210> SEQ ID NO 149
<211> LENGTH: 9
<212> TYPE: PRT
<213> ORGANISM: Homo sapiens

<400> SEQUENCE: 149

Arg Val His Pro Glu Glu Gln Gly Trp
1               5

<210> SEQ ID NO 150
<211> LENGTH: 9
<212> TYPE: PRT
<213> ORGANISM: Homo sapiens

<400> SEQUENCE: 150

Thr Val Lys Pro Ser Gly Lys Pro Arg
1               5

<210> SEQ ID NO 151
<211> LENGTH: 9
<212> TYPE: PRT
<213> ORGANISM: Homo sapiens

<400> SEQUENCE: 151

Tyr Tyr Glu His Val Lys Ala Arg Phe
1               5

<210> SEQ ID NO 152
<211> LENGTH: 9
<212> TYPE: PRT
<213> ORGANISM: Homo sapiens

<400> SEQUENCE: 152

Ala Ala Arg Pro Ala Gly Ala Thr Leu
1               5

<210> SEQ ID NO 153
<211> LENGTH: 10
<212> TYPE: PRT
<213> ORGANISM: Homo sapiens

<400> SEQUENCE: 153

Met Pro Asn Pro Glu Gly Arg Tyr Thr Phe
1               5                   10

<210> SEQ ID NO 154
<211> LENGTH: 9
<212> TYPE: PRT
<213> ORGANISM: Homo sapiens
```

```
<400> SEQUENCE: 154

Phe Tyr Ile Lys Thr Ser Thr Thr Val
1               5

<210> SEQ ID NO 155
<211> LENGTH: 9
<212> TYPE: PRT
<213> ORGANISM: Homo sapiens

<400> SEQUENCE: 155

Arg Thr Thr Glu Ile Asn Phe Lys Val
1               5

<210> SEQ ID NO 156
<211> LENGTH: 8
<212> TYPE: PRT
<213> ORGANISM: Homo sapiens

<400> SEQUENCE: 156

Tyr Ile Lys Thr Ser Thr Thr Val
1               5

<210> SEQ ID NO 157
<211> LENGTH: 9
<212> TYPE: PRT
<213> ORGANISM: Homo sapiens

<400> SEQUENCE: 157

Gly Gln Ala Ala Gln Gly Pro Thr Ile
1               5

<210> SEQ ID NO 158
<211> LENGTH: 9
<212> TYPE: PRT
<213> ORGANISM: Homo sapiens

<400> SEQUENCE: 158

His Arg Phe Leu Ala Glu Asp Ala Leu
1               5

<210> SEQ ID NO 159
<211> LENGTH: 9
<212> TYPE: PRT
<213> ORGANISM: Homo sapiens

<400> SEQUENCE: 159

Glu Glu Val Ala Arg Phe Tyr Ala Ala
1               5

<210> SEQ ID NO 160
<211> LENGTH: 9
<212> TYPE: PRT
<213> ORGANISM: Homo sapiens

<400> SEQUENCE: 160

Asn Pro Asn Glu Glu Val Ala Arg Phe
1               5

<210> SEQ ID NO 161
<211> LENGTH: 10
<212> TYPE: PRT
<213> ORGANISM: Homo sapiens

<400> SEQUENCE: 161
```

Asn Pro Asn Glu Glu Val Ala Arg Phe Tyr
1               5                   10

<210> SEQ ID NO 162
<211> LENGTH: 8
<212> TYPE: PRT
<213> ORGANISM: Homo sapiens

<400> SEQUENCE: 162

Lys Ser Gln Thr Leu Leu Gly Lys
1               5

<210> SEQ ID NO 163
<211> LENGTH: 8
<212> TYPE: PRT
<213> ORGANISM: Homo sapiens

<400> SEQUENCE: 163

Asp Glu Leu Ile Ser Lys Ser Phe
1               5

<210> SEQ ID NO 164
<211> LENGTH: 9
<212> TYPE: PRT
<213> ORGANISM: Homo sapiens

<400> SEQUENCE: 164

His Asp Glu Leu Ile Ser Lys Ser Phe
1               5

<210> SEQ ID NO 165
<211> LENGTH: 9
<212> TYPE: PRT
<213> ORGANISM: Homo sapiens

<400> SEQUENCE: 165

Gly Arg Ala Tyr Leu Phe Asn Ser Val
1               5

<210> SEQ ID NO 166
<211> LENGTH: 9
<212> TYPE: PRT
<213> ORGANISM: Homo sapiens

<400> SEQUENCE: 166

Tyr Leu Phe Asn Ser Val Val Asn Val
1               5

<210> SEQ ID NO 167
<211> LENGTH: 8
<212> TYPE: PRT
<213> ORGANISM: Homo sapiens

<400> SEQUENCE: 167

Ala Pro Asp Asn Arg Pro Ala Leu
1               5

<210> SEQ ID NO 168
<211> LENGTH: 9
<212> TYPE: PRT
<213> ORGANISM: Homo sapiens

<400> SEQUENCE: 168

His His Ser Asp Thr Pro Thr Thr Leu

```
1               5

<210> SEQ ID NO 169
<211> LENGTH: 9
<212> TYPE: PRT
<213> ORGANISM: Homo sapiens

<400> SEQUENCE: 169

His Pro Met Ser Glu Tyr Pro Thr Tyr
1               5

<210> SEQ ID NO 170
<211> LENGTH: 8
<212> TYPE: PRT
<213> ORGANISM: Homo sapiens

<400> SEQUENCE: 170

Leu Gln Arg Asp Ile Ser Glu Met
1               5

<210> SEQ ID NO 171
<211> LENGTH: 9
<212> TYPE: PRT
<213> ORGANISM: Homo sapiens

<400> SEQUENCE: 171

Leu Gln Arg Asp Ile Ser Glu Met Phe
1               5

<210> SEQ ID NO 172
<211> LENGTH: 9
<212> TYPE: PRT
<213> ORGANISM: Homo sapiens

<400> SEQUENCE: 172

Ala Ile Ala Glu Ile Gly Asn Gln Leu
1               5

<210> SEQ ID NO 173
<211> LENGTH: 10
<212> TYPE: PRT
<213> ORGANISM: Homo sapiens

<400> SEQUENCE: 173

Asp Val Ala Gln Val Thr Gly Ala Leu Arg
1               5                   10

<210> SEQ ID NO 174
<211> LENGTH: 9
<212> TYPE: PRT
<213> ORGANISM: Homo sapiens

<400> SEQUENCE: 174

Ser Glu Asp Leu Pro Arg Ala Val Ile
1               5

<210> SEQ ID NO 175
<211> LENGTH: 9
<212> TYPE: PRT
<213> ORGANISM: Homo sapiens

<400> SEQUENCE: 175

Ala Pro Asp Ala Lys Ser Phe Val Leu
1               5
```

<210> SEQ ID NO 176
<211> LENGTH: 9
<212> TYPE: PRT
<213> ORGANISM: Homo sapiens

<400> SEQUENCE: 176

Glu Val Ala Pro Asp Ala Lys Ser Phe
1               5

<210> SEQ ID NO 177
<211> LENGTH: 11
<212> TYPE: PRT
<213> ORGANISM: Homo sapiens

<400> SEQUENCE: 177

Phe Pro Phe Gln Pro Gly Ser Val Ala Glu Val
1               5                   10

<210> SEQ ID NO 178
<211> LENGTH: 12
<212> TYPE: PRT
<213> ORGANISM: Homo sapiens

<400> SEQUENCE: 178

Gly Glu Val Ala Pro Asp Ala Lys Ser Phe Val Leu
1               5                   10

<210> SEQ ID NO 179
<211> LENGTH: 9
<212> TYPE: PRT
<213> ORGANISM: Homo sapiens

<400> SEQUENCE: 179

Leu Pro Asp Gly Tyr Glu Phe Lys Phe
1               5

<210> SEQ ID NO 180
<211> LENGTH: 13
<212> TYPE: PRT
<213> ORGANISM: Homo sapiens

<400> SEQUENCE: 180

Asp Lys Ala Phe Thr Ala Ala Thr Thr Glu Val Ser Arg
1               5                   10

<210> SEQ ID NO 181
<211> LENGTH: 15
<212> TYPE: PRT
<213> ORGANISM: Homo sapiens

<400> SEQUENCE: 181

Glu Leu Gly Pro Tyr Thr Leu Asp Arg Asn Ser Leu Tyr Val Asn
1               5                   10                  15

<210> SEQ ID NO 182
<211> LENGTH: 16
<212> TYPE: PRT
<213> ORGANISM: Homo sapiens

<400> SEQUENCE: 182

Glu Leu Gly Pro Tyr Thr Leu Asp Arg Asn Ser Leu Tyr Val Asn Gly
1               5                   10                  15

<210> SEQ ID NO 183

```
<211> LENGTH: 14
<212> TYPE: PRT
<213> ORGANISM: Homo sapiens

<400> SEQUENCE: 183

Phe Asp Lys Ala Phe Thr Ala Ala Thr Thr Glu Val Ser Arg
1               5                   10

<210> SEQ ID NO 184
<211> LENGTH: 13
<212> TYPE: PRT
<213> ORGANISM: Homo sapiens

<400> SEQUENCE: 184

Gly Pro Tyr Thr Leu Asp Arg Asn Ser Leu Tyr Val Asn
1               5                   10

<210> SEQ ID NO 185
<211> LENGTH: 14
<212> TYPE: PRT
<213> ORGANISM: Homo sapiens

<400> SEQUENCE: 185

Leu Gly Pro Tyr Thr Leu Asp Arg Asp Ser Leu Tyr Val Asn
1               5                   10

<210> SEQ ID NO 186
<211> LENGTH: 14
<212> TYPE: PRT
<213> ORGANISM: Homo sapiens

<400> SEQUENCE: 186

Leu Gly Pro Tyr Thr Leu Asp Arg Asn Ser Leu Tyr Val Asn
1               5                   10

<210> SEQ ID NO 187
<211> LENGTH: 15
<212> TYPE: PRT
<213> ORGANISM: Homo sapiens

<400> SEQUENCE: 187

Leu Gly Pro Tyr Thr Leu Asp Arg Asn Ser Leu Tyr Val Asn Gly
1               5                   10                  15

<210> SEQ ID NO 188
<211> LENGTH: 16
<212> TYPE: PRT
<213> ORGANISM: Homo sapiens

<400> SEQUENCE: 188

Ser Thr Glu Thr Ile Thr Arg Leu Ser Thr Phe Pro Phe Val Thr Gly
1               5                   10                  15

<210> SEQ ID NO 189
<211> LENGTH: 13
<212> TYPE: PRT
<213> ORGANISM: Homo sapiens

<400> SEQUENCE: 189

Glu Leu Gln Trp Glu Gln Ala Gln Asp Tyr Leu Lys Arg
1               5                   10

<210> SEQ ID NO 190
<211> LENGTH: 14
<212> TYPE: PRT
```

<213> ORGANISM: Homo sapiens

<400> SEQUENCE: 190

Glu Leu Gln Trp Glu Gln Ala Gln Asp Tyr Leu Lys Arg Phe
1               5                   10

<210> SEQ ID NO 191
<211> LENGTH: 15
<212> TYPE: PRT
<213> ORGANISM: Homo sapiens

<400> SEQUENCE: 191

Gly Ile Asn Phe Leu Tyr Ala Ala Thr His Glu Leu Gly His Ser
1               5                   10                  15

<210> SEQ ID NO 192
<211> LENGTH: 12
<212> TYPE: PRT
<213> ORGANISM: Homo sapiens

<400> SEQUENCE: 192

Leu Gln Trp Glu Gln Ala Gln Asp Tyr Leu Lys Arg
1               5                   10

<210> SEQ ID NO 193
<211> LENGTH: 13
<212> TYPE: PRT
<213> ORGANISM: Homo sapiens

<400> SEQUENCE: 193

Leu Gln Trp Glu Gln Ala Gln Asp Tyr Leu Lys Arg Phe
1               5                   10

<210> SEQ ID NO 194
<211> LENGTH: 14
<212> TYPE: PRT
<213> ORGANISM: Homo sapiens

<400> SEQUENCE: 194

Ser Glu Leu Gln Trp Glu Gln Ala Gln Asp Tyr Leu Lys Arg
1               5                   10

<210> SEQ ID NO 195
<211> LENGTH: 15
<212> TYPE: PRT
<213> ORGANISM: Homo sapiens

<400> SEQUENCE: 195

Ser Glu Leu Gln Trp Glu Gln Ala Gln Asp Tyr Leu Lys Arg Phe
1               5                   10                  15

<210> SEQ ID NO 196
<211> LENGTH: 13
<212> TYPE: PRT
<213> ORGANISM: Homo sapiens

<400> SEQUENCE: 196

Val Pro Tyr Asn Ile Leu Thr Pro Tyr Pro Gly Pro Arg
1               5                   10

<210> SEQ ID NO 197
<211> LENGTH: 14
<212> TYPE: PRT
<213> ORGANISM: Homo sapiens

```
<400> SEQUENCE: 197

Tyr Val Pro Tyr Asn Ile Leu Thr Pro Tyr Pro Gly Pro Arg
1               5                   10

<210> SEQ ID NO 198
<211> LENGTH: 14
<212> TYPE: PRT
<213> ORGANISM: Homo sapiens

<400> SEQUENCE: 198

Gly Asn Trp Lys Ile Ile Arg Ser Glu Asn Phe Glu Glu Leu
1               5                   10

<210> SEQ ID NO 199
<211> LENGTH: 16
<212> TYPE: PRT
<213> ORGANISM: Homo sapiens

<400> SEQUENCE: 199

Gly Asn Trp Lys Ile Ile Arg Ser Glu Asn Phe Glu Glu Leu Leu Lys
1               5                   10                  15

<210> SEQ ID NO 200
<211> LENGTH: 13
<212> TYPE: PRT
<213> ORGANISM: Homo sapiens

<400> SEQUENCE: 200

Asn Trp Lys Ile Ile Arg Ser Glu Asn Phe Glu Glu Leu
1               5                   10

<210> SEQ ID NO 201
<211> LENGTH: 15
<212> TYPE: PRT
<213> ORGANISM: Homo sapiens

<400> SEQUENCE: 201

Pro Asn Phe Ser Gly Asn Trp Lys Ile Ile Arg Ser Glu Asn Phe
1               5                   10                  15

<210> SEQ ID NO 202
<211> LENGTH: 15
<212> TYPE: PRT
<213> ORGANISM: Homo sapiens

<400> SEQUENCE: 202

Val Met Leu Arg Lys Ile Ala Val Ala Ala Ser Lys Pro Ala
1               5                   10                  15

<210> SEQ ID NO 203
<211> LENGTH: 12
<212> TYPE: PRT
<213> ORGANISM: Homo sapiens

<400> SEQUENCE: 203

Trp Lys Ile Ile Arg Ser Glu Asn Phe Glu Glu Leu
1               5                   10

<210> SEQ ID NO 204
<211> LENGTH: 13
<212> TYPE: PRT
<213> ORGANISM: Homo sapiens

<400> SEQUENCE: 204
```

Leu Gln Arg Tyr Ser Ser Asp Pro Thr Gly Ala Leu Thr
1               5                   10

<210> SEQ ID NO 205
<211> LENGTH: 14
<212> TYPE: PRT
<213> ORGANISM: Homo sapiens

<400> SEQUENCE: 205

Asn Pro Thr Thr Tyr Gln Met Asp Val Asn Pro Glu Gly Lys
1               5                   10

<210> SEQ ID NO 206
<211> LENGTH: 15
<212> TYPE: PRT
<213> ORGANISM: Homo sapiens

<400> SEQUENCE: 206

Asn Pro Thr Thr Tyr Gln Met Asp Val Asn Pro Glu Gly Lys Tyr
1               5                   10                  15

<210> SEQ ID NO 207
<211> LENGTH: 17
<212> TYPE: PRT
<213> ORGANISM: Homo sapiens

<400> SEQUENCE: 207

Asp Asp Gly Gly Gln Phe Val Val Thr Thr Asn Pro Val Asn Asn Asp
1               5                   10                  15
Gly

<210> SEQ ID NO 208
<211> LENGTH: 19
<212> TYPE: PRT
<213> ORGANISM: Homo sapiens

<400> SEQUENCE: 208

Asp Lys Glu Gly Lys Val Phe Tyr Ser Ile Thr Gly Gln Gly Ala Asp
1               5                   10                  15
Thr Pro Pro

<210> SEQ ID NO 209
<211> LENGTH: 20
<212> TYPE: PRT
<213> ORGANISM: Homo sapiens

<400> SEQUENCE: 209

Asp Lys Glu Gly Lys Val Phe Tyr Ser Ile Thr Gly Gln Gly Ala Asp
1               5                   10                  15
Thr Pro Pro Val
            20

<210> SEQ ID NO 210
<211> LENGTH: 14
<212> TYPE: PRT
<213> ORGANISM: Homo sapiens

<400> SEQUENCE: 210

Asp Lys Asn Met Phe Thr Ile Asn Arg Asn Thr Gly Val Ile
1               5                   10

<210> SEQ ID NO 211
<211> LENGTH: 15

```
<212> TYPE: PRT
<213> ORGANISM: Homo sapiens

<400> SEQUENCE: 211

Asp Lys Asn Met Phe Thr Ile Asn Arg Asn Thr Gly Val Ile Ser
1               5                   10                  15

<210> SEQ ID NO 212
<211> LENGTH: 17
<212> TYPE: PRT
<213> ORGANISM: Homo sapiens

<400> SEQUENCE: 212

Asp Pro Glu Leu Pro Asp Lys Asn Met Phe Thr Ile Asn Arg Asn Thr
1               5                   10                  15

Gly

<210> SEQ ID NO 213
<211> LENGTH: 19
<212> TYPE: PRT
<213> ORGANISM: Homo sapiens

<400> SEQUENCE: 213

Asp Pro Glu Leu Pro Asp Lys Asn Met Phe Thr Ile Asn Arg Asn Thr
1               5                   10                  15

Gly Val Ile

<210> SEQ ID NO 214
<211> LENGTH: 20
<212> TYPE: PRT
<213> ORGANISM: Homo sapiens

<400> SEQUENCE: 214

Asp Pro Glu Leu Pro Asp Lys Asn Met Phe Thr Ile Asn Arg Asn Thr
1               5                   10                  15

Gly Val Ile Ser
            20

<210> SEQ ID NO 215
<211> LENGTH: 21
<212> TYPE: PRT
<213> ORGANISM: Homo sapiens

<400> SEQUENCE: 215

Asp Pro Glu Leu Pro Asp Lys Asn Met Phe Thr Ile Asn Arg Asn Thr
1               5                   10                  15

Gly Val Ile Ser Val
            20

<210> SEQ ID NO 216
<211> LENGTH: 22
<212> TYPE: PRT
<213> ORGANISM: Homo sapiens

<400> SEQUENCE: 216

Asp Pro Glu Leu Pro Asp Lys Asn Met Phe Thr Ile Asn Arg Asn Thr
1               5                   10                  15

Gly Val Ile Ser Val Val
            20

<210> SEQ ID NO 217
<211> LENGTH: 23
```

```
<212> TYPE: PRT
<213> ORGANISM: Homo sapiens

<400> SEQUENCE: 217

Asp Pro Glu Leu Pro Asp Lys Asn Met Phe Thr Ile Asn Arg Asn Thr
1               5                   10                  15

Gly Val Ile Ser Val Val Thr
            20

<210> SEQ ID NO 218
<211> LENGTH: 15
<212> TYPE: PRT
<213> ORGANISM: Homo sapiens

<400> SEQUENCE: 218

Asp Val Asn Thr Tyr Asn Ala Ala Ile Ala Tyr Thr Ile Leu Ser
1               5                   10                  15

<210> SEQ ID NO 219
<211> LENGTH: 16
<212> TYPE: PRT
<213> ORGANISM: Homo sapiens

<400> SEQUENCE: 219

Asp Val Asn Thr Tyr Asn Ala Ala Ile Ala Tyr Thr Ile Leu Ser Gln
1               5                   10                  15

<210> SEQ ID NO 220
<211> LENGTH: 15
<212> TYPE: PRT
<213> ORGANISM: Homo sapiens

<400> SEQUENCE: 220

Glu Gly Lys Val Phe Tyr Ser Ile Thr Gly Gln Gly Ala Asp Thr
1               5                   10                  15

<210> SEQ ID NO 221
<211> LENGTH: 17
<212> TYPE: PRT
<213> ORGANISM: Homo sapiens

<400> SEQUENCE: 221

Glu Gly Lys Val Phe Tyr Ser Ile Thr Gly Gln Gly Ala Asp Thr Pro
1               5                   10                  15

Pro

<210> SEQ ID NO 222
<211> LENGTH: 18
<212> TYPE: PRT
<213> ORGANISM: Homo sapiens

<400> SEQUENCE: 222

Glu Gly Lys Val Phe Tyr Ser Ile Thr Gly Gln Gly Ala Asp Thr Pro
1               5                   10                  15

Pro Val

<210> SEQ ID NO 223
<211> LENGTH: 18
<212> TYPE: PRT
<213> ORGANISM: Homo sapiens

<400> SEQUENCE: 223

Glu Leu Pro Asp Lys Asn Met Phe Thr Ile Asn Arg Asn Thr Gly Val
```

Ile Ser

<210> SEQ ID NO 224
<211> LENGTH: 13
<212> TYPE: PRT
<213> ORGANISM: Homo sapiens

<400> SEQUENCE: 224

Gly Gly Gln Phe Val Val Thr Thr Asn Pro Val Asn Asn
1               5                   10

<210> SEQ ID NO 225
<211> LENGTH: 14
<212> TYPE: PRT
<213> ORGANISM: Homo sapiens

<400> SEQUENCE: 225

Gly Lys Val Phe Tyr Ser Ile Thr Gly Gln Gly Ala Asp Thr
1               5                   10

<210> SEQ ID NO 226
<211> LENGTH: 16
<212> TYPE: PRT
<213> ORGANISM: Homo sapiens

<400> SEQUENCE: 226

Gly Pro Phe Pro Lys Asn Leu Val Gln Ile Lys Ser Asn Lys Asp Lys
1               5                   10                  15

<210> SEQ ID NO 227
<211> LENGTH: 17
<212> TYPE: PRT
<213> ORGANISM: Homo sapiens

<400> SEQUENCE: 227

Gly Pro Phe Pro Lys Asn Leu Val Gln Ile Lys Ser Asn Lys Asp Lys
1               5                   10                  15

Glu

<210> SEQ ID NO 228
<211> LENGTH: 19
<212> TYPE: PRT
<213> ORGANISM: Homo sapiens

<400> SEQUENCE: 228

Gly Pro Phe Pro Lys Asn Leu Val Gln Ile Lys Ser Asn Lys Asp Lys
1               5                   10                  15

Glu Gly Lys

<210> SEQ ID NO 229
<211> LENGTH: 13
<212> TYPE: PRT
<213> ORGANISM: Homo sapiens

<400> SEQUENCE: 229

Lys Asn Met Phe Thr Ile Asn Arg Asn Thr Gly Val Ile
1               5                   10

<210> SEQ ID NO 230
<211> LENGTH: 14
<212> TYPE: PRT
<213> ORGANISM: Homo sapiens

<400> SEQUENCE: 230

Lys Asn Met Phe Thr Ile Asn Arg Asn Thr Gly Val Ile Ser
1               5                   10

<210> SEQ ID NO 231
<211> LENGTH: 14
<212> TYPE: PRT
<213> ORGANISM: Homo sapiens

<400> SEQUENCE: 231

Leu Pro Asp Lys Asn Met Phe Thr Ile Asn Arg Asn Thr Gly
1               5                   10

<210> SEQ ID NO 232
<211> LENGTH: 16
<212> TYPE: PRT
<213> ORGANISM: Homo sapiens

<400> SEQUENCE: 232

Leu Pro Asp Lys Asn Met Phe Thr Ile Asn Arg Asn Thr Gly Val Ile
1               5                   10                  15

<210> SEQ ID NO 233
<211> LENGTH: 17
<212> TYPE: PRT
<213> ORGANISM: Homo sapiens

<400> SEQUENCE: 233

Leu Pro Asp Lys Asn Met Phe Thr Ile Asn Arg Asn Thr Gly Val Ile
1               5                   10                  15
Ser

<210> SEQ ID NO 234
<211> LENGTH: 18
<212> TYPE: PRT
<213> ORGANISM: Homo sapiens

<400> SEQUENCE: 234

Pro Glu Leu Pro Asp Lys Asn Met Phe Thr Ile Asn Arg Asn Thr Gly
1               5                   10                  15
Val Ile

<210> SEQ ID NO 235
<211> LENGTH: 19
<212> TYPE: PRT
<213> ORGANISM: Homo sapiens

<400> SEQUENCE: 235

Pro Glu Leu Pro Asp Lys Asn Met Phe Thr Ile Asn Arg Asn Thr Gly
1               5                   10                  15
Val Ile Ser

<210> SEQ ID NO 236
<211> LENGTH: 21
<212> TYPE: PRT
<213> ORGANISM: Homo sapiens

<400> SEQUENCE: 236

Gln Asp Pro Glu Leu Pro Asp Lys Asn Met Phe Thr Ile Asn Arg Asn
1               5                   10                  15
Thr Gly Val Ile Ser

20

<210> SEQ ID NO 237
<211> LENGTH: 22
<212> TYPE: PRT
<213> ORGANISM: Homo sapiens

<400> SEQUENCE: 237

Ser Gln Asp Pro Glu Leu Pro Asp Lys Asn Met Phe Thr Ile Asn Arg
1               5                   10                  15

Asn Thr Gly Val Ile Ser
            20

<210> SEQ ID NO 238
<211> LENGTH: 25
<212> TYPE: PRT
<213> ORGANISM: Homo sapiens

<400> SEQUENCE: 238

Ser Gln Asp Pro Glu Leu Pro Asp Lys Asn Met Phe Thr Ile Asn Arg
1               5                   10                  15

Asn Thr Gly Val Ile Ser Val Val Thr
            20                  25

<210> SEQ ID NO 239
<211> LENGTH: 14
<212> TYPE: PRT
<213> ORGANISM: Homo sapiens

<400> SEQUENCE: 239

Ser Val Pro Arg Tyr Leu Pro Arg Pro Ala Asn Pro Asp Glu
1               5                   10

<210> SEQ ID NO 240
<211> LENGTH: 17
<212> TYPE: PRT
<213> ORGANISM: Homo sapiens

<400> SEQUENCE: 240

Thr Asp Gly Val Ile Thr Val Lys Arg Pro Leu Arg Phe His Asn Pro
1               5                   10                  15

Gln

<210> SEQ ID NO 241
<211> LENGTH: 14
<212> TYPE: PRT
<213> ORGANISM: Homo sapiens

<400> SEQUENCE: 241

Thr Arg Ala Glu Leu Asp Arg Glu Asp Phe Glu His Val Lys
1               5                   10

<210> SEQ ID NO 242
<211> LENGTH: 13
<212> TYPE: PRT
<213> ORGANISM: Homo sapiens

<400> SEQUENCE: 242

Val Pro Arg Tyr Leu Pro Arg Pro Ala Asn Pro Asp Glu
1               5                   10

<210> SEQ ID NO 243
<211> LENGTH: 13

-continued

```
<212> TYPE: PRT
<213> ORGANISM: Homo sapiens

<400> SEQUENCE: 243

Ala Leu Glu Phe Arg Ala Leu Glu Pro Gln Gly Leu Leu
1               5                   10

<210> SEQ ID NO 244
<211> LENGTH: 14
<212> TYPE: PRT
<213> ORGANISM: Homo sapiens

<400> SEQUENCE: 244

Ala Leu Glu Phe Arg Ala Leu Glu Pro Gln Gly Leu Leu Leu
1               5                   10

<210> SEQ ID NO 245
<211> LENGTH: 13
<212> TYPE: PRT
<213> ORGANISM: Homo sapiens

<400> SEQUENCE: 245

Asp Thr Arg Ile Phe Phe Val Asn Pro Ala Pro Pro Tyr
1               5                   10

<210> SEQ ID NO 246
<211> LENGTH: 14
<212> TYPE: PRT
<213> ORGANISM: Homo sapiens

<400> SEQUENCE: 246

Asp Thr Arg Ile Phe Phe Val Asn Pro Ala Pro Pro Tyr Leu
1               5                   10

<210> SEQ ID NO 247
<211> LENGTH: 15
<212> TYPE: PRT
<213> ORGANISM: Homo sapiens

<400> SEQUENCE: 247

Asp Thr Arg Ile Phe Phe Val Asn Pro Ala Pro Pro Tyr Leu Trp
1               5                   10                  15

<210> SEQ ID NO 248
<211> LENGTH: 16
<212> TYPE: PRT
<213> ORGANISM: Homo sapiens

<400> SEQUENCE: 248

Asp Thr Arg Ile Phe Phe Val Asn Pro Ala Pro Pro Tyr Leu Trp Pro
1               5                   10                  15

<210> SEQ ID NO 249
<211> LENGTH: 17
<212> TYPE: PRT
<213> ORGANISM: Homo sapiens

<400> SEQUENCE: 249

Asp Thr Arg Ile Phe Phe Val Asn Pro Ala Pro Pro Tyr Leu Trp Pro
1               5                   10                  15
Ala

<210> SEQ ID NO 250
<211> LENGTH: 12
```

```
<212> TYPE: PRT
<213> ORGANISM: Homo sapiens

<400> SEQUENCE: 250

Glu Phe Arg Ala Leu Glu Pro Gln Gly Leu Leu Leu
1               5                   10

<210> SEQ ID NO 251
<211> LENGTH: 18
<212> TYPE: PRT
<213> ORGANISM: Homo sapiens

<400> SEQUENCE: 251

Gly Ala Pro Val Pro Ala Phe Glu Gly Arg Ser Phe Leu Ala Phe Pro
1               5                   10                  15

Thr Leu

<210> SEQ ID NO 252
<211> LENGTH: 17
<212> TYPE: PRT
<213> ORGANISM: Homo sapiens

<400> SEQUENCE: 252

Gly Asp Thr Arg Ile Phe Phe Val Asn Pro Ala Pro Pro Tyr Leu Trp
1               5                   10                  15

Pro

<210> SEQ ID NO 253
<211> LENGTH: 18
<212> TYPE: PRT
<213> ORGANISM: Homo sapiens

<400> SEQUENCE: 253

Gly Asp Thr Arg Ile Phe Phe Val Asn Pro Ala Pro Pro Tyr Leu Trp
1               5                   10                  15

Pro Ala

<210> SEQ ID NO 254
<211> LENGTH: 16
<212> TYPE: PRT
<213> ORGANISM: Homo sapiens

<400> SEQUENCE: 254

Ile Val Asp Val His Phe Asp Pro Thr Thr Ala Phe Arg Ala Pro Asp
1               5                   10                  15

<210> SEQ ID NO 255
<211> LENGTH: 16
<212> TYPE: PRT
<213> ORGANISM: Homo sapiens

<400> SEQUENCE: 255

Lys Val Arg Val Trp Arg Tyr Leu Lys Gly Lys Asp Leu Val Ala Arg
1               5                   10                  15

<210> SEQ ID NO 256
<211> LENGTH: 13
<212> TYPE: PRT
<213> ORGANISM: Homo sapiens

<400> SEQUENCE: 256

Leu Glu Phe Arg Ala Leu Glu Pro Gln Gly Leu Leu Leu
1               5                   10
```

<210> SEQ ID NO 257
<211> LENGTH: 13
<212> TYPE: PRT
<213> ORGANISM: Homo sapiens

<400> SEQUENCE: 257

Ser Gly Pro Phe Leu Ala Asp Phe Asn Gly Phe Ser His
1               5                   10

<210> SEQ ID NO 258
<211> LENGTH: 19
<212> TYPE: PRT
<213> ORGANISM: Homo sapiens

<400> SEQUENCE: 258

Thr Gly Asp Thr Arg Ile Phe Phe Val Asn Pro Ala Pro Pro Tyr Leu
1               5                   10                  15

Trp Pro Ala

<210> SEQ ID NO 259
<211> LENGTH: 13
<212> TYPE: PRT
<213> ORGANISM: Homo sapiens

<400> SEQUENCE: 259

Thr Arg Ile Phe Phe Val Asn Pro Ala Pro Pro Tyr Leu
1               5                   10

<210> SEQ ID NO 260
<211> LENGTH: 15
<212> TYPE: PRT
<213> ORGANISM: Homo sapiens

<400> SEQUENCE: 260

Val Asp Val His Phe Asp Pro Thr Thr Ala Phe Arg Ala Pro Asp
1               5                   10                  15

<210> SEQ ID NO 261
<211> LENGTH: 16
<212> TYPE: PRT
<213> ORGANISM: Homo sapiens

<400> SEQUENCE: 261

Val Asp Val His Phe Asp Pro Thr Thr Ala Phe Arg Ala Pro Asp Val
1               5                   10                  15

<210> SEQ ID NO 262
<211> LENGTH: 15
<212> TYPE: PRT
<213> ORGANISM: Homo sapiens

<400> SEQUENCE: 262

Val Arg Val Trp Arg Tyr Leu Lys Gly Lys Asp Leu Val Ala Arg
1               5                   10                  15

<210> SEQ ID NO 263
<211> LENGTH: 16
<212> TYPE: PRT
<213> ORGANISM: Homo sapiens

<400> SEQUENCE: 263

Ala Pro Val Pro Ala Phe Glu Gly Arg Ser Phe Leu Ala Phe Pro Thr
1               5                   10                  15

<210> SEQ ID NO 264
<211> LENGTH: 17
<212> TYPE: PRT
<213> ORGANISM: Homo sapiens

<400> SEQUENCE: 264

Ala Pro Val Pro Ala Phe Glu Gly Arg Ser Phe Leu Ala Phe Pro Thr
1               5                   10                  15

Leu

<210> SEQ ID NO 265
<211> LENGTH: 15
<212> TYPE: PRT
<213> ORGANISM: Homo sapiens

<400> SEQUENCE: 265

Ala Leu Arg Gly Leu Leu Pro Val Leu Gly Gln Pro Ile Ile Arg
1               5                   10                  15

<210> SEQ ID NO 266
<211> LENGTH: 16
<212> TYPE: PRT
<213> ORGANISM: Homo sapiens

<400> SEQUENCE: 266

Asp Leu Pro Gly Arg Phe Val Ala Glu Ser Ala Glu Val Leu Leu Pro
1               5                   10                  15

<210> SEQ ID NO 267
<211> LENGTH: 17
<212> TYPE: PRT
<213> ORGANISM: Homo sapiens

<400> SEQUENCE: 267

Asp Leu Pro Gly Arg Phe Val Ala Glu Ser Ala Glu Val Leu Leu Pro
1               5                   10                  15

Arg

<210> SEQ ID NO 268
<211> LENGTH: 13
<212> TYPE: PRT
<213> ORGANISM: Homo sapiens

<400> SEQUENCE: 268

Gly Gln Pro Ile Ile Arg Ser Ile Pro Gln Gly Ile Val
1               5                   10

<210> SEQ ID NO 269
<211> LENGTH: 14
<212> TYPE: PRT
<213> ORGANISM: Homo sapiens

<400> SEQUENCE: 269

Gly Gln Pro Ile Ile Arg Ser Ile Pro Gln Gly Ile Val Ala
1               5                   10

<210> SEQ ID NO 270
<211> LENGTH: 15
<212> TYPE: PRT
<213> ORGANISM: Homo sapiens

<400> SEQUENCE: 270

-continued

```
Leu Ala Leu Glu Phe Arg Ala Leu Glu Pro Gln Gly Leu Leu Leu
1               5                   10                  15

<210> SEQ ID NO 271
<211> LENGTH: 15
<212> TYPE: PRT
<213> ORGANISM: Homo sapiens

<400> SEQUENCE: 271

Leu Gly Gln Pro Ile Ile Arg Ser Ile Pro Gln Gly Ile Val Ala
1               5                   10                  15

<210> SEQ ID NO 272
<211> LENGTH: 14
<212> TYPE: PRT
<213> ORGANISM: Homo sapiens

<400> SEQUENCE: 272

Leu Pro Ala Ala Leu Ala Cys Trp Gly Val Arg Gly Ser Leu
1               5                   10

<210> SEQ ID NO 273
<211> LENGTH: 14
<212> TYPE: PRT
<213> ORGANISM: Homo sapiens

<400> SEQUENCE: 273

Leu Pro Gly Arg Phe Val Ala Glu Ser Ala Glu Val Leu Leu
1               5                   10

<210> SEQ ID NO 274
<211> LENGTH: 15
<212> TYPE: PRT
<213> ORGANISM: Homo sapiens

<400> SEQUENCE: 274

Leu Pro Gly Arg Phe Val Ala Glu Ser Ala Glu Val Leu Leu Pro
1               5                   10                  15

<210> SEQ ID NO 275
<211> LENGTH: 16
<212> TYPE: PRT
<213> ORGANISM: Homo sapiens

<400> SEQUENCE: 275

Leu Pro Gly Arg Phe Val Ala Glu Ser Ala Glu Val Leu Leu Pro Arg
1               5                   10                  15

<210> SEQ ID NO 276
<211> LENGTH: 14
<212> TYPE: PRT
<213> ORGANISM: Homo sapiens

<400> SEQUENCE: 276

Leu Arg Gly Leu Leu Pro Val Leu Gly Gln Pro Ile Ile Arg
1               5                   10

<210> SEQ ID NO 277
<211> LENGTH: 15
<212> TYPE: PRT
<213> ORGANISM: Homo sapiens

<400> SEQUENCE: 277

Pro Gly Arg Phe Val Ala Glu Ser Ala Glu Val Leu Leu Pro Arg
1               5                   10                  15
```

<210> SEQ ID NO 278
<211> LENGTH: 16
<212> TYPE: PRT
<213> ORGANISM: Homo sapiens

<400> SEQUENCE: 278

Pro Gly Arg Phe Val Ala Glu Ser Ala Glu Val Leu Leu Pro Arg Leu
1               5                   10                  15

<210> SEQ ID NO 279
<211> LENGTH: 13
<212> TYPE: PRT
<213> ORGANISM: Homo sapiens

<400> SEQUENCE: 279

Gln Pro Ile Ile Arg Ser Ile Pro Gln Gly Ile Val Ala
1               5                   10

<210> SEQ ID NO 280
<211> LENGTH: 13
<212> TYPE: PRT
<213> ORGANISM: Homo sapiens

<400> SEQUENCE: 280

Arg Gly Leu Leu Pro Val Leu Gly Gln Pro Ile Ile Arg
1               5                   10

<210> SEQ ID NO 281
<211> LENGTH: 15
<212> TYPE: PRT
<213> ORGANISM: Homo sapiens

<400> SEQUENCE: 281

Ser Arg Thr Leu Ala Gly Glu Thr Gly Gln Glu Ala Ala Pro Leu
1               5                   10                  15

<210> SEQ ID NO 282
<211> LENGTH: 15
<212> TYPE: PRT
<213> ORGANISM: Homo sapiens

<400> SEQUENCE: 282

Ser Thr Glu Arg Val Arg Glu Leu Ala Val Ala Leu Ala Gln Lys
1               5                   10                  15

<210> SEQ ID NO 283
<211> LENGTH: 13
<212> TYPE: PRT
<213> ORGANISM: Homo sapiens

<400> SEQUENCE: 283

Thr Asp Ala Val Leu Pro Leu Thr Val Ala Glu Val Gln
1               5                   10

<210> SEQ ID NO 284
<211> LENGTH: 14
<212> TYPE: PRT
<213> ORGANISM: Homo sapiens

<400> SEQUENCE: 284

Val Ala Glu Val Gln Lys Leu Leu Gly Pro His Val Glu Gly
1               5                   10

```
<210> SEQ ID NO 285
<211> LENGTH: 16
<212> TYPE: PRT
<213> ORGANISM: Homo sapiens

<400> SEQUENCE: 285

Val Ala Glu Val Gln Lys Leu Leu Gly Pro His Val Glu Gly Leu Lys
1               5                   10                  15

<210> SEQ ID NO 286
<211> LENGTH: 16
<212> TYPE: PRT
<213> ORGANISM: Homo sapiens

<400> SEQUENCE: 286

Val Leu Gly Gln Pro Ile Ile Arg Ser Ile Pro Gln Gly Ile Val Ala
1               5                   10                  15

<210> SEQ ID NO 287
<211> LENGTH: 15
<212> TYPE: PRT
<213> ORGANISM: Homo sapiens

<400> SEQUENCE: 287

Val Arg Gly Ser Leu Leu Ser Glu Ala Asp Val Arg Ala Leu Gly
1               5                   10                  15

<210> SEQ ID NO 288
<211> LENGTH: 16
<212> TYPE: PRT
<213> ORGANISM: Homo sapiens

<400> SEQUENCE: 288

Val Arg Gly Ser Leu Leu Ser Glu Ala Asp Val Arg Ala Leu Gly Gly
1               5                   10                  15

<210> SEQ ID NO 289
<211> LENGTH: 15
<212> TYPE: PRT
<213> ORGANISM: Homo sapiens

<400> SEQUENCE: 289

Leu Pro Ala Ala Leu Ala Cys Trp Gly Val Arg Gly Ser Leu Leu
1               5                   10                  15

<210> SEQ ID NO 290
<211> LENGTH: 16
<212> TYPE: PRT
<213> ORGANISM: Homo sapiens

<400> SEQUENCE: 290

Ala Ile Lys Val Leu Arg Glu Asn Thr Ser Pro Lys Ala Asn Lys Glu
1               5                   10                  15

<210> SEQ ID NO 291
<211> LENGTH: 18
<212> TYPE: PRT
<213> ORGANISM: Homo sapiens

<400> SEQUENCE: 291

Asp Pro Ser Pro Leu Gln Arg Tyr Ser Glu Asp Pro Thr Val Pro Leu
1               5                   10                  15

Pro Ser
```

```
<210> SEQ ID NO 292
<211> LENGTH: 19
<212> TYPE: PRT
<213> ORGANISM: Homo sapiens

<400> SEQUENCE: 292

Asp Pro Ser Pro Leu Gln Arg Tyr Ser Glu Asp Pro Thr Val Pro Leu
1               5                   10                  15

Pro Ser Glu

<210> SEQ ID NO 293
<211> LENGTH: 12
<212> TYPE: PRT
<213> ORGANISM: Homo sapiens

<400> SEQUENCE: 293

Glu Leu Val Ser Glu Phe Ser Arg Met Ala Arg Asp
1               5                   10

<210> SEQ ID NO 294
<211> LENGTH: 14
<212> TYPE: PRT
<213> ORGANISM: Homo sapiens

<400> SEQUENCE: 294

Glu Leu Val Ser Glu Phe Ser Arg Met Ala Arg Asp Pro Gln
1               5                   10

<210> SEQ ID NO 295
<211> LENGTH: 19
<212> TYPE: PRT
<213> ORGANISM: Homo sapiens

<400> SEQUENCE: 295

Ile Pro Val Ala Ile Lys Val Leu Arg Glu Asn Thr Ser Pro Lys Ala
1               5                   10                  15

Asn Lys Glu

<210> SEQ ID NO 296
<211> LENGTH: 16
<212> TYPE: PRT
<213> ORGANISM: Homo sapiens

<400> SEQUENCE: 296

Arg Arg Leu Leu Gln Glu Thr Glu Leu Val Glu Pro Leu Thr Pro Ser
1               5                   10                  15

<210> SEQ ID NO 297
<211> LENGTH: 17
<212> TYPE: PRT
<213> ORGANISM: Homo sapiens

<400> SEQUENCE: 297

Ser Pro Gln Pro Glu Tyr Val Asn Gln Pro Asp Val Arg Pro Gln Pro
1               5                   10                  15

Pro

<210> SEQ ID NO 298
<211> LENGTH: 16
<212> TYPE: PRT
<213> ORGANISM: Homo sapiens

<400> SEQUENCE: 298
```

```
Val Lys Pro Asp Leu Ser Tyr Met Pro Ile Trp Lys Phe Pro Asp Glu
1               5                   10                  15
```

<210> SEQ ID NO 299
<211> LENGTH: 15
<212> TYPE: PRT
<213> ORGANISM: Homo sapiens

<400> SEQUENCE: 299

```
Ala Ser Gly Met Arg Tyr Leu Ala Thr Leu Asn Phe Val His Arg
1               5                   10                  15
```

<210> SEQ ID NO 300
<211> LENGTH: 16
<212> TYPE: PRT
<213> ORGANISM: Homo sapiens

<400> SEQUENCE: 300

```
Ile Ala Ser Gly Met Arg Tyr Leu Ala Thr Leu Asn Phe Val His Arg
1               5                   10                  15
```

<210> SEQ ID NO 301
<211> LENGTH: 13
<212> TYPE: PRT
<213> ORGANISM: Homo sapiens

<400> SEQUENCE: 301

```
Lys Glu Val Lys Ile Met Ser Arg Leu Lys Asp Pro Asn
1               5                   10
```

<210> SEQ ID NO 302
<211> LENGTH: 13
<212> TYPE: PRT
<213> ORGANISM: Homo sapiens

<400> SEQUENCE: 302

```
Leu Asn Gln Phe Leu Ser Ala His Gln Leu Glu Asp Lys
1               5                   10
```

<210> SEQ ID NO 303
<211> LENGTH: 15
<212> TYPE: PRT
<213> ORGANISM: Homo sapiens

<400> SEQUENCE: 303

```
Asn Pro Ala Tyr Arg Leu Leu Leu Ala Thr Tyr Ala Arg Pro Pro
1               5                   10                  15
```

<210> SEQ ID NO 304
<211> LENGTH: 16
<212> TYPE: PRT
<213> ORGANISM: Homo sapiens

<400> SEQUENCE: 304

```
Asn Pro Ala Tyr Arg Leu Leu Leu Ala Thr Tyr Ala Arg Pro Pro Arg
1               5                   10                  15
```

<210> SEQ ID NO 305
<211> LENGTH: 16
<212> TYPE: PRT
<213> ORGANISM: Homo sapiens

<400> SEQUENCE: 305

```
Ser Asn Pro Ala Tyr Arg Leu Leu Leu Ala Thr Tyr Ala Arg Pro Pro
1               5                   10                  15
```

<210> SEQ ID NO 306
<211> LENGTH: 17
<212> TYPE: PRT
<213> ORGANISM: Homo sapiens

<400> SEQUENCE: 306

Ser Asn Pro Ala Tyr Arg Leu Leu Ala Thr Tyr Ala Arg Pro Pro
1               5                   10                  15
Arg

<210> SEQ ID NO 307
<211> LENGTH: 16
<212> TYPE: PRT
<213> ORGANISM: Homo sapiens

<400> SEQUENCE: 307

Asp Pro Ser Thr Asp Tyr Tyr Gln Glu Leu Gln Arg Asp Ile Ser Glu
1               5                   10                  15

<210> SEQ ID NO 308
<211> LENGTH: 15
<212> TYPE: PRT
<213> ORGANISM: Homo sapiens

<400> SEQUENCE: 308

Val Glu Thr Gln Phe Asn Gln Tyr Lys Thr Glu Ala Ala Ser Arg
1               5                   10                  15

<210> SEQ ID NO 309
<211> LENGTH: 16
<212> TYPE: PRT
<213> ORGANISM: Homo sapiens

<400> SEQUENCE: 309

Gly Arg Gln Val Trp Val Tyr Thr Gly Ala Ser Val Leu Gly Pro Arg
1               5                   10                  15

<210> SEQ ID NO 310
<211> LENGTH: 17
<212> TYPE: PRT
<213> ORGANISM: Homo sapiens

<400> SEQUENCE: 310

Asn Gln Leu Tyr Leu Phe Lys Asp Gly Lys Tyr Trp Arg Phe Ser Glu
1               5                   10                  15
Gly

<210> SEQ ID NO 311
<211> LENGTH: 15
<212> TYPE: PRT
<213> ORGANISM: Homo sapiens

<400> SEQUENCE: 311

Arg Gln Val Trp Val Tyr Thr Gly Ala Ser Val Leu Gly Pro Arg
1               5                   10                  15

<210> SEQ ID NO 312
<211> LENGTH: 15
<212> TYPE: PRT
<213> ORGANISM: Homo sapiens

<400> SEQUENCE: 312

Ser Gly Arg Gln Val Trp Val Tyr Thr Gly Ala Ser Val Leu Gly
1               5                   10                  15

<210> SEQ ID NO 313
<211> LENGTH: 16
<212> TYPE: PRT
<213> ORGANISM: Homo sapiens

<400> SEQUENCE: 313

Ser Gly Arg Gln Val Trp Val Tyr Thr Gly Ala Ser Val Leu Gly Pro
1               5                   10                  15

<210> SEQ ID NO 314
<211> LENGTH: 17
<212> TYPE: PRT
<213> ORGANISM: Homo sapiens

<400> SEQUENCE: 314

Ser Gly Arg Gln Val Trp Val Tyr Thr Gly Ala Ser Val Leu Gly Pro
1               5                   10                  15

Arg

<210> SEQ ID NO 315
<211> LENGTH: 15
<212> TYPE: PRT
<213> ORGANISM: Homo sapiens

<400> SEQUENCE: 315

Val Asp Pro Arg Ser Ala Ser Glu Val Asp Arg Met Phe Pro Gly
1               5                   10                  15

<210> SEQ ID NO 316
<211> LENGTH: 13
<212> TYPE: PRT
<213> ORGANISM: Homo sapiens

<400> SEQUENCE: 316

Gly Glu Val Ala Pro Asp Ala Lys Ser Phe Val Leu Asn
1               5                   10

<210> SEQ ID NO 317
<211> LENGTH: 19
<212> TYPE: PRT
<213> ORGANISM: Homo sapiens

<400> SEQUENCE: 317

Leu Thr Val Lys Leu Pro Asp Gly Tyr Glu Phe Lys Phe Pro Asn Arg
1               5                   10                  15

Leu Asn Leu

<210> SEQ ID NO 318
<211> LENGTH: 15
<212> TYPE: PRT
<213> ORGANISM: Homo sapiens

<400> SEQUENCE: 318

Val Arg Gly Glu Val Ala Pro Asp Ala Lys Ser Phe Val Leu Asn
1               5                   10                  15

<210> SEQ ID NO 319
<211> LENGTH: 17
<212> TYPE: PRT
<213> ORGANISM: Homo sapiens

```
<400> SEQUENCE: 319

Val Arg Gly Glu Val Ala Pro Asp Ala Lys Ser Phe Val Leu Asn Leu
1               5                   10                  15

Gly

<210> SEQ ID NO 320
<211> LENGTH: 9
<212> TYPE: PRT
<213> ORGANISM: Homo sapiens

<400> SEQUENCE: 320

Ala Thr Ser Lys Ile Pro Leu Ala Leu
1               5

<210> SEQ ID NO 321
<211> LENGTH: 8
<212> TYPE: PRT
<213> ORGANISM: Homo sapiens

<400> SEQUENCE: 321

Ile Thr Ser Ser Arg Thr Thr Ile
1               5

<210> SEQ ID NO 322
<211> LENGTH: 9
<212> TYPE: PRT
<213> ORGANISM: Homo sapiens

<400> SEQUENCE: 322

Leu Asn Phe Thr Ile Thr Asn Leu Gln
1               5

<210> SEQ ID NO 323
<211> LENGTH: 10
<212> TYPE: PRT
<213> ORGANISM: Homo sapiens

<400> SEQUENCE: 323

Thr Ala Thr Ser Pro Met Val Pro Ala Ser
1               5                   10

<210> SEQ ID NO 324
<211> LENGTH: 9
<212> TYPE: PRT
<213> ORGANISM: Homo sapiens

<400> SEQUENCE: 324

Thr Thr Leu Pro Glu Ser Arg Pro Ser
1               5

<210> SEQ ID NO 325
<211> LENGTH: 9
<212> TYPE: PRT
<213> ORGANISM: Homo sapiens

<400> SEQUENCE: 325

Val Glu Leu Arg Val Leu Ala Leu Pro
1               5

<210> SEQ ID NO 326
<211> LENGTH: 9
<212> TYPE: PRT
<213> ORGANISM: Homo sapiens
```

```
<400> SEQUENCE: 326

Ala Glu Asp Asn Leu Ile His Lys Phe
1               5

<210> SEQ ID NO 327
<211> LENGTH: 9
<212> TYPE: PRT
<213> ORGANISM: Homo sapiens

<400> SEQUENCE: 327

Arg Glu Asp Leu Glu Arg Leu Gly Val
1               5

<210> SEQ ID NO 328
<211> LENGTH: 10
<212> TYPE: PRT
<213> ORGANISM: Homo sapiens

<400> SEQUENCE: 328

Asp Thr Lys Asp Pro Ala Val Thr Glu Trp
1               5                   10

<210> SEQ ID NO 329
<211> LENGTH: 9
<212> TYPE: PRT
<213> ORGANISM: Homo sapiens

<400> SEQUENCE: 329

Ile Leu Ile Ser Lys Leu Leu Gly Ala
1               5

<210> SEQ ID NO 330
<211> LENGTH: 9
<212> TYPE: PRT
<213> ORGANISM: Homo sapiens

<400> SEQUENCE: 330

Ser Glu Ser Leu Arg Thr Leu Glu Phe
1               5

<210> SEQ ID NO 331
<211> LENGTH: 9
<212> TYPE: PRT
<213> ORGANISM: Homo sapiens

<400> SEQUENCE: 331

Val Leu Ala Glu Leu Val Ala Lys Leu
1               5

<210> SEQ ID NO 332
<211> LENGTH: 9
<212> TYPE: PRT
<213> ORGANISM: Homo sapiens

<400> SEQUENCE: 332

Ile Asn Thr Ser Ile Leu Leu Ile Phe
1               5

<210> SEQ ID NO 333
<211> LENGTH: 9
<212> TYPE: PRT
<213> ORGANISM: Homo sapiens

<400> SEQUENCE: 333
```

```
Ala Leu Gln Pro Leu Leu His Thr Val
1               5
```

<210> SEQ ID NO 334
<211> LENGTH: 9
<212> TYPE: PRT
<213> ORGANISM: Homo sapiens

<400> SEQUENCE: 334

```
Arg Leu Met Asp Asn Leu Pro Gln Leu
1               5
```

<210> SEQ ID NO 335
<211> LENGTH: 9
<212> TYPE: PRT
<213> ORGANISM: Homo sapiens

<400> SEQUENCE: 335

```
Leu Ile Ile Ser Pro Thr Arg Glu Leu
1               5
```

<210> SEQ ID NO 336
<211> LENGTH: 8
<212> TYPE: PRT
<213> ORGANISM: Homo sapiens

<400> SEQUENCE: 336

```
Ala Asp Ser Lys Val Leu Leu Phe
1               5
```

<210> SEQ ID NO 337
<211> LENGTH: 11
<212> TYPE: PRT
<213> ORGANISM: Homo sapiens

<400> SEQUENCE: 337

```
Asp Ser Leu Leu Glu Gln Ala Asn Asn Ala Ile
1               5                   10
```

<210> SEQ ID NO 338
<211> LENGTH: 10
<212> TYPE: PRT
<213> ORGANISM: Homo sapiens

<400> SEQUENCE: 338

```
Asp Tyr Gln Gly Ile Lys Phe Val Lys Arg
1               5                   10
```

<210> SEQ ID NO 339
<211> LENGTH: 9
<212> TYPE: PRT
<213> ORGANISM: Homo sapiens

<400> SEQUENCE: 339

```
Glu Val Val Gly Tyr Phe Gly Arg Phe
1               5
```

<210> SEQ ID NO 340
<211> LENGTH: 9
<212> TYPE: PRT
<213> ORGANISM: Homo sapiens

<400> SEQUENCE: 340

```
Lys Tyr Val Lys Gly Leu Ile Ser Ile
1               5
```

```
<210> SEQ ID NO 341
<211> LENGTH: 9
<212> TYPE: PRT
<213> ORGANISM: Homo sapiens

<400> SEQUENCE: 341

Ser Ile Gly Thr Pro Leu Asp Pro Lys
1               5

<210> SEQ ID NO 342
<211> LENGTH: 9
<212> TYPE: PRT
<213> ORGANISM: Homo sapiens

<400> SEQUENCE: 342

Thr Ala Ser Asp Lys Ile Leu Ile Val
1               5

<210> SEQ ID NO 343
<211> LENGTH: 9
<212> TYPE: PRT
<213> ORGANISM: Homo sapiens

<400> SEQUENCE: 343

Gly Val Ile Lys Val Ile Ser Gly Phe
1               5

<210> SEQ ID NO 344
<211> LENGTH: 9
<212> TYPE: PRT
<213> ORGANISM: Homo sapiens

<400> SEQUENCE: 344

Lys Val Lys Leu Glu Asn Lys Leu Lys
1               5

<210> SEQ ID NO 345
<211> LENGTH: 9
<212> TYPE: PRT
<213> ORGANISM: Homo sapiens

<400> SEQUENCE: 345

Ser Ser Ser Glu Pro Val His Ala Lys
1               5

<210> SEQ ID NO 346
<211> LENGTH: 10
<212> TYPE: PRT
<213> ORGANISM: Homo sapiens

<400> SEQUENCE: 346

Ser Ser Ser Glu Pro Val His Ala Lys Lys
1               5                   10

<210> SEQ ID NO 347
<211> LENGTH: 9
<212> TYPE: PRT
<213> ORGANISM: Homo sapiens

<400> SEQUENCE: 347

Leu Ser Asp Gln Leu Ala Gln Ala Ile
1               5
```

```
<210> SEQ ID NO 348
<211> LENGTH: 9
<212> TYPE: PRT
<213> ORGANISM: Homo sapiens

<400> SEQUENCE: 348

Leu Ser Asp Ile Val Ile Glu Lys Tyr
1               5

<210> SEQ ID NO 349
<211> LENGTH: 9
<212> TYPE: PRT
<213> ORGANISM: Homo sapiens

<400> SEQUENCE: 349

Ser Leu Asp Asp His Val Val Ala Val
1               5

<210> SEQ ID NO 350
<211> LENGTH: 9
<212> TYPE: PRT
<213> ORGANISM: Homo sapiens

<400> SEQUENCE: 350

Ser Gln Ile Asp Gln Gln Asn Ser Val
1               5

<210> SEQ ID NO 351
<211> LENGTH: 11
<212> TYPE: PRT
<213> ORGANISM: Homo sapiens

<400> SEQUENCE: 351

Ser Thr Ile Asp Pro Ser Gly Thr Arg Ser Lys
1               5                   10

<210> SEQ ID NO 352
<211> LENGTH: 9
<212> TYPE: PRT
<213> ORGANISM: Homo sapiens

<400> SEQUENCE: 352

Val Phe Arg Asp Gln Glu Pro Lys Ile
1               5

<210> SEQ ID NO 353
<211> LENGTH: 9
<212> TYPE: PRT
<213> ORGANISM: Homo sapiens

<400> SEQUENCE: 353

Val Leu Arg Glu Lys Glu Ala Ala Leu
1               5

<210> SEQ ID NO 354
<211> LENGTH: 9
<212> TYPE: PRT
<213> ORGANISM: Homo sapiens

<400> SEQUENCE: 354

Thr Arg Leu Gln Gln Ala Gln Ala Leu
1               5

<210> SEQ ID NO 355
<211> LENGTH: 9
```

```
<212> TYPE: PRT
<213> ORGANISM: Homo sapiens

<400> SEQUENCE: 355

Val Ala Ala Pro Glu His Ile Ser Tyr
1               5

<210> SEQ ID NO 356
<211> LENGTH: 8
<212> TYPE: PRT
<213> ORGANISM: Homo sapiens

<400> SEQUENCE: 356

Asn Ser Lys Lys Lys Val Ala Leu
1               5

<210> SEQ ID NO 357
<211> LENGTH: 9
<212> TYPE: PRT
<213> ORGANISM: Homo sapiens

<400> SEQUENCE: 357

Gln Asn Ser Lys Lys Lys Val Ala Leu
1               5

<210> SEQ ID NO 358
<211> LENGTH: 8
<212> TYPE: PRT
<213> ORGANISM: Homo sapiens

<400> SEQUENCE: 358

Arg Asp Asn Thr Val His Ser Phe
1               5

<210> SEQ ID NO 359
<211> LENGTH: 9
<212> TYPE: PRT
<213> ORGANISM: Homo sapiens

<400> SEQUENCE: 359

Lys Gln Val Ser Glu Phe Met Thr Trp
1               5

<210> SEQ ID NO 360
<211> LENGTH: 9
<212> TYPE: PRT
<213> ORGANISM: Homo sapiens

<400> SEQUENCE: 360

Lys Thr Lys Pro Gln Ser Ile Gln Arg
1               5

<210> SEQ ID NO 361
<211> LENGTH: 8
<212> TYPE: PRT
<213> ORGANISM: Homo sapiens

<400> SEQUENCE: 361

Thr His Ile Glu Leu Glu Arg Leu
1               5

<210> SEQ ID NO 362
<211> LENGTH: 8
<212> TYPE: PRT
<213> ORGANISM: Homo sapiens
```

-continued

```
<400> SEQUENCE: 362

Ile Ala Pro Lys Ile Leu Gln Leu
1               5

<210> SEQ ID NO 363
<211> LENGTH: 9
<212> TYPE: PRT
<213> ORGANISM: Homo sapiens

<400> SEQUENCE: 363

Asp Ile Ala Ser Val Ser Gly Arg Trp
1               5

<210> SEQ ID NO 364
<211> LENGTH: 9
<212> TYPE: PRT
<213> ORGANISM: Homo sapiens

<400> SEQUENCE: 364

Lys Pro Lys Gln Pro Ser Lys Ser Val
1               5

<210> SEQ ID NO 365
<211> LENGTH: 9
<212> TYPE: PRT
<213> ORGANISM: Homo sapiens

<400> SEQUENCE: 365

Met Pro Ala Glu Thr Ile Lys Glu Leu
1               5

<210> SEQ ID NO 366
<211> LENGTH: 9
<212> TYPE: PRT
<213> ORGANISM: Homo sapiens

<400> SEQUENCE: 366

Ser Ala Val Lys Glu Gly Thr Ala Met
1               5

<210> SEQ ID NO 367
<211> LENGTH: 9
<212> TYPE: PRT
<213> ORGANISM: Homo sapiens

<400> SEQUENCE: 367

Glu Glu Glu Lys Leu Gln Ala Ala Phe
1               5

<210> SEQ ID NO 368
<211> LENGTH: 8
<212> TYPE: PRT
<213> ORGANISM: Homo sapiens

<400> SEQUENCE: 368

Asp Glu Phe Asn Leu Gln Lys Met
1               5

<210> SEQ ID NO 369
<211> LENGTH: 8
<212> TYPE: PRT
<213> ORGANISM: Homo sapiens

<400> SEQUENCE: 369
```

Asp Glu Tyr Lys Val Thr Ala Phe
1               5

<210> SEQ ID NO 370
<211> LENGTH: 9
<212> TYPE: PRT
<213> ORGANISM: Homo sapiens

<400> SEQUENCE: 370

Glu Thr Asn Ile Gly Gly Leu Asn Trp
1               5

<210> SEQ ID NO 371
<211> LENGTH: 9
<212> TYPE: PRT
<213> ORGANISM: Homo sapiens

<400> SEQUENCE: 371

Phe Pro Gln Thr Ala Leu Val Ser Phe
1               5

<210> SEQ ID NO 372
<211> LENGTH: 11
<212> TYPE: PRT
<213> ORGANISM: Homo sapiens

<400> SEQUENCE: 372

Gly Glu Phe Gly Lys Lys Ala Asp Gly Leu Leu
1               5                   10

<210> SEQ ID NO 373
<211> LENGTH: 9
<212> TYPE: PRT
<213> ORGANISM: Homo sapiens

<400> SEQUENCE: 373

Gly Ser Met Gly Ser Phe Ser Glu Lys
1               5

<210> SEQ ID NO 374
<211> LENGTH: 11
<212> TYPE: PRT
<213> ORGANISM: Homo sapiens

<400> SEQUENCE: 374

Ile Phe Leu Ile Asp Gly Val Thr Gly Arg Ile
1               5                   10

<210> SEQ ID NO 375
<211> LENGTH: 8
<212> TYPE: PRT
<213> ORGANISM: Homo sapiens

<400> SEQUENCE: 375

Ile Pro Pro Glu Val Gln Arg Ile
1               5

<210> SEQ ID NO 376
<211> LENGTH: 9
<212> TYPE: PRT
<213> ORGANISM: Homo sapiens

<400> SEQUENCE: 376

Ile Pro Tyr Ser Pro Asp Val Gln Ile

<210> SEQ ID NO 377
<211> LENGTH: 9
<212> TYPE: PRT
<213> ORGANISM: Homo sapiens

<400> SEQUENCE: 377

Gln Val Ala Pro Pro Val Leu Lys Arg
1               5

<210> SEQ ID NO 378
<211> LENGTH: 9
<212> TYPE: PRT
<213> ORGANISM: Homo sapiens

<400> SEQUENCE: 378

Thr Glu Lys Asn Val Ile Ala Ala Leu
1               5

<210> SEQ ID NO 379
<211> LENGTH: 9
<212> TYPE: PRT
<213> ORGANISM: Homo sapiens

<400> SEQUENCE: 379

Val Gly Lys Val Lys Phe Ala Ser Leu
1               5

<210> SEQ ID NO 380
<211> LENGTH: 8
<212> TYPE: PRT
<213> ORGANISM: Homo sapiens

<400> SEQUENCE: 380

Val Pro Phe Ser His Val Asn Ile
1               5

<210> SEQ ID NO 381
<211> LENGTH: 9
<212> TYPE: PRT
<213> ORGANISM: Homo sapiens

<400> SEQUENCE: 381

Val Val Tyr Gln Tyr Trp Asn Thr Lys
1               5

<210> SEQ ID NO 382
<211> LENGTH: 9
<212> TYPE: PRT
<213> ORGANISM: Homo sapiens

<400> SEQUENCE: 382

Tyr Pro Ser Lys Gln Phe Asp Val Leu
1               5

<210> SEQ ID NO 383
<211> LENGTH: 9
<212> TYPE: PRT
<213> ORGANISM: Homo sapiens

<400> SEQUENCE: 383

Ala Ala Asp Asp Ser Ala Asp Lys Val
1               5

<210> SEQ ID NO 384
<211> LENGTH: 9
<212> TYPE: PRT
<213> ORGANISM: Homo sapiens

<400> SEQUENCE: 384

His His Lys Glu Lys Gln Thr Asp Val
1               5

<210> SEQ ID NO 385
<211> LENGTH: 9
<212> TYPE: PRT
<213> ORGANISM: Homo sapiens

<400> SEQUENCE: 385

Lys Gln Thr Asp Val Ala Ala Glu Val
1               5

<210> SEQ ID NO 386
<211> LENGTH: 9
<212> TYPE: PRT
<213> ORGANISM: Homo sapiens

<400> SEQUENCE: 386

Lys Ser Ala Phe Pro Ala Gln Ser Lys
1               5

<210> SEQ ID NO 387
<211> LENGTH: 9
<212> TYPE: PRT
<213> ORGANISM: Homo sapiens

<400> SEQUENCE: 387

Asn Glu Val Val Gln Val His Ala Ala
1               5

<210> SEQ ID NO 388
<211> LENGTH: 9
<212> TYPE: PRT
<213> ORGANISM: Homo sapiens

<400> SEQUENCE: 388

Ser Glu Asp Leu Asn Lys His Val Leu
1               5

<210> SEQ ID NO 389
<211> LENGTH: 9
<212> TYPE: PRT
<213> ORGANISM: Homo sapiens

<400> SEQUENCE: 389

Gly Glu Thr Ile His Ile Pro Thr Met
1               5

<210> SEQ ID NO 390
<211> LENGTH: 9
<212> TYPE: PRT
<213> ORGANISM: Homo sapiens

<400> SEQUENCE: 390

Gly Pro Lys Leu Ala Ser Arg Ile Leu
1               5

<210> SEQ ID NO 391

```
<211> LENGTH: 9
<212> TYPE: PRT
<213> ORGANISM: Homo sapiens

<400> SEQUENCE: 391

Gly Val Lys Lys Pro Thr Lys Ala Leu
1               5

<210> SEQ ID NO 392
<211> LENGTH: 9
<212> TYPE: PRT
<213> ORGANISM: Homo sapiens

<400> SEQUENCE: 392

Lys Glu Lys Pro Asp Pro Asn Asn Leu
1               5

<210> SEQ ID NO 393
<211> LENGTH: 9
<212> TYPE: PRT
<213> ORGANISM: Homo sapiens

<400> SEQUENCE: 393

Lys Val Ser Glu Arg Tyr Leu Thr Met
1               5

<210> SEQ ID NO 394
<211> LENGTH: 9
<212> TYPE: PRT
<213> ORGANISM: Homo sapiens

<400> SEQUENCE: 394

Leu Pro Val Phe Asp Lys Glu Glu Leu
1               5

<210> SEQ ID NO 395
<211> LENGTH: 9
<212> TYPE: PRT
<213> ORGANISM: Homo sapiens

<400> SEQUENCE: 395

Leu Ser Lys Leu Thr Asp Ile Gln Tyr
1               5

<210> SEQ ID NO 396
<211> LENGTH: 9
<212> TYPE: PRT
<213> ORGANISM: Homo sapiens

<400> SEQUENCE: 396

Asp Leu Ser Asn Ile Ile Asn Lys Leu
1               5

<210> SEQ ID NO 397
<211> LENGTH: 11
<212> TYPE: PRT
<213> ORGANISM: Homo sapiens

<400> SEQUENCE: 397

Arg Val Trp Asp Val Glu Ser Gly Ser Leu Lys
1               5                   10

<210> SEQ ID NO 398
<211> LENGTH: 9
<212> TYPE: PRT
```

```
<213> ORGANISM: Homo sapiens

<400> SEQUENCE: 398

Ser Pro Thr Thr Ser His Val Gly Ala
1               5

<210> SEQ ID NO 399
<211> LENGTH: 9
<212> TYPE: PRT
<213> ORGANISM: Homo sapiens

<400> SEQUENCE: 399

Val Glu Ile Glu Tyr Val Glu Lys Tyr
1               5

<210> SEQ ID NO 400
<211> LENGTH: 9
<212> TYPE: PRT
<213> ORGANISM: Homo sapiens

<400> SEQUENCE: 400

Val Glu Arg Asn Lys Val Lys Ala Leu
1               5

<210> SEQ ID NO 401
<211> LENGTH: 9
<212> TYPE: PRT
<213> ORGANISM: Homo sapiens

<400> SEQUENCE: 401

Arg Glu Ala Val Ser Lys Glu Asp Leu
1               5

<210> SEQ ID NO 402
<211> LENGTH: 11
<212> TYPE: PRT
<213> ORGANISM: Homo sapiens

<400> SEQUENCE: 402

Ile Met Gly Gly Asn Ser Ile Leu His Ser Ala
1               5                   10

<210> SEQ ID NO 403
<211> LENGTH: 9
<212> TYPE: PRT
<213> ORGANISM: Homo sapiens

<400> SEQUENCE: 403

Lys Gln Phe Glu Gly Ser Thr Ser Phe
1               5

<210> SEQ ID NO 404
<211> LENGTH: 9
<212> TYPE: PRT
<213> ORGANISM: Homo sapiens

<400> SEQUENCE: 404

Glu Glu Phe Leu Arg Gln Glu His Phe
1               5

<210> SEQ ID NO 405
<211> LENGTH: 10
<212> TYPE: PRT
<213> ORGANISM: Homo sapiens
```

```
<400> SEQUENCE: 405

Glu Thr Ile Pro Ser Glu Ile Gln Val Phe
1               5                   10

<210> SEQ ID NO 406
<211> LENGTH: 10
<212> TYPE: PRT
<213> ORGANISM: Homo sapiens

<400> SEQUENCE: 406

Glu Val Gly Glu Ala Leu Lys Thr Val Leu
1               5                   10

<210> SEQ ID NO 407
<211> LENGTH: 9
<212> TYPE: PRT
<213> ORGANISM: Homo sapiens

<400> SEQUENCE: 407

Lys Leu Glu Asp Leu Glu Glu Gln Leu
1               5

<210> SEQ ID NO 408
<211> LENGTH: 8
<212> TYPE: PRT
<213> ORGANISM: Homo sapiens

<400> SEQUENCE: 408

Leu Lys Ile Gln Ser Ile Ala Leu
1               5

<210> SEQ ID NO 409
<211> LENGTH: 11
<212> TYPE: PRT
<213> ORGANISM: Homo sapiens

<400> SEQUENCE: 409

Met Asn Val Leu Thr Glu Trp Leu Ala Ala Thr
1               5                   10

<210> SEQ ID NO 410
<211> LENGTH: 9
<212> TYPE: PRT
<213> ORGANISM: Homo sapiens

<400> SEQUENCE: 410

Ala Ile Gln Asp Lys Leu Phe Gln Val
1               5

<210> SEQ ID NO 411
<211> LENGTH: 9
<212> TYPE: PRT
<213> ORGANISM: Homo sapiens

<400> SEQUENCE: 411

Phe Pro Asn Phe Asp Lys Gln Glu Leu
1               5

<210> SEQ ID NO 412
<211> LENGTH: 9
<212> TYPE: PRT
<213> ORGANISM: Homo sapiens

<400> SEQUENCE: 412
```

Gly Gln Thr Lys Glu Val Leu Val Ile
1               5

<210> SEQ ID NO 413
<211> LENGTH: 9
<212> TYPE: PRT
<213> ORGANISM: Homo sapiens

<400> SEQUENCE: 413

Lys Leu Ile Glu Ser Thr Ser Thr Met
1               5

<210> SEQ ID NO 414
<211> LENGTH: 8
<212> TYPE: PRT
<213> ORGANISM: Homo sapiens

<400> SEQUENCE: 414

Lys Pro Tyr Gln Lys Val Gly Leu
1               5

<210> SEQ ID NO 415
<211> LENGTH: 9
<212> TYPE: PRT
<213> ORGANISM: Homo sapiens

<400> SEQUENCE: 415

Lys Gln Glu Ser Ile Val Leu Lys Leu
1               5

<210> SEQ ID NO 416
<211> LENGTH: 8
<212> TYPE: PRT
<213> ORGANISM: Homo sapiens

<400> SEQUENCE: 416

Asn Ala Asn Asn Arg Leu Leu Leu
1               5

<210> SEQ ID NO 417
<211> LENGTH: 9
<212> TYPE: PRT
<213> ORGANISM: Homo sapiens

<400> SEQUENCE: 417

Ser Glu Val Pro Asn Gly Lys Glu Val
1               5

<210> SEQ ID NO 418
<211> LENGTH: 9
<212> TYPE: PRT
<213> ORGANISM: Homo sapiens

<400> SEQUENCE: 418

Thr Asn Asn Ile Gly Ser Ile Ala Arg
1               5

<210> SEQ ID NO 419
<211> LENGTH: 9
<212> TYPE: PRT
<213> ORGANISM: Homo sapiens

<400> SEQUENCE: 419

Asp Ala Lys Gly Arg Thr Val Ser Leu
1               5

```
<210> SEQ ID NO 420
<211> LENGTH: 8
<212> TYPE: PRT
<213> ORGANISM: Homo sapiens

<400> SEQUENCE: 420

Ile Ile Lys Lys Lys Glu Asp Leu
1               5

<210> SEQ ID NO 421
<211> LENGTH: 9
<212> TYPE: PRT
<213> ORGANISM: Homo sapiens

<400> SEQUENCE: 421

Asp Val Ile Asp Val Val Gln Ala Leu
1               5

<210> SEQ ID NO 422
<211> LENGTH: 8
<212> TYPE: PRT
<213> ORGANISM: Homo sapiens

<400> SEQUENCE: 422

Glu Glu Phe Lys Ile Thr Ser Phe
1               5

<210> SEQ ID NO 423
<211> LENGTH: 8
<212> TYPE: PRT
<213> ORGANISM: Homo sapiens

<400> SEQUENCE: 423

Ser Asp Phe Glu Lys Thr Gly Phe
1               5

<210> SEQ ID NO 424
<211> LENGTH: 9
<212> TYPE: PRT
<213> ORGANISM: Homo sapiens

<400> SEQUENCE: 424

Asp Glu Asp Arg Leu Leu Val Val Phe
1               5

<210> SEQ ID NO 425
<211> LENGTH: 9
<212> TYPE: PRT
<213> ORGANISM: Homo sapiens

<400> SEQUENCE: 425

His His Ser Asn Ile Pro Met Ser Leu
1               5

<210> SEQ ID NO 426
<211> LENGTH: 9
<212> TYPE: PRT
<213> ORGANISM: Homo sapiens

<400> SEQUENCE: 426

Leu Phe Pro Ser Leu Ile Lys Asn Leu
1               5
```

<210> SEQ ID NO 427
<211> LENGTH: 9
<212> TYPE: PRT
<213> ORGANISM: Homo sapiens

<400> SEQUENCE: 427

Asn Thr Asn Ile Pro Ile Gly Asn Lys
1               5

<210> SEQ ID NO 428
<211> LENGTH: 8
<212> TYPE: PRT
<213> ORGANISM: Homo sapiens

<400> SEQUENCE: 428

Ser Asp Gln Val Ala Asp Leu Arg
1               5

<210> SEQ ID NO 429
<211> LENGTH: 9
<212> TYPE: PRT
<213> ORGANISM: Homo sapiens

<400> SEQUENCE: 429

Thr His Phe Ser Phe Pro Leu Arg Leu
1               5

<210> SEQ ID NO 430
<211> LENGTH: 9
<212> TYPE: PRT
<213> ORGANISM: Homo sapiens

<400> SEQUENCE: 430

Thr Tyr Asp Ser Val Thr Asp Lys Phe
1               5

<210> SEQ ID NO 431
<211> LENGTH: 9
<212> TYPE: PRT
<213> ORGANISM: Homo sapiens

<400> SEQUENCE: 431

Ala Glu Ser Leu Tyr Glu Ile Arg Phe
1               5

<210> SEQ ID NO 432
<211> LENGTH: 10
<212> TYPE: PRT
<213> ORGANISM: Homo sapiens

<400> SEQUENCE: 432

Asp Glu Phe Leu Gly Leu Thr His Thr Tyr
1               5                   10

<210> SEQ ID NO 433
<211> LENGTH: 13
<212> TYPE: PRT
<213> ORGANISM: Homo sapiens

<400> SEQUENCE: 433

Ala Leu Asp Phe Phe Gly Asn Gly Pro Pro Val Asn Tyr
1               5                   10

<210> SEQ ID NO 434
<211> LENGTH: 15

-continued

```
<212> TYPE: PRT
<213> ORGANISM: Homo sapiens

<400> SEQUENCE: 434

Ala Leu Asp Phe Phe Gly Asn Gly Pro Pro Val Asn Tyr Lys Thr
1               5                   10                  15

<210> SEQ ID NO 435
<211> LENGTH: 12
<212> TYPE: PRT
<213> ORGANISM: Homo sapiens

<400> SEQUENCE: 435

Asp Phe Phe Gly Asn Gly Pro Pro Val Asn Tyr Lys
1               5                   10

<210> SEQ ID NO 436
<211> LENGTH: 13
<212> TYPE: PRT
<213> ORGANISM: Homo sapiens

<400> SEQUENCE: 436

Asp Phe Phe Gly Asn Gly Pro Pro Val Asn Tyr Lys Thr
1               5                   10

<210> SEQ ID NO 437
<211> LENGTH: 15
<212> TYPE: PRT
<213> ORGANISM: Homo sapiens

<400> SEQUENCE: 437

Asp Phe Phe Gly Asn Gly Pro Pro Val Asn Tyr Lys Thr Gly Asn
1               5                   10                  15

<210> SEQ ID NO 438
<211> LENGTH: 16
<212> TYPE: PRT
<213> ORGANISM: Homo sapiens

<400> SEQUENCE: 438

Asp Phe Phe Gly Asn Gly Pro Pro Val Asn Tyr Lys Thr Gly Asn Leu
1               5                   10                  15

<210> SEQ ID NO 439
<211> LENGTH: 17
<212> TYPE: PRT
<213> ORGANISM: Homo sapiens

<400> SEQUENCE: 439

Asp Phe Phe Gly Asn Gly Pro Pro Val Asn Tyr Lys Thr Gly Asn Leu
1               5                   10                  15

Tyr

<210> SEQ ID NO 440
<211> LENGTH: 19
<212> TYPE: PRT
<213> ORGANISM: Homo sapiens

<400> SEQUENCE: 440

Leu Gln Ala Leu Asp Phe Phe Gly Asn Gly Pro Pro Val Asn Tyr Lys
1               5                   10                  15

Thr Gly Asn
```

```
<210> SEQ ID NO 441
<211> LENGTH: 15
<212> TYPE: PRT
<213> ORGANISM: Homo sapiens

<400> SEQUENCE: 441

Gln Ala Leu Asp Phe Phe Gly Asn Gly Pro Pro Val Asn Tyr Lys
1               5                   10                  15

<210> SEQ ID NO 442
<211> LENGTH: 16
<212> TYPE: PRT
<213> ORGANISM: Homo sapiens

<400> SEQUENCE: 442

Gln Pro Pro His Glu Tyr Val Pro Trp Val Thr Val Asn Gly Lys Pro
1               5                   10                  15

<210> SEQ ID NO 443
<211> LENGTH: 20
<212> TYPE: PRT
<213> ORGANISM: Homo sapiens

<400> SEQUENCE: 443

Ser Pro Leu Gln Ala Leu Asp Phe Phe Gly Asn Gly Pro Pro Val Asn
1               5                   10                  15

Tyr Lys Thr Gly
            20

<210> SEQ ID NO 444
<211> LENGTH: 21
<212> TYPE: PRT
<213> ORGANISM: Homo sapiens

<400> SEQUENCE: 444

Ser Pro Leu Gln Ala Leu Asp Phe Phe Gly Asn Gly Pro Pro Val Asn
1               5                   10                  15

Tyr Lys Thr Gly Asn
            20

<210> SEQ ID NO 445
<211> LENGTH: 23
<212> TYPE: PRT
<213> ORGANISM: Homo sapiens

<400> SEQUENCE: 445

Ser Pro Leu Gln Ala Leu Asp Phe Phe Gly Asn Gly Pro Pro Val Asn
1               5                   10                  15

Tyr Lys Thr Gly Asn Leu Tyr
            20

<210> SEQ ID NO 446
<211> LENGTH: 15
<212> TYPE: PRT
<213> ORGANISM: Homo sapiens

<400> SEQUENCE: 446

Gly Pro Pro Phe Ser Ser Ser Gln Ser Ile Pro Val Val Pro Arg
1               5                   10                  15

<210> SEQ ID NO 447
<211> LENGTH: 14
<212> TYPE: PRT
<213> ORGANISM: Homo sapiens
```

-continued

```
<400> SEQUENCE: 447

Leu Pro Ser Ser Leu Met Asn Asn Leu Pro Ala His Asp Met
1               5                   10

<210> SEQ ID NO 448
<211> LENGTH: 15
<212> TYPE: PRT
<213> ORGANISM: Homo sapiens

<400> SEQUENCE: 448

Leu Pro Ser Ser Leu Met Asn Asn Leu Pro Ala His Asp Met Glu
1               5                   10                  15

<210> SEQ ID NO 449
<211> LENGTH: 16
<212> TYPE: PRT
<213> ORGANISM: Homo sapiens

<400> SEQUENCE: 449

Leu Pro Ser Ser Leu Met Asn Asn Leu Pro Ala His Asp Met Glu Leu
1               5                   10                  15

<210> SEQ ID NO 450
<211> LENGTH: 17
<212> TYPE: PRT
<213> ORGANISM: Homo sapiens

<400> SEQUENCE: 450

Ser Pro Ile Gly Glu Ile Gln Pro Leu Ser Pro Gln Pro Ser Ala Pro
1               5                   10                  15

Ile

<210> SEQ ID NO 451
<211> LENGTH: 17
<212> TYPE: PRT
<213> ORGANISM: Homo sapiens

<400> SEQUENCE: 451

Asp Glu Val Thr Gln Pro Phe Val Ile Asp Glu Lys Thr Ala Glu Ile
1               5                   10                  15

Arg

<210> SEQ ID NO 452
<211> LENGTH: 18
<212> TYPE: PRT
<213> ORGANISM: Homo sapiens

<400> SEQUENCE: 452

Lys Tyr Pro Glu Leu Val Leu Asp Lys Ala Leu Asp Arg Glu Glu Arg
1               5                   10                  15

Pro Glu

<210> SEQ ID NO 453
<211> LENGTH: 15
<212> TYPE: PRT
<213> ORGANISM: Homo sapiens

<400> SEQUENCE: 453

Val Thr Gln Pro Phe Val Ile Asp Glu Lys Thr Ala Glu Ile Arg
1               5                   10                  15
```

<210> SEQ ID NO 454
<211> LENGTH: 17
<212> TYPE: PRT
<213> ORGANISM: Homo sapiens

<400> SEQUENCE: 454

Asp Gly Arg Thr Ile Val Asp Leu Glu Gly Thr Pro Val Val Ser Pro
1               5                   10                  15

Asp

<210> SEQ ID NO 455
<211> LENGTH: 18
<212> TYPE: PRT
<213> ORGANISM: Homo sapiens

<400> SEQUENCE: 455

Asp Gly Arg Thr Ile Val Asp Leu Glu Gly Thr Pro Val Val Ser Pro
1               5                   10                  15

Asp Gly

<210> SEQ ID NO 456
<211> LENGTH: 14
<212> TYPE: PRT
<213> ORGANISM: Homo sapiens

<400> SEQUENCE: 456

Asp Lys Pro Ile Leu Ser Leu Gly Gly Lys Pro Leu Val Gly
1               5                   10

<210> SEQ ID NO 457
<211> LENGTH: 18
<212> TYPE: PRT
<213> ORGANISM: Homo sapiens

<400> SEQUENCE: 457

Gly Asp Gly Arg Thr Ile Val Asp Leu Glu Gly Thr Pro Val Val Ser
1               5                   10                  15

Pro Asp

<210> SEQ ID NO 458
<211> LENGTH: 19
<212> TYPE: PRT
<213> ORGANISM: Homo sapiens

<400> SEQUENCE: 458

Gly Asp Gly Arg Thr Ile Val Asp Leu Glu Gly Thr Pro Val Val Ser
1               5                   10                  15

Pro Asp Gly

<210> SEQ ID NO 459
<211> LENGTH: 19
<212> TYPE: PRT
<213> ORGANISM: Homo sapiens

<400> SEQUENCE: 459

Gly Gly Asp Gly Arg Thr Ile Val Asp Leu Glu Gly Thr Pro Val Val
1               5                   10                  15

Ser Pro Asp

<210> SEQ ID NO 460
<211> LENGTH: 20
<212> TYPE: PRT

-continued

<213> ORGANISM: Homo sapiens

<400> SEQUENCE: 460

Gly Gly Asp Gly Arg Thr Ile Val Asp Leu Glu Gly Thr Pro Val Val
1               5                   10                  15

Ser Pro Asp Gly
        20

<210> SEQ ID NO 461
<211> LENGTH: 11
<212> TYPE: DNA
<213> ORGANISM: Homo sapiens

<400> SEQUENCE: 461
grtvdgtvvs d                                                          11

<210> SEQ ID NO 462
<211> LENGTH: 16
<212> TYPE: PRT
<213> ORGANISM: Homo sapiens

<400> SEQUENCE: 462

Lys Val Lys Glu Tyr Ile Leu Ser Tyr Ala Pro Ala Leu Lys Pro Phe
1               5                   10                  15

<210> SEQ ID NO 463
<211> LENGTH: 17
<212> TYPE: PRT
<213> ORGANISM: Homo sapiens

<400> SEQUENCE: 463

Lys Val Lys Glu Tyr Ile Leu Ser Tyr Ala Pro Ala Leu Lys Pro Phe
1               5                   10                  15

Gly

<210> SEQ ID NO 464
<211> LENGTH: 21
<212> TYPE: PRT
<213> ORGANISM: Homo sapiens

<400> SEQUENCE: 464

Leu Gly Gly Asp Gly Arg Thr Ile Val Asp Leu Glu Gly Thr Pro Val
1               5                   10                  15

Val Ser Pro Asp Gly
            20

<210> SEQ ID NO 465
<211> LENGTH: 15
<212> TYPE: PRT
<213> ORGANISM: Homo sapiens

<400> SEQUENCE: 465

Arg Thr His Glu Ile Lys Lys Leu Ala Ser Glu Ser Val Tyr Val
1               5                   10                  15

<210> SEQ ID NO 466
<211> LENGTH: 15
<212> TYPE: PRT
<213> ORGANISM: Homo sapiens

<400> SEQUENCE: 466

Val Lys Glu Tyr Ile Leu Ser Tyr Ala Pro Ala Leu Lys Pro Phe
1               5                   10                  15

<210> SEQ ID NO 467
<211> LENGTH: 19
<212> TYPE: PRT
<213> ORGANISM: Homo sapiens

<400> SEQUENCE: 467

Tyr Ser Lys Thr Gln Tyr Asn Gln Val Pro Ser Glu Asp Phe Glu Arg
1               5                   10                  15

Thr Pro Gln

<210> SEQ ID NO 468
<211> LENGTH: 16
<212> TYPE: PRT
<213> ORGANISM: Homo sapiens

<400> SEQUENCE: 468

Ala Ala Pro Asn Leu Ser Arg Met Gly Ala Ile Pro Val Met Ile Pro
1               5                   10                  15

<210> SEQ ID NO 469
<211> LENGTH: 17
<212> TYPE: PRT
<213> ORGANISM: Homo sapiens

<400> SEQUENCE: 469

Ala Ala Pro Asn Leu Ser Arg Met Gly Ala Ile Pro Val Met Ile Pro
1               5                   10                  15

Ala

<210> SEQ ID NO 470
<211> LENGTH: 15
<212> TYPE: PRT
<213> ORGANISM: Homo sapiens

<400> SEQUENCE: 470

Ala Pro Asn Leu Ser Arg Met Gly Ala Ile Pro Val Met Ile Pro
1               5                   10                  15

<210> SEQ ID NO 471
<211> LENGTH: 16
<212> TYPE: PRT
<213> ORGANISM: Homo sapiens

<400> SEQUENCE: 471

Ala Pro Asn Leu Ser Arg Met Gly Ala Ile Pro Val Met Ile Pro Ala
1               5                   10                  15

<210> SEQ ID NO 472
<211> LENGTH: 20
<212> TYPE: PRT
<213> ORGANISM: Homo sapiens

<400> SEQUENCE: 472

Gly Tyr Ser Lys Thr Gln Tyr Asn Gln Val Pro Ser Glu Asp Phe Glu
1               5                   10                  15

Arg Thr Pro Gln
            20

<210> SEQ ID NO 473
<211> LENGTH: 15
<212> TYPE: PRT
<213> ORGANISM: Homo sapiens

<400> SEQUENCE: 473

Ser Lys Thr Gln Tyr Asn Gln Val Pro Ser Glu Asp Phe Glu Arg
1               5                   10                  15

<210> SEQ ID NO 474
<211> LENGTH: 17
<212> TYPE: PRT
<213> ORGANISM: Homo sapiens

<400> SEQUENCE: 474

Ser Lys Thr Gln Tyr Asn Gln Val Pro Ser Glu Asp Phe Glu Arg Thr
1               5                   10                  15

Pro

<210> SEQ ID NO 475
<211> LENGTH: 18
<212> TYPE: PRT
<213> ORGANISM: Homo sapiens

<400> SEQUENCE: 475

Ser Lys Thr Gln Tyr Asn Gln Val Pro Ser Glu Asp Phe Glu Arg Thr
1               5                   10                  15

Pro Gln

<210> SEQ ID NO 476
<211> LENGTH: 18
<212> TYPE: PRT
<213> ORGANISM: Homo sapiens

<400> SEQUENCE: 476

Val Ala Ala Pro Asn Leu Ser Arg Met Gly Ala Ile Pro Val Met Ile
1               5                   10                  15

Pro Ala

<210> SEQ ID NO 477
<211> LENGTH: 12
<212> TYPE: PRT
<213> ORGANISM: Homo sapiens

<400> SEQUENCE: 477

Val Ile Ile Leu Tyr Ser Gly Asp Lys Ile Tyr Asp
1               5                   10

<210> SEQ ID NO 478
<211> LENGTH: 16
<212> TYPE: PRT
<213> ORGANISM: Homo sapiens

<400> SEQUENCE: 478

Tyr Ser Lys Thr Gln Tyr Asn Gln Val Pro Ser Glu Asp Phe Glu Arg
1               5                   10                  15

<210> SEQ ID NO 479
<211> LENGTH: 16
<212> TYPE: PRT
<213> ORGANISM: Homo sapiens

<400> SEQUENCE: 479

Lys Tyr Pro Glu Leu Val Leu Asp Lys Ala Leu Asp Arg Glu Glu Arg
1               5                   10                  15

```
<210> SEQ ID NO 480
<211> LENGTH: 12
<212> TYPE: PRT
<213> ORGANISM: Homo sapiens

<400> SEQUENCE: 480

Gly His Leu Phe Ala Leu Arg Ser Leu Asp Tyr Glu
1               5                   10

<210> SEQ ID NO 481
<211> LENGTH: 16
<212> TYPE: PRT
<213> ORGANISM: Homo sapiens

<400> SEQUENCE: 481

Ala Ala Glu Pro Gly Tyr Leu Val Thr Lys Val Val Ala Val Asp Gly
1               5                   10                  15

<210> SEQ ID NO 482
<211> LENGTH: 17
<212> TYPE: PRT
<213> ORGANISM: Homo sapiens

<400> SEQUENCE: 482

Ala Ala Glu Pro Gly Tyr Leu Val Thr Lys Val Val Ala Val Asp Gly
1               5                   10                  15

Asp

<210> SEQ ID NO 483
<211> LENGTH: 18
<212> TYPE: PRT
<213> ORGANISM: Homo sapiens

<400> SEQUENCE: 483

Ala Ala Glu Pro Gly Tyr Leu Val Thr Lys Val Val Ala Val Asp Gly
1               5                   10                  15

Asp Ser

<210> SEQ ID NO 484
<211> LENGTH: 19
<212> TYPE: PRT
<213> ORGANISM: Homo sapiens

<400> SEQUENCE: 484

Ala Ala Glu Pro Gly Tyr Leu Val Thr Lys Val Val Ala Val Asp Gly
1               5                   10                  15

Asp Ser Gly

<210> SEQ ID NO 485
<211> LENGTH: 15
<212> TYPE: PRT
<213> ORGANISM: Homo sapiens

<400> SEQUENCE: 485

Ala Glu Pro Gly Tyr Leu Val Thr Lys Val Val Ala Val Asp Gly
1               5                   10                  15

<210> SEQ ID NO 486
<211> LENGTH: 16
<212> TYPE: PRT
<213> ORGANISM: Homo sapiens

<400> SEQUENCE: 486
```

```
Ala Glu Pro Gly Tyr Leu Val Thr Lys Val Val Ala Val Asp Gly Asp
1               5                   10                  15
```

<210> SEQ ID NO 487
<211> LENGTH: 17
<212> TYPE: PRT
<213> ORGANISM: Homo sapiens

<400> SEQUENCE: 487

```
Ala Glu Pro Gly Tyr Leu Val Thr Lys Val Val Ala Val Asp Gly Asp
1               5                   10                  15

Ser
```

<210> SEQ ID NO 488
<211> LENGTH: 14
<212> TYPE: PRT
<213> ORGANISM: Homo sapiens

<400> SEQUENCE: 488

```
Glu Pro Gly Tyr Leu Val Thr Lys Val Val Ala Val Asp Gly
1               5                   10
```

<210> SEQ ID NO 489
<211> LENGTH: 15
<212> TYPE: PRT
<213> ORGANISM: Homo sapiens

<400> SEQUENCE: 489

```
Glu Pro Gly Tyr Leu Val Thr Lys Val Val Ala Val Asp Gly Asp
1               5                   10                  15
```

<210> SEQ ID NO 490
<211> LENGTH: 16
<212> TYPE: PRT
<213> ORGANISM: Homo sapiens

<400> SEQUENCE: 490

```
Glu Pro Gly Tyr Leu Val Thr Lys Val Val Ala Val Asp Gly Asp Ser
1               5                   10                  15
```

<210> SEQ ID NO 491
<211> LENGTH: 14
<212> TYPE: PRT
<213> ORGANISM: Homo sapiens

<400> SEQUENCE: 491

```
Ala Glu Pro Gly Tyr Leu Val Thr Lys Val Val Ala Val Asp
1               5                   10
```

<210> SEQ ID NO 492
<211> LENGTH: 16
<212> TYPE: PRT
<213> ORGANISM: Homo sapiens

<400> SEQUENCE: 492

```
Ala Asp Ser Thr Glu Phe Arg Pro Asn Ala Pro Val Pro Leu Val Ile
1               5                   10                  15
```

<210> SEQ ID NO 493
<211> LENGTH: 17
<212> TYPE: PRT
<213> ORGANISM: Homo sapiens

<400> SEQUENCE: 493

Ala Asp Ser Thr Glu Phe Arg Pro Asn Ala Pro Val Pro Leu Val Ile
1               5                   10                  15

Asp

<210> SEQ ID NO 494
<211> LENGTH: 17
<212> TYPE: PRT
<213> ORGANISM: Homo sapiens

<400> SEQUENCE: 494

Asp Ala Asp Ser Thr Glu Phe Arg Pro Asn Ala Pro Val Pro Leu Val
1               5                   10                  15

Ile

<210> SEQ ID NO 495
<211> LENGTH: 18
<212> TYPE: PRT
<213> ORGANISM: Homo sapiens

<400> SEQUENCE: 495

Asp Ala Asp Ser Thr Glu Phe Arg Pro Asn Ala Pro Val Pro Leu Val
1               5                   10                  15

Ile Asp

<210> SEQ ID NO 496
<211> LENGTH: 19
<212> TYPE: PRT
<213> ORGANISM: Homo sapiens

<400> SEQUENCE: 496

Asp Ala Asp Ser Thr Glu Phe Arg Pro Asn Ala Pro Val Pro Leu Val
1               5                   10                  15

Ile Asp Met

<210> SEQ ID NO 497
<211> LENGTH: 20
<212> TYPE: PRT
<213> ORGANISM: Homo sapiens

<400> SEQUENCE: 497

Asp Ala Asp Ser Thr Glu Phe Arg Pro Asn Ala Pro Val Pro Leu Val
1               5                   10                  15

Ile Asp Met Pro
            20

<210> SEQ ID NO 498
<211> LENGTH: 21
<212> TYPE: PRT
<213> ORGANISM: Homo sapiens

<400> SEQUENCE: 498

Asp Ala Asp Ser Thr Glu Phe Arg Pro Asn Ala Pro Val Pro Leu Val
1               5                   10                  15

Ile Asp Met Pro Glu
            20

<210> SEQ ID NO 499
<211> LENGTH: 13
<212> TYPE: PRT
<213> ORGANISM: Homo sapiens

<400> SEQUENCE: 499

Asp Ser Thr Glu Phe Arg Pro Asn Ala Pro Val Pro Leu
1               5                   10

<210> SEQ ID NO 500
<211> LENGTH: 14
<212> TYPE: PRT
<213> ORGANISM: Homo sapiens

<400> SEQUENCE: 500

Asp Ser Thr Glu Phe Arg Pro Asn Ala Pro Val Pro Leu Val
1               5                   10

<210> SEQ ID NO 501
<211> LENGTH: 15
<212> TYPE: PRT
<213> ORGANISM: Homo sapiens

<400> SEQUENCE: 501

Asp Ser Thr Glu Phe Arg Pro Asn Ala Pro Val Pro Leu Val Ile
1               5                   10                  15

<210> SEQ ID NO 502
<211> LENGTH: 16
<212> TYPE: PRT
<213> ORGANISM: Homo sapiens

<400> SEQUENCE: 502

Asp Ser Thr Glu Phe Arg Pro Asn Ala Pro Val Pro Leu Val Ile Asp
1               5                   10                  15

<210> SEQ ID NO 503
<211> LENGTH: 18
<212> TYPE: PRT
<213> ORGANISM: Homo sapiens

<400> SEQUENCE: 503

Asp Ser Thr Glu Phe Arg Pro Asn Ala Pro Val Pro Leu Val Ile Asp
1               5                   10                  15

Met Pro

<210> SEQ ID NO 504
<211> LENGTH: 19
<212> TYPE: PRT
<213> ORGANISM: Homo sapiens

<400> SEQUENCE: 504

Asp Ser Thr Glu Phe Arg Pro Asn Ala Pro Val Pro Leu Val Ile Asp
1               5                   10                  15

Met Pro Glu

<210> SEQ ID NO 505
<211> LENGTH: 19
<212> TYPE: PRT
<213> ORGANISM: Homo sapiens

<400> SEQUENCE: 505

Lys Asp Ala Asp Ser Thr Glu Phe Arg Pro Asn Ala Pro Val Pro Leu
1               5                   10                  15

Val Ile Asp

<210> SEQ ID NO 506
<211> LENGTH: 12

```
<212> TYPE: PRT
<213> ORGANISM: Homo sapiens

<400> SEQUENCE: 506

Ser Thr Glu Phe Arg Pro Asn Ala Pro Val Pro Leu
1               5                   10

<210> SEQ ID NO 507
<211> LENGTH: 14
<212> TYPE: PRT
<213> ORGANISM: Homo sapiens

<400> SEQUENCE: 507

Ser Thr Glu Phe Arg Pro Asn Ala Pro Val Pro Leu Val Ile
1               5                   10

<210> SEQ ID NO 508
<211> LENGTH: 15
<212> TYPE: PRT
<213> ORGANISM: Homo sapiens

<400> SEQUENCE: 508

Ser Thr Glu Phe Arg Pro Asn Ala Pro Val Pro Leu Val Ile Asp
1               5                   10                  15

<210> SEQ ID NO 509
<211> LENGTH: 17
<212> TYPE: PRT
<213> ORGANISM: Homo sapiens

<400> SEQUENCE: 509

Ser Thr Glu Phe Arg Pro Asn Ala Pro Val Pro Leu Val Ile Asp Met
1               5                   10                  15

Pro

<210> SEQ ID NO 510
<211> LENGTH: 15
<212> TYPE: PRT
<213> ORGANISM: Homo sapiens

<400> SEQUENCE: 510

Ala Gly Asp Tyr Thr Ile Ala Asn Ala Arg Lys Leu Ile Asp Glu
1               5                   10                  15

<210> SEQ ID NO 511
<211> LENGTH: 9
<212> TYPE: PRT
<213> ORGANISM: Homo sapiens

<400> SEQUENCE: 511

Glu Thr Leu Glu Arg Leu Gln Glu Leu
1               5

<210> SEQ ID NO 512
<211> LENGTH: 15
<212> TYPE: PRT
<213> ORGANISM: Homo sapiens

<400> SEQUENCE: 512

Ala Asp Ile Thr Tyr Ala Ile Glu Ala Asp Ser Glu Ser Val Lys
1               5                   10                  15

<210> SEQ ID NO 513
<211> LENGTH: 14
```

```
<212> TYPE: PRT
<213> ORGANISM: Homo sapiens

<400> SEQUENCE: 513

Asp Ile Thr Tyr Ala Ile Glu Ala Asp Ser Glu Ser Val Lys
1               5                   10

<210> SEQ ID NO 514
<211> LENGTH: 16
<212> TYPE: PRT
<213> ORGANISM: Homo sapiens

<400> SEQUENCE: 514

Lys Arg Asp Asn Tyr Gln Ile Lys Val Val Ala Ser Asp His Gly Glu
1               5                   10                  15

<210> SEQ ID NO 515
<211> LENGTH: 17
<212> TYPE: PRT
<213> ORGANISM: Homo sapiens

<400> SEQUENCE: 515

Lys Arg Asp Asn Tyr Gln Ile Lys Val Val Ala Ser Asp His Gly Glu
1               5                   10                  15

Lys

<210> SEQ ID NO 516
<211> LENGTH: 15
<212> TYPE: PRT
<213> ORGANISM: Homo sapiens

<400> SEQUENCE: 516

Arg Asp Glu Ser Phe Val Ile Asp Arg Gln Ser Gly Arg Leu Lys
1               5                   10                  15

<210> SEQ ID NO 517
<211> LENGTH: 15
<212> TYPE: PRT
<213> ORGANISM: Homo sapiens

<400> SEQUENCE: 517

Arg Asp Asn Tyr Gln Ile Lys Val Val Ala Ser Asp His Gly Glu
1               5                   10                  15

<210> SEQ ID NO 518
<211> LENGTH: 15
<212> TYPE: PRT
<213> ORGANISM: Homo sapiens

<400> SEQUENCE: 518

Ser Pro Ser Glu Leu Asp Arg Asp Pro Ala Tyr Ala Ile Val Thr
1               5                   10                  15

<210> SEQ ID NO 519
<211> LENGTH: 17
<212> TYPE: PRT
<213> ORGANISM: Homo sapiens

<400> SEQUENCE: 519

Thr Pro Pro Gln Phe Ser Ser Val Lys Val Ile His Val Thr Ser Pro
1               5                   10                  15

Gln
```

```
<210> SEQ ID NO 520
<211> LENGTH: 12
<212> TYPE: PRT
<213> ORGANISM: Homo sapiens

<400> SEQUENCE: 520

Val Pro Leu Pro Asp Ile Gln Glu Phe Pro Asn Tyr
1               5                   10

<210> SEQ ID NO 521
<211> LENGTH: 15
<212> TYPE: PRT
<213> ORGANISM: Homo sapiens

<400> SEQUENCE: 521

Gly Pro Gln Leu Phe His Met Asp Pro Ser Gly Thr Phe Val Gln
1               5                   10                  15

<210> SEQ ID NO 522
<211> LENGTH: 17
<212> TYPE: PRT
<213> ORGANISM: Homo sapiens

<400> SEQUENCE: 522

Asp Lys Asn Tyr Phe Glu Gly Thr Gly Tyr Ala Arg Val Pro Thr Gln
1               5                   10                  15
Pro

<210> SEQ ID NO 523
<211> LENGTH: 18
<212> TYPE: PRT
<213> ORGANISM: Homo sapiens

<400> SEQUENCE: 523

Asp Lys Asn Tyr Phe Glu Gly Thr Gly Tyr Ala Arg Val Pro Thr Gln
1               5                   10                  15
Pro His

<210> SEQ ID NO 524
<211> LENGTH: 15
<212> TYPE: PRT
<213> ORGANISM: Homo sapiens

<400> SEQUENCE: 524

Asp Ser Lys Pro Leu Tyr Thr Pro Ser Ser Phe Gly Val Ser
1               5                   10                  15

<210> SEQ ID NO 525
<211> LENGTH: 16
<212> TYPE: PRT
<213> ORGANISM: Homo sapiens

<400> SEQUENCE: 525

Ile Gln Arg Gln Val Lys Glu Ile Asn Ser Leu Gln Ser Asp Phe Thr
1               5                   10                  15

<210> SEQ ID NO 526
<211> LENGTH: 14
<212> TYPE: PRT
<213> ORGANISM: Homo sapiens

<400> SEQUENCE: 526

Lys Asn Tyr Phe Glu Gly Thr Gly Tyr Ala Arg Val Pro Thr
1               5                   10
```

<210> SEQ ID NO 527
<211> LENGTH: 16
<212> TYPE: PRT
<213> ORGANISM: Homo sapiens

<400> SEQUENCE: 527

Lys Asn Tyr Phe Glu Gly Thr Gly Tyr Ala Arg Val Pro Thr Gln Pro
1               5                   10                  15

<210> SEQ ID NO 528
<211> LENGTH: 17
<212> TYPE: PRT
<213> ORGANISM: Homo sapiens

<400> SEQUENCE: 528

Lys Asn Tyr Phe Glu Gly Thr Gly Tyr Ala Arg Val Pro Thr Gln Pro
1               5                   10                  15

His

<210> SEQ ID NO 529
<211> LENGTH: 16
<212> TYPE: PRT
<213> ORGANISM: Homo sapiens

<400> SEQUENCE: 529

Ser Pro Arg Val Val Pro Asn Glu Ser Ile Pro Ile Ile Pro Ile Pro
1               5                   10                  15

<210> SEQ ID NO 530
<211> LENGTH: 17
<212> TYPE: PRT
<213> ORGANISM: Homo sapiens

<400> SEQUENCE: 530

Ser Pro Arg Val Val Pro Asn Glu Ser Ile Pro Ile Ile Pro Ile Pro
1               5                   10                  15

Asp

<210> SEQ ID NO 531
<211> LENGTH: 15
<212> TYPE: PRT
<213> ORGANISM: Homo sapiens

<400> SEQUENCE: 531

Ser Ser Pro Arg Val Val Pro Asn Glu Ser Ile Pro Ile Ile Pro
1               5                   10                  15

<210> SEQ ID NO 532
<211> LENGTH: 17
<212> TYPE: PRT
<213> ORGANISM: Homo sapiens

<400> SEQUENCE: 532

Ser Ser Pro Arg Val Val Pro Asn Glu Ser Ile Pro Ile Ile Pro Ile
1               5                   10                  15

Pro

<210> SEQ ID NO 533
<211> LENGTH: 18
<212> TYPE: PRT
<213> ORGANISM: Homo sapiens

```
<400> SEQUENCE: 533

Ser Ser Pro Arg Val Val Pro Asn Glu Ser Ile Pro Ile Ile Pro Ile
1               5                   10                  15

Pro Asp

<210> SEQ ID NO 534
<211> LENGTH: 16
<212> TYPE: PRT
<213> ORGANISM: Homo sapiens

<400> SEQUENCE: 534

Asp Asp Lys Gly Tyr Thr Leu Met His Pro Ser Leu Thr Arg Pro Tyr
1               5                   10                  15

<210> SEQ ID NO 535
<211> LENGTH: 17
<212> TYPE: PRT
<213> ORGANISM: Homo sapiens

<400> SEQUENCE: 535

Asp Val Gly Gly Ala Gly Tyr Val Val Thr Ile Ser His Thr Ile His
1               5                   10                  15

Ser

<210> SEQ ID NO 536
<211> LENGTH: 13
<212> TYPE: PRT
<213> ORGANISM: Homo sapiens

<400> SEQUENCE: 536

Gly Ala Gly Tyr Val Val Thr Ile Ser His Thr Ile His
1               5                   10

<210> SEQ ID NO 537
<211> LENGTH: 14
<212> TYPE: PRT
<213> ORGANISM: Homo sapiens

<400> SEQUENCE: 537

Gly Ala Gly Tyr Val Val Thr Ile Ser His Thr Ile His Ser
1               5                   10

<210> SEQ ID NO 538
<211> LENGTH: 14
<212> TYPE: PRT
<213> ORGANISM: Homo sapiens

<400> SEQUENCE: 538

Gly Gly Ala Gly Tyr Val Val Thr Ile Ser His Thr Ile His
1               5                   10

<210> SEQ ID NO 539
<211> LENGTH: 15
<212> TYPE: PRT
<213> ORGANISM: Homo sapiens

<400> SEQUENCE: 539

Gly Gly Ala Gly Tyr Val Val Thr Ile Ser His Thr Ile His Ser
1               5                   10                  15

<210> SEQ ID NO 540
<211> LENGTH: 16
<212> TYPE: PRT
```

<213> ORGANISM: Homo sapiens

<400> SEQUENCE: 540

Val Gly Gly Ala Gly Tyr Val Val Thr Ile Ser His Thr Ile His Ser
1               5                   10                  15

<210> SEQ ID NO 541
<211> LENGTH: 18
<212> TYPE: PRT
<213> ORGANISM: Homo sapiens

<400> SEQUENCE: 541

Met Thr Arg Thr Phe His Asp Leu Glu Gly Asn Ala Val Lys Arg Asp
1               5                   10                  15

Ser Gly

<210> SEQ ID NO 542
<211> LENGTH: 13
<212> TYPE: PRT
<213> ORGANISM: Homo sapiens

<400> SEQUENCE: 542

Arg Thr Phe His Asp Leu Glu Gly Asn Ala Val Lys Arg
1               5                   10

<210> SEQ ID NO 543
<211> LENGTH: 16
<212> TYPE: PRT
<213> ORGANISM: Homo sapiens

<400> SEQUENCE: 543

Arg Thr Phe His Asp Leu Glu Gly Asn Ala Val Lys Arg Asp Ser Gly
1               5                   10                  15

<210> SEQ ID NO 544
<211> LENGTH: 15
<212> TYPE: PRT
<213> ORGANISM: Homo sapiens

<400> SEQUENCE: 544

Ser Gly Thr Phe Phe Pro Tyr Ser Ser Asn Pro Ala Asn Pro Lys
1               5                   10                  15

<210> SEQ ID NO 545
<211> LENGTH: 16
<212> TYPE: PRT
<213> ORGANISM: Homo sapiens

<400> SEQUENCE: 545

Ser Gly Thr Phe Phe Pro Tyr Ser Ser Asn Pro Ala Asn Pro Lys Pro
1               5                   10                  15

<210> SEQ ID NO 546
<211> LENGTH: 14
<212> TYPE: PRT
<213> ORGANISM: Homo sapiens

<400> SEQUENCE: 546

Thr Arg Thr Phe His Asp Leu Glu Gly Asn Ala Val Lys Arg
1               5                   10

<210> SEQ ID NO 547
<211> LENGTH: 9
<212> TYPE: PRT

<213> ORGANISM: Homo sapiens

<400> SEQUENCE: 547

Ile Ile Thr Glu Val Ile Thr Arg Leu
1               5

<210> SEQ ID NO 548
<211> LENGTH: 9
<212> TYPE: PRT
<213> ORGANISM: Homo sapiens

<400> SEQUENCE: 548

Lys Met Ile Ser Ala Ile Pro Thr Leu
1               5

<210> SEQ ID NO 549
<211> LENGTH: 9
<212> TYPE: PRT
<213> ORGANISM: Homo sapiens

<400> SEQUENCE: 549

Thr Tyr Ser Glu Lys Thr Thr Leu Phe
1               5

<210> SEQ ID NO 550
<211> LENGTH: 9
<212> TYPE: PRT
<213> ORGANISM: Homo sapiens

<400> SEQUENCE: 550

Ala Leu Leu Pro Ala Val Pro Ser Leu
1               5

<210> SEQ ID NO 551
<211> LENGTH: 9
<212> TYPE: PRT
<213> ORGANISM: Homo sapiens

<400> SEQUENCE: 551

Gly Arg Asn Ser Phe Glu Val Arg Val
1               5

<210> SEQ ID NO 552
<211> LENGTH: 9
<212> TYPE: PRT
<213> ORGANISM: Homo sapiens

<400> SEQUENCE: 552

Arg Pro Ile Leu Thr Ile Ile Thr Leu
1               5

<210> SEQ ID NO 553
<211> LENGTH: 10
<212> TYPE: PRT
<213> ORGANISM: Homo sapiens

<400> SEQUENCE: 553

Thr Tyr Ser Pro Ala Leu Asn Lys Met Phe
1               5                   10

<210> SEQ ID NO 554
<211> LENGTH: 11
<212> TYPE: PRT
<213> ORGANISM: Homo sapiens

```
<400> SEQUENCE: 554

Thr Tyr Leu Pro Thr Asn Ala Ser Leu Ser Phe
1               5                   10

<210> SEQ ID NO 555
<211> LENGTH: 9
<212> TYPE: PRT
<213> ORGANISM: Homo sapiens

<400> SEQUENCE: 555

Gly Val Phe Arg Gly Ile Gln Asp Val
1               5

<210> SEQ ID NO 556
<211> LENGTH: 9
<212> TYPE: PRT
<213> ORGANISM: Homo sapiens

<400> SEQUENCE: 556

Leu Met Ser Val Tyr Val Val Glu Leu
1               5

<210> SEQ ID NO 557
<211> LENGTH: 9
<212> TYPE: PRT
<213> ORGANISM: Homo sapiens

<400> SEQUENCE: 557

Gln Arg Asn Met Thr Lys Leu Gln Leu
1               5

<210> SEQ ID NO 558
<211> LENGTH: 9
<212> TYPE: PRT
<213> ORGANISM: Homo sapiens

<400> SEQUENCE: 558

Arg Met Phe Pro Asn Ala Pro Tyr Leu
1               5

<210> SEQ ID NO 559
<211> LENGTH: 6
<212> TYPE: PRT
<213> ORGANISM: Artificial Sequence
<220> FEATURE:
<223> OTHER INFORMATION: Linker sequence

<400> SEQUENCE: 559

Leu Leu Leu Leu Leu Leu
1               5
```

PEPTIDES AND COMBINATION OF PEPTIDES FOR USE IN IMMUNOTHERAPY AGAINST EPITHELIAL OVARIAN CANCER AND OTHER CANCERS

CROSS REFERENCE TO RELATED APPLICATIONS

This application is a continuation of U.S. application Ser. No. 17/123,585, filed 16 Dec. 2020, which is a continuation of U.S. application Ser. No. 16/905,550, filed 18 Jun. 2020, now U.S. Pat. No. 10,888,587, issued 12 Jan. 2021, which is a continuation of U.S. application Ser. No. 16/777,919, filed 31 Jan. 2020, now U.S. Pat. No. 10,722,538, issued 28 Jul. 2020, which is a continuation of U.S. application Ser. No. 16/556,549, filed 30 Aug. 2019, now U.S. Pat. No. 10,639,331, issued 5 May 2020, which is a continuation of U.S. application Ser. No. 15/813,610, filed 15 Nov. 2017, now U.S. Pat. No. 10,463,696, issued 5 Nov. 2019, which is a continuation of U.S. application Ser. No. 15/209,845, filed 14 Jul. 2016, now U.S. Pat. No. 9,889,159, issued 13 Feb. 2018, which claims the benefit of U.S. Provisional Application Ser. No. 62/192,670, filed 15 Jul. 2015, and Great Britain Application No. 1512369.8, filed 15 Jul. 2015, the content of each of these applications is herein incorporated by reference in their entirety.

This application also is related to PCT/EP2016/066706 filed 14 Jul. 2016, the content of which is incorporated herein by reference in its entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_listing_2912919-052014_ST25.txt" created on 26 Apr. 2021, and 100,163 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I as well as HLA class II molecules of human tumor cells that can be used in vaccine compositions for eliciting anti-tumor immune responses, or as targets for the development of pharmaceutically/immunologically active compounds and cells.

BACKGROUND OF THE INVENTION

Epithelial ovarian cancer (EOC) remains the leading cause of death from gynecologic malignancies and the fifth leading cause of cancer related death in the western world, causing an estimated 22,000 new diagnoses and 14,000 deaths in the US in 2014(1). The only available curative treatment option is complete surgical tumor removal at an early non metastatic stage. However, most patients (>70%) are diagnosed with stage III or IV disease caused by of a lack of specific early symptoms. Despite progress in chemotherapy regimens and the recent approval of bevacizumab for first line therapy, the majority of patients relapse within few months or years after initial treatment (2, 3).

Considering the severe side-effects and expense associated with treating cancer, there is a need to identify factors that can be used in the treatment of cancer in general and ovarian cancer in particular. There is also a need to identify factors representing biomarkers for cancer in general and ovarian cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens. The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

Over the last two decades, EOC has been recognized as a highly immunogenic tumor, based on diverse clinical findings. Showing frequent immune cell infiltration EOC was among the first cancers, where a definitive association of T-cell infiltration and clinical prognosis could be established. Within these infiltrating T-cell population tumor reactive and antigen specific T-cells have been identified. Tumor resident regulatory T-cells (Tregs) in contrast are negatively correlated with clinical outcome. Further, immune stimulatory cytokines have been shown to induce compelling tumor responses in individual patients.

The effectiveness of immunotherapeutic approaches for cancer therapy has been illustrated by the recent development and approval of immune checkpoint inhibitors shown in melanoma treatment. Moreover, antigen specific peptide vaccination and adoptive T-cell transfer begin to show success in melanoma and other immunogenic tumors, e.g. renal cell carcinoma. Personalized immunotherapy even has curative potential and stunning results were presented for individual patients.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 549 or a variant sequence thereof which is at least 77%, preferably at least 88%, homologous (preferably at least 77% or at least 88% identical) to SEQ ID NO: 1 to SEQ ID NO: 549, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 549 or a variant thereof, which is at least 77%, preferably at least 88%, homologous (preferably at least 77% or at least 88% identical) to SEQ ID NO: 1 to SEQ ID NO: 549, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4 are furthermore useful in the diagnosis and/or treatment of various other malignancies that involve an over-expression or over-presentation of the respective underlying polypeptide.

TABLE 1

Peptides according to the present invention;
X = S, R or G

| SEQ ID No. | Sequence | Gene | HLA binding |
|---|---|---|---|
| 1 | QFITSTNTF | MUC16 | A*24:02 |
| 2 | STETSTVLY | MUC16 | A*01 |
| 3 | AHSKITTAM | MUC16 | B*39:01 |
| 4 | AVKTETSTSER | MUC16 | A*31:01 |
| 5 | AVTNVRTSI | MUC16 | B*13 |
| 6 | DALTPLVTI | MUC16 | B*5101 |
| 7 | DALVLKTV | MUC16 | B*51 |
| 8 | DPYKATSAV | MUC16 | B*51 |
| 9 | EPETTTSFITY | MUC16 | B*35 |
| 10 | ERSPVIQTL | MUC16 | B*39:01 |
| 11 | ETILTFHAF | MUC16 | A*25 |
| 12 | EVISSRGTSM | MUC16 | A*25 |
| 13 | EVITSSRTTI | MUC16 | A*25 |
| 14 | EVTSSGRTSI | MUC16 | A*25 |
| 15 | FPEKTTHSF | MUC16 | B*35 |
| 16 | FPHSEETTTM | MUC16 | B*35 |
| 17 | FPHSEITTL | MUC16 | B*35 |

TABLE 1-continued

Peptides according to the present invention; X = S, R or G

| SEQ ID No. | Sequence | Gene | HLA binding |
|---|---|---|---|
| 18 | FQRQGQTAL | MUC16 | B*15:01 |
| 19 | GDVPRPSSL | MUC16 | B*08:01 |
| 20 | GHESHSPAL | MUC16 | B*39:01 |
| 21 | GHTTVSTSM | MUC16 | B*39:01 |
| 22 | GTHSPVTQR | MUC16 | A*31:01 |
| 23 | GTSGTPVSK | MUC16 | A*11 |
| 24 | HPDPQSPGL | MUC16 | B*35 |
| 25 | IPRVFTSSI | MUC16 | B*51 |
| 26 | ISDEVVTRL | MUC16 | C*05 |
| 27 | ISIGTIPRI | MUC16 | B*15:17 |
| 28 | ISKEDVTSI | MUC16 | B*15:17 |
| 29 | ITETSAVLY | MUC16 | A*01 |
| 30 | ITRLPTSSI | MUC16 | B*15:17 |
| 31 | KDTAHTEAM | MUC16 | B*44:02 |
| 32 | KEDSTALVM | MUC16 | B*40/B*44 |
| 33 | KEVTSSSSVL | MUC16 | B*40/B*44/? |
| 34 | LPHSEITTL | MUC16 | B*35 |
| 35 | LTISTHKTI | MUC16 | B*15:17 |
| 36 | LTKSEERTI | MUC16 | B*15:17 |
| 37 | RDSLYVNGF | MUC16 | B*44:02 |
| 38 | RETSTSQKI | MUC16 | B*18:01 |
| 39 | RSSGVTFSR | MUC16 | A*31:01 |
| 40 | SAFESHSTV | MUC16 | B*51 |
| 41 | SATERSASL | MUC16 | C*03/? |
| 42 | SENSETTAL | MUC16 | B*40/B*44/? |
| 43 | SEQRTSPSL | MUC16 | ? |
| 44 | SESPSTIKL | MUC16 | B*40/? |
| 45 | SPAGEAHSL | MUC16 | B*07/B*56 |
| 46 | SPAGEAHSLLA | MUC16 | B*56:01 |
| 47 | SPHPVSTTF | MUC16 | B*07:02 |
| 48 | SPHPVTALL | MUC16 | B*07:02 |
| 49 | SPLFQRSSL | MUC16 | B*0702 |
| 50 | SPQNLRNTL | MUC16 | B*35/B*07:02 |
| 51 | SPRLNTQGNTAL | MUC16 | B*07:02 |
| 52 | SPSEAITRL | MUC16 | B*07:02 |
| 53 | SPSKAFASL | MUC16 | B*35/B*07:02 |
| 54 | SPSSPTPKV | MUC16 | B*07:02 |
| 55 | SPSSQAPVL | MUC16 | B*07:02 |
| 56 | SQGFSHSQM | MUC16 | B*15:01 |
| 57 | SRTEVISSR | MUC16 | B*27 |
| 58 | SSAVSTTTI | MUC16 | B*15:17 |
| 59 | SSPLRVTSL | MUC16 | n/a |
| 60 | STASSSLSK | MUC16 | A*11 |
| 61 | STQRVTTSM | MUC16 | B*07? |
| 62 | STSQEIHSATK | MUC16 | A*11 |
| 63 | SVLADLVTTK | MUC16 | A*03:01 |
| 64 | SVPDILSTSW | MUC16 | A*24:02 |
| 65 | TAGPTTHQF | MUC16 | C*03 |
| 66 | TEISSSRTSI | MUC16 | B*49:01 |
| 67 | TENTGKEKL | MUC16 | B*40/B*44 |
| 68 | TETEAIHVF | MUC16 | B*18 |
| 69 | TEVSRTEVI | MUC16 | B*49:01 |
| 70 | TExVLQGLL | MUC16 | B*40/B*44/? |
| 71 | TPGGTRQSL | MUC16 | B*07:02/B*35 |
| 72 | TPGNRAISL | MUC16 | B*07:02/B*35 |
| 73 | TPNSRGETSL | MUC16 | B*07:02 |
| 74 | TSGPVTEKY | MUC16 | B*35 |
| 75 | TSPAGEAHSL | MUC16 | ? |
| 76 | VHESHSSVL | MUC16 | B*39:01 |
| 77 | VPRSAATTL | MUC16 | B*07:02/B*35 |
| 78 | VTSAPGRSI | MUC16 | B*15:17 |
| 79 | VTSSSRTSI | MUC16 | B*15:17 |
| 80 | YPDPSKASSAM | MUC16 | B*35 |
| 81 | AAWLRSAAA | MMP11 | B*55/B*56 |
| 82 | APAAWLRSAA | MMP11 | B*55/B*56 |
| 83 | APAAWLRSAAA | MMP11 | B*55/B*56 |
| 84 | LPSPVDAAF | MMP11 | B*35 |
| 85 | RGVPSEIDAAF | MMP11 | B*58 |
| 86 | EAGPPAFYR | ESR1 | A*66 |
| 87 | STSSHSLQK | ESR1 | A*03/A*11 |
| 88 | APHLHLSA | KLK10 | B*56:01 |
| 89 | APHLHLSAA | KLK10 | B*56:01 |
| 90 | RALAKLLPL | KLK10 | B*08/A*02 |
| 91 | SAASGARAL | KLK10 | C*03 |

TABLE 1-continued

Peptides according to the present invention; X = S, R or G

| SEQ ID No. | Sequence | Gene | HLA binding |
|---|---|---|---|
| 92 | VLVDQSWVL | KLK10 | A*02 |
| 93 | DYLKRFYLY | MMP7 | A*24 |
| 94 | SETKNANSL | MMP7 | B*44/B*41/B*40 |
| 95 | SSDPNAVMY | MMP7 | A*01 |
| 96 | YPFDGPGNTL | MMP7 | B*35 |
| 97 | YPFDGPGNTLAH | MMP7 | B*35 |
| 98 | NEIERVFVW | EYA2 | B*44:02 |
| 99 | NVGGLIGTPK | EYA2 | A*03 |
| 100 | RVKEMYNTY | EYA2 | A*30/A*32 |
| 101 | SAPLRVSQL | EYA2 | ? |
| 102 | DTDEYVLKY | EFHC1 | A*01 |
| 103 | KDSTKTAF | EFHC1 | B*44 |
| 104 | SKAPVLTY | EFHC1 | B*15:03 |
| 105 | AEYTDVLQKI | EPS8L1 | B*49 |
| 106 | EYTDVLQKI | EPS8L1 | A*24 |
| 107 | RPHLTSDA | EPS8L1 | B*56 |
| 108 | RPHLTSDAV | EPS8L1 | B*56 |
| 109 | RPHLTSDAVA | EPS8L1 | B*56 |
| 110 | SAKSIYEQR | EPS8L1 | A*31 |
| 111 | SPEEGARVY | EPS8L1 | B*35 |
| 112 | SQYPVNHLV | EPS8L1 | B*15 |
| 113 | YPVNHLVTF | EPS8L1 | B*35 |
| 114 | AAASAIKVI | IDO1 | C*12 |
| 115 | IHDHVNPKAFF | IDO1 | B*38 |
| 116 | NPKAFFSVL | IDO1 | B*07 |
| 117 | NPSVREFVL | IDO1 | B*35 |
| 118 | RSYHLQIVTK | IDO1 | A*11/A*03 |
| 119 | RYMPPAHRNF | IDO1 | A*24 |
| 120 | TEFEQYLHF | SOX17 | B*18/B*44 |
| 121 | VSDASSAVYY | SOX17 | A*01 |
| 122 | AEIEADRSY | LAMC2 | B*44 |
| 123 | AQKVDTRAK | LAMC2 | A*03 |
| 124 | HPSAHDVIL | LAMC2 | B*35:03 |
| 125 | RIKQKADSL | LAMC2 | B*08 |
| 126 | SEGASRSLGL | LAMC2 | B*37 |
| 127 | SVDEEGLVLL | LAMC2 | A*02 |
| 128 | SVHKITSTF | LAMC2 | A*25 |
| 129 | TREATQAEI | LAMC2 | B*39 |
| 130 | VYFVAPAKF | LAMC2 | A*24 |
| 131 | APQSAHAAF | SGPL1 | B*07 |
| 132 | ETIIIFHSL | EYA3 | A*25 |
| 133 | TELLVKAY | SGPL1 | B*18 |
| 134 | WQEGRASGTVY | SGPL1 | B*15 |
| 135 | IRSENFEEL | CRABP2 | B*39 |
| 136 | KIAVAAASK | CRABP2 | A*03 |
| 137 | NVMLRKIAV | CRABP2 | B*08 |
| 138 | RELTNDGELIL | CRABP2 | B*40/B*44 |
| 139 | VAAASKPAV | CRABP2 | ? |
| 140 | SPNAIFKAL | SOX9 | B*07 |
| 141 | SSKNKPHVKR | SOX9 | A*31 |
| 142 | TPASAGHVW | SOX9 | B*07 |
| 143 | YTDHQNSSSY | SOX9 | A*01 |
| 144 | AEVLLPRL | MSLN | B*40 |
| 145 | AVLPLTVAEVQK | MSLN | A*03 |
| 146 | LPTARPLL | MSLN | B*07 |
| 147 | RVRELAVAL | MSLN | A*02 |
| 148 | NLPIFLPRV | MLPH | A*02 |
| 149 | RVHPEEQGW | MLPH | B*58 |
| 150 | TVKPSGKPR | MLPH | A*31 |
| 151 | YYEHVKARF | MLPH | A*24 |
| 152 | AARPAGATL | ERBB2 | B*07 |
| 153 | MPNPEGRYTF | ERBB2 | B*35 |
| 154 | FYIKTSTTV | CRABP2 | A*24 |
| 155 | RTTEINFKV | CRABP2 | A*02 |
| 156 | YIKTSTTV | CRABP2 | B*08 |
| 157 | GQAAQGPTI | DDR1 | B*15 |
| 158 | HRFLAEDAL | DDR1 | B*39:01 |
| 159 | EEVARFYAA | FOLR1 | B*45 |
| 160 | NPNEEVARF | FOLR1 | B*35 |
| 161 | NPNEEVARFY | FOLR1 | B*35 |
| 162 | KSQTLLGK | ULK1 | A*11/A*03 |
| 163 | DELISKSF | YPEL1 | B*18 |
| 164 | HDELISKSF | YPEL1 | B*35 |
| 165 | GRAYLFNSV | YPEL1 | B*27 |

TABLE 1-continued

Peptides according to the present invention; X = S, R or G

| SEQ ID No. | Sequence | Gene | HLA binding |
|---|---|---|---|
| 166 | YLFNSVVNV | YPEL1 | A*02 |
| 167 | APDNRPAL | MUC1 | B*07/B*35 |
| 168 | HHSDTPTTL | MUC1 | B*38/B*39 |
| 169 | HPMSEYPTY | MUC1 | B*35 |
| 170 | LQRDISEM | MUC1 | B*51 |
| 171 | LQRDISEMF | MUC1 | B*51 |
| 172 | AIAEIGNQL | MMP9 | A*02 |
| 173 | DVAQVTGALR | MMP9 | A*68 |
| 174 | SEDLPRAVI | MMP9 | B*49/B*40 |
| 175 | APDAKSFVL | LGALS1 | B*35 |
| 176 | EVAPDAKSF | LGALS1 | A*25 |
| 177 | FPFQPGSVAEV | LGALS1 | B*35 |
| 178 | GEVAPDAKSFVL | LGALS1 | B*40 |
| 179 | LPDGYEFKF | LGALS1 | B*35 |

TABLE 2

Additional peptides according to the present invention, X = S, R or G

| SEQ ID No. | Sequence | MHC class | Gene |
|---|---|---|---|
| 180 | DKAFTAATTEVSR | II | MUC16 |
| 181 | ELGPYTLDRNSLYVN | II | MUC16 |
| 182 | ELGPYTLDRNSLYVNG | II | MUC16 |
| 183 | FDKAFTAATTEVSR | II | MUC16 |
| 184 | GPYTLDRNSLYVN | II | MUC16 |
| 185 | LGPYTLDRDSLYVN | II | MUC16 |
| 186 | LGPYTLDRNSLYVN | II | MUC16 |
| 187 | LGPYTLDRNSLYVNG | II | MUC16 |
| 188 | STETITRLSTFPFVTG | II | MUC16 |
| 189 | ELQWEQAQDYLKR | II | MMP7 |
| 190 | ELQWEQAQDYLKRF | II | MMP7 |
| 191 | GINFLYAATHELGHS | II | MMP7 |
| 192 | LQWEQAQDYLKR | II | MMP7 |
| 193 | LQWEQAQDYLKRF | II | MMP7 |
| 194 | SELQWEQAQDYLKR | II | MMP7 |
| 195 | SELQWEQAQDYLKRF | II | MMP7 |
| 196 | VPYNILTPYPGPR | II | EPS8L1 |
| 197 | YVPYNILTPYPGPR | II | EPS8L1 |

TABLE 2-continued

Additional peptides according to the present invention, X = S, R or G

| SEQ ID No. | Sequence | MHC class | Gene |
|---|---|---|---|
| 198 | GNWKIIRSENFEEL | II | CRABP2 |
| 199 | GNWKIIRSENFEELLK | II | CRABP2 |
| 200 | NWKIIRSENFEEL | II | CRABP2 |
| 201 | PNFSGNWKIIRSENF | II | CRABP2 |
| 202 | VMLRKIAVAAASKPA | II | CRABP2 |
| 203 | WKIIRSENFEEL | II | CRABP2 |
| 204 | LQRYSSDPTGALT | II | EGFR |
| 205 | NPTTYQMDVNPEGK | II | EGFR |
| 206 | NPTTYQMDVNPEGKY | II | EGFR |
| 207 | DDGGQFVVTTNPVNNDG | II | CDH1 |
| 208 | DKEGKVFYSITGQGADTPP | II | CDH1 |
| 209 | DKEGKVFYSITGQGADTPPV | II | CDH1 |
| 210 | DKNMFTINRNTGVI | II | CDH1 |
| 211 | DKNMFTINRNTGVIS | II | CDH1 |
| 212 | DPELPDKNMFTINRNTG | II | CDH1 |
| 213 | DPELPDKNMFTINRNTGVI | II | CDH1 |
| 214 | DPELPDKNMFTINRNTGVIS | II | CDH1 |
| 215 | DPELPDKNMFTINRNTGVISV | II | CDH1 |
| 216 | DPELPDKNMFTINRNTGVISVV | II | CDH1 |
| 217 | DPELPDKNMFTINRNTGVISVVT | II | CDH1 |
| 218 | DVNTYNAAIAYTILS | II | CDH1 |
| 219 | DVNTYNAAIAYTILSQ | II | CDH1 |
| 220 | EGKVFYSITGQGADT | II | CDH1 |
| 221 | EGKVFYSITGQGADTPP | II | CDH1 |
| 222 | EGKVFYSITGQGADTPPV | II | CDH1 |
| 223 | ELPDKNMFTINRNTGVIS | II | CDH1 |
| 224 | GGQFVVTTNPVNN | II | CDH1 |
| 225 | GKVFYSITGQGADT | II | CDH1 |
| 226 | GPFPKNLVQIKSNKDK | II | CDH1 |
| 227 | GPFPKNLVQIKSNKDKE | II | CDH1 |
| 228 | GPFPKNLVQIKSNKDKEGK | II | CDH1 |
| 229 | KNMFTINRNTGVI | II | CDH1 |
| 230 | KNMFTINRNTGVIS | II | CDH1 |
| 231 | LPDKNMFTINRNTG | II | CDH1 |
| 232 | LPDKNMFTINRNTGVI | II | CDH1 |
| 233 | LPDKNMFTINRNTGVIS | II | CDH1 |

TABLE 2-continued

Additional peptides according to the present invention, X = S, R or G

| SEQ ID No. | Sequence | MHC class | Gene |
|---|---|---|---|
| 234 | PELPDKNMFTINRNTGVI | II | CDH1 |
| 235 | PELPDKNMFTINRNTGVIS | II | CDH1 |
| 236 | QDPELPDKNMFTINRNTGVIS | II | CDH1 |
| 237 | SQDPELPDKNMFTINRNTGVIS | II | CDH1 |
| 238 | SQDPELPDKNMFTINRNTGVISVVT | II | CDH1 |
| 239 | SVPRYLPRPANPDE | II | CDH1 |
| 240 | TDGVITVKRPLRFHNPQ | II | CDH1 |
| 241 | TRAELDREDFEHVK | II | CDH1 |
| 242 | VPRYLPRPANPDE | II | CDH1 |
| 243 | ALEFRALEPQGLL | II | AGRN |
| 244 | ALEFRALEPQGLLL | II | AGRN |
| 245 | DTRIFFVNPAPPY | II | AGRN |
| 246 | DTRIFFVNPAPPYL | II | AGRN |
| 247 | DTRIFFVNPAPPYLW | II | AGRN |
| 248 | DTRIFFVNPAPPYLWP | II | AGRN |
| 249 | DTRIFFVNPAPPYLWPA | II | AGRN |
| 250 | EFRALEPQGLLL | II | AGRN |
| 251 | GAPVPAFEGRSFLAFPTL | II | AGRN |
| 252 | GDTRIFFVNPAPPYLWP | II | AGRN |
| 253 | GDTRIFFVNPAPPYLWPA | II | AGRN |
| 254 | IVDVHFDPTTAFRAPD | II | AGRN |
| 255 | KVRVWRYLKGKDLVAR | II | AGRN |
| 256 | LALEFRALEPQGLLL | II | AGRN |
| 257 | LEFRALEPQGLLL | II | AGRN |
| 258 | SGPFLADFNGFSH | II | AGRN |
| 259 | TGDTRIFFVNPAPPYLWPA | II | AGRN |
| 260 | TRIFFVNPAPPYL | II | AGRN |
| 261 | VDVHFDPTTAFRAPD | II | AGRN |
| 262 | VDVHFDPTTAFRAPDV | II | AGRN |
| 263 | VRVWRYLKGKDLVAR | II | AGRN |
| 264 | APVPAFEGRSFLAFPT | II | AGRN |
| 265 | APVPAFEGRSFLAFPTL | II | AGRN |
| 266 | ALRGLLPVLGQPIIR | II | MSLN |
| 267 | DLPGRFVAESAEVLLP | II | MSLN |
| 268 | DLPGRFVAESAEVLLPR | II | MSLN |
| 269 | GQPIIRSIPQGIV | II | MSLN |
| 270 | GQPIIRSIPQGIVA | II | MSLN |
| 271 | LGQPIIRSIPQGIVA | II | MSLN |
| 272 | LPAALACWGVRGSL | II | MSLN |
| 273 | LPGRFVAESAEVLL | II | MSLN |
| 274 | LPGRFVAESAEVLLP | II | MSLN |
| 275 | LPGRFVAESAEVLLPR | II | MSLN |
| 276 | LRGLLPVLGQPIIR | II | MSLN |
| 277 | PGRFVAESAEVLLPR | II | MSLN |
| 278 | PGRFVAESAEVLLPRL | II | MSLN |
| 279 | QPIIRSIPQGIVA | II | MSLN |
| 280 | RGLLPVLGQPIIR | II | MSLN |
| 281 | SRTLAGETGQEAAPL | II | MSLN |
| 282 | STERVRELAVALAQK | II | MSLN |
| 283 | TDAVLPLTVAEVQ | II | MSLN |
| 284 | VAEVQKLLGPHVEG | II | MSLN |
| 285 | VAEVQKLLGPHVEGLK | II | MSLN |
| 286 | VLGQPIIRSIPQGIVA | II | MSLN |
| 287 | VRGSLLSEADVRALG | II | MSLN |
| 288 | VRGSLLSEADVRALGG | II | MSLN |
| 289 | LPAALACWGVRGSLL | II | MSLN |
| 290 | AIKVLRENTSPKANKE | II | ERBB2 |
| 291 | DPSPLQRYSEDPTVPLPS | II | ERBB2 |
| 292 | DPSPLQRYSEDPTVPLPSE | II | ERBB2 |
| 293 | ELVSEFSRMARD | II | ERBB2 |
| 294 | ELVSEFSRMARDPQ | II | ERBB2 |
| 295 | IPVAIKVLRENTSPKANKE | II | ERBB2 |
| 296 | RRLLQETELVEPLTPS | II | ERBB2 |
| 297 | SPQPEYVNQPDVRPQPP | II | ERBB2 |
| 298 | VKPDLSYMPIWKFPDE | II | ERBB2 |
| 299 | ASGMRYLATLNFVHR | II | DDR1 |
| 300 | IASGMRYLATLNFVHR | II | DDR1 |
| 301 | KEVKIMSRLKDPN | II | DDR1 |
| 302 | LNQFLSAHQLEDK | II | DDR1 |
| 303 | NPAYRLLLATYARPP | II | DDR1 |
| 304 | NPAYRLLLATYARPPR | II | DDR1 |
| 305 | SNPAYRLLLATYARPP | II | DDR1 |
| 306 | SNPAYRLLLATYARPPR | II | DDR1 |

TABLE 2-continued

Additional peptides according to the present invention, X = S, R or G

| SEQ ID No. | Sequence | MHC class | Gene |
|---|---|---|---|
| 307 | DPSTDYYQELQRDISE | II | MUC1 |
| 308 | VETQFNQYKTEAASR | II | MUC1 |
| 309 | GRQVWVYTGASVLGPR | II | MMP9 |
| 310 | NQLYLFKDGKYWRFSEG | II | MMP9 |
| 311 | RQVWVYTGASVLGPR | II | MMP9 |
| 312 | SGRQVWVYTGASVLG | II | MMP9 |
| 313 | SGRQVWVYTGASVLGP | II | MMP9 |
| 314 | SGRQVWVYTGASVLGPR | II | MMP9 |
| 315 | VDPRSASEVDRMFPG | II | MMP9 |
| 316 | GEVAPDAKSFVLN | II | LGALS1 |
| 317 | LTVKLPDGYEFKFPNRLNL | II | LGALS1 |
| 318 | VRGEVAPDAKSFVLN | II | LGALS1 |
| 319 | VRGEVAPDAKSFVLNLG | II | LGALS1 |

TABLE 3

Additional peptides useful for cancer therapies, X = S, R or G

| SEQ ID No. | Sequence | MHC class | Gene |
|---|---|---|---|
| 320 | ATSKIPLAL | I | MUC16 |
| 321 | ITSSRTTI | I | MUC16 |
| 322 | LNFTITNLQ | I | MUC16 |
| 323 | TATSPMVPAS | I | MUC16 |
| 324 | TTLPESRPS | I | MUC16 |
| 325 | VELRVLALP | I | LRFN4 |
| 326 | AEDNLIHKF | I | NLRP2 |
| 327 | REDLERLGV | I | NLRP7 |
| 328 | DTKDPAVTEW | I | TLR7 |
| 329 | ILISKLLGA | I | TLR7 |
| 330 | SESLRTLEF | I | TLR7 |
| 331 | VLAELVAKL | I | TLR7 |
| 332 | INTSILLIF | I | TLR3 |
| 333 | ALQPLLHTV | I | IL17RD |
| 334 | RLMDNLPQL | I | IL17RD |
| 335 | LIISPTREL | I | DDX10 |
| 336 | ADSKVLLF | I | WDR35 |
| 337 | DSLLEQANNAI | I | WDR35 |
| 338 | DYQGIKFVKR | I | WDR35 |
| 339 | EVVGYFGRF | I | WDR35 |
| 340 | KYVKGLISI | I | WDR35 |
| 341 | SIGTPLDPK | I | WDR35 |
| 342 | TASDKILIV | I | WDR35 |
| 343 | GVIKVISGF | I | NOC3L |
| 344 | KVKLENKLK | I | NOC3L |
| 345 | SSSEPVHAK | I | NOC3L |
| 346 | SSSEPVHAKK | I | NOC3L |
| 347 | LSDQLAQAI | I | DNASE1 |
| 348 | LSDIVIEKY | I | WDR27 |
| 349 | SLDDHVVAV | I | WDR27 |
| 350 | SQIDQQNSV | I | LRIF1 |
| 351 | STIDPSGTRSK | I | LRIF1 |
| 352 | VFRDQEPKI | I | LRIF1 |
| 353 | VLREKEAAL | I | LRIF1 |
| 354 | TRLQQAQAL | I | POLR2J3 |
| 355 | VAAPEHISY | I | POLR2J3 |
| 356 | NSKKKVAL | I | DDX52 |
| 357 | QNSKKKVAL | I | DDX52 |
| 358 | RDNTVHSF | I | DDX52 |
| 359 | KQVSEFMTW | I | RASGEF1B |
| 360 | KTKPQSIQR | I | RASGEF1B |
| 361 | THIELERL | I | RASGEF1B |
| 362 | IAPKILQL | I | RASGEF1B |
| 363 | DIASVSGRW | I | BICC1 |
| 364 | KPKQPSKSV | I | BICC1 |
| 365 | MPAETIKEL | I | BICC1 |
| 366 | SAVKEGTAM | I | BICC1 |
| 367 | EEEKLQAAF | I | COMMD10 |
| 368 | DEFNLQKM | I | EMC1 |
| 369 | DEYKVTAF | I | EMC1 |
| 370 | ETNIGGLNW | I | EMC1 |
| 371 | FPQTALVSF | I | EMC1 |
| 372 | GEFGKKADGLL | I | EMC1 |
| 373 | GSMGSFSEK | I | EMC1 |
| 374 | IFLIDGVTGRI | I | EMC1 |

TABLE 3-continued

Additional peptides useful for cancer therapies, X = S, R or G

| SEQ ID No. | Sequence | MHC class | Gene |
|---|---|---|---|
| 375 | IPPEVQRI | I | EMC1 |
| 376 | IPYSPDVQI | I | EMC1 |
| 377 | QVAPPVLKR | I | EMC1 |
| 378 | TEKNVIAAL | I | EMC1 |
| 379 | VGKVKFASL | I | EMC1 |
| 380 | VPFSHVNI | I | EMC1 |
| 381 | VVYQYWNTK | I | EMC1 |
| 382 | YPSKQFDVL | I | EMC1 |
| 383 | AADDSADKV | I | ZNF217 |
| 384 | HHKEKQTDV | I | ZNF217 |
| 385 | KQTDVAAEV | I | ZNF217 |
| 386 | KSAFPAQSK | I | ZNF217 |
| 387 | NEVVQVHAA | I | ZNF217 |
| 388 | SEDLNKHVL | I | ZNF217 |
| 389 | GETIHIPTM | I | BCAT1 |
| 390 | GPKLASRIL | I | BCAT1 |
| 391 | GVKKPTKAL | I | BCAT1 |
| 392 | KEKPDPNNL | I | BCAT1 |
| 393 | KVSERYLTM | I | BCAT1 |
| 394 | LPVFDKEEL | I | BCAT1 |
| 395 | LSKLTDIQY | I | BCAT1 |
| 396 | DLSNIINKL | I | WDR12 |
| 397 | RVWDVESGSLK | I | WDR12 |
| 398 | SPTTSHVGA | I | WDR12 |
| 399 | VEIEYVEKY | I | WDR12 |
| 400 | VERNKVKAL | I | WDR12 |
| 401 | REAVSKEDL | I | PANK2 |
| 402 | IMGGNSILHSA | I | STXBP6 |
| 403 | KQFEGSTSF | I | STXBP6 |
| 404 | EEFLRQEHF | I | OASL |
| 405 | ETIPSEIQVF | I | OASL |
| 406 | EVGEALKTVL | I | DMD |
| 407 | KLEDLEEQL | I | DMD |
| 408 | LKIQSIAL | I | DMD |
| 409 | MNVLTEWLAAT | I | DMD |
| 410 | AIQDKLFQV | I | CHCHD6 |
| 411 | FPNFDKQEL | I | SMARCAD1 |

TABLE 3-continued

Additional peptides useful for cancer therapies, X = S, R or G

| SEQ ID No. | Sequence | MHC class | Gene |
|---|---|---|---|
| 412 | GQTKEVLVI | I | SMARCAD1 |
| 413 | KLIESTSTM | I | SMARCAD1 |
| 414 | KPYQKVGL | I | SMARCAD1 |
| 415 | KQESIVLKL | I | SMARCAD1 |
| 416 | NANNRLLL | I | SMARCAD1 |
| 417 | SEVPNGKEV | I | SMARCAD1 |
| 418 | TNNIGSIAR | I | PANK2 |
| 419 | DAKGRTVSL | I | GPX8 |
| 420 | IIKKKEDL | I | GPX8 |
| 421 | DVIDVVQAL | I | C20orf194 |
| 422 | EEFKITSF | I | C20orf194 |
| 423 | SDFEKTGF | I | C20orf194 |
| 424 | DEDRLLVVF | I | USP34 |
| 425 | HHSNIPMSL | I | USP34 |
| 426 | LFPSLIKNL | I | USP34 |
| 427 | NTNIPIGNK | I | USP34 |
| 428 | SDQVADLR | I | USP34 |
| 429 | THFSFPLRL | I | USP34 |
| 430 | TYDSVTDKF | I | USP34 |
| 431 | AESLYEIRF | I | TM9SF1 |
| 432 | DEFLGLTHTY | I | TM9SF1 |
| 547 | IITEVITRL | I | MUC16 |
| 548 | KMISAIPTL | I | MUC16 |
| 549 | TYSEKTTLF | I | MUC16 |

TABLE 4

Additional peptides useful for cancer therapies, X = S, R or G

| SEQ ID No. | Sequence | MHC class | Gene |
|---|---|---|---|
| 433 | ALDFFGNGPPVNY | II | IFI30 |
| 434 | ALDFFGNGPPVNYKT | II | IFI30 |
| 435 | DFFGNGPPVNYK | II | IFI30 |
| 436 | DFFGNGPPVNYKT | II | IFI30 |
| 437 | DFFGNGPPVNYKTGN | II | IFI30 |
| 438 | DFFGNGPPVNYKTGNL | II | IFI30 |
| 439 | DFFGNGPPVNYKTGNLY | II | IFI30 |
| 440 | LQALDFFGNGPPVNYKTGN | II | IFI30 |

TABLE 4-continued

Additional peptides useful for cancer therapies, X = S, R or G

| SEQ ID No. | Sequence | MHC class | Gene |
|---|---|---|---|
| 441 | QALDFFGNGPPVNYK | II | IFI30 |
| 442 | QPPHEYVPWVTVNGKP | II | IFI30 |
| 443 | SPLQALDFFGNGPPVNYKTG | II | IFI30 |
| 444 | SPLQALDFFGNGPPVNYKTGN | II | IFI30 |
| 445 | SPLQALDFFGNGPPVNYKTGNLY | II | IFI30 |
| 446 | GPPFSSSQSIPVVPR | II | GPR64 |
| 447 | LPSSLMNNLPAHDM | II | GPR64 |
| 448 | LPSSLMNNLPAHDME | II | GPR64 |
| 449 | LPSSLMNNLPAHDMEL | II | GPR64 |
| 450 | SPIGEIQPLSPQPSAPI | II | GPR64 |
| 451 | DEVTQPFVIDEKTAEIR | II | PCDHB5 |
| 452 | KYPELVLDKALDREER | II | PCDHB5 |
| 453 | KYPELVLDKALDREERPE | II | PCDHB5 |
| 454 | VTQPFVIDEKTAEIR | II | PCDHB5 |
| 455 | DGRTIVDLEGTPVVSPD | II | FNDC1 |
| 456 | DGRTIVDLEGTPVVSPDG | II | FNDC1 |
| 457 | DKPILSLGGKPLVG | II | FNDC1 |
| 458 | GDGRTIVDLEGTPVVSPD | II | FNDC1 |
| 459 | GDGRTIVDLEGTPVVSPDG | II | FNDC1 |
| 460 | GGDGRTIVDLEGTPVVSPD | II | FNDC1 |
| 461 | GGDGRTIVDLEGTPVVSPDG | II | FNDC1 |
| 462 | GRTIVDLEGTPVVSPD | II | FNDC1 |
| 463 | KVKEYILSYAPALKPF | II | FNDC1 |
| 464 | KVKEYILSYAPALKPFG | II | FNDC1 |
| 465 | LGGDGRTIVDLEGTPVVSPDG | II | FNDC1 |
| 466 | RTHEIKKLASESVYV | II | FNDC1 |
| 467 | VKEYILSYAPALKPF | II | FNDC1 |
| 468 | YSKTQYNQVPSEDFERTPQ | II | CXADR |
| 469 | AAPNLSRMGAIPVMIP | II | CXADR |
| 470 | AAPNLSRMGAIPVMIPA | II | CXADR |
| 471 | APNLSRMGAIPVMIP | II | CXADR |
| 472 | APNLSRMGAIPVMIPA | II | CXADR |
| 473 | GYSKTQYNQVPSEDFERTPQ | II | CXADR |
| 474 | SKTQYNQVPSEDFER | II | CXADR |
| 475 | SKTQYNQVPSEDFERTP | II | CXADR |
| 476 | SKTQYNQVPSEDFERTPQ | II | CXADR |
| 477 | VAAPNLSRMGAIPVMIPA | II | CXADR |
| 478 | VIILYSGDKIYD | II | CXADR |
| 479 | YSKTQYNQVPSEDFER | II | CXADR |
| 480 | GHLFALRSLDYE | II | PCDHB3 |
| 481 | AAEPGYLVTKVVAVDG | II | PCDHB3 |
| 482 | AAEPGYLVTKVVAVDGD | II | PCDHB3 |
| 483 | AAEPGYLVTKVVAVDGDS | II | PCDHB3 |
| 484 | AAEPGYLVTKVVAVDGDSG | II | PCDHB3 |
| 485 | AEPGYLVTKVVAVDG | II | PCDHB3 |
| 486 | AEPGYLVTKVVAVDGD | II | PCDHB3 |
| 487 | AEPGYLVTKVVAVDGDS | II | PCDHB3 |
| 488 | EPGYLVTKVVAVDG | II | PCDHB3 |
| 489 | EPGYLVTKVVAVDGD | II | PCDHB3 |
| 490 | EPGYLVTKVVAVDGDS | II | PCDHB3 |
| 491 | AEPGYLVTKVVAVD | II | PCDHB3 |
| 492 | ADSTEFRPNAPVPLVI | II | CTPS2 |
| 493 | ADSTEFRPNAPVPLVID | II | CTPS2 |
| 494 | DADSTEFRPNAPVPLVI | II | CTPS2 |
| 495 | DADSTEFRPNAPVPLVID | II | CTPS2 |
| 496 | DADSTEFRPNAPVPLVIDM | II | CTPS2 |
| 497 | DADSTEFRPNAPVPLVIDMP | II | CTPS2 |
| 498 | DADSTEFRPNAPVPLVIDMPE | II | CTPS2 |
| 499 | DSTEFRPNAPVPL | II | CTPS2 |
| 500 | DSTEFRPNAPVPLV | II | CTPS2 |
| 501 | DSTEFRPNAPVPLVI | II | CTPS2 |
| 502 | DSTEFRPNAPVPLVID | II | CTPS2 |
| 503 | DSTEFRPNAPVPLVIDMP | II | CTPS2 |
| 504 | DSTEFRPNAPVPLVIDMPE | II | CTPS2 |
| 505 | KDADSTEFRPNAPVPLVID | II | CTPS2 |
| 506 | STEFRPNAPVPL | II | CTPS2 |
| 507 | STEFRPNAPVPLVI | II | CTPS2 |
| 508 | STEFRPNAPVPLVID | II | CTPS2 |
| 509 | STEFRPNAPVPLVIDMP | II | CTPS2 |
| 510 | AGDYTIANARKLIDE | II | RP2 |
| 511 | ETLERLQEL | | DMD |
| 512 | ADITYAIEADSESVK | II | FAT1 |
| 513 | DITYAIEADSESVK | II | FAT1 |
| 514 | KRDNYQIKVVASDHGE | II | FAT1 |

TABLE 4-continued

Additional peptides useful for cancer therapies, X = S, R or G

| SEQ ID No. | Sequence | MHC class | Gene |
|---|---|---|---|
| 515 | KRDNYQIKVVASDHGEK | II | FAT1 |
| 516 | RDESFVIDRQSGRLK | II | FAT1 |
| 517 | RDNYQIKVVASDHGE | II | FAT1 |
| 518 | SPSELDRDPAYAIVT | II | FAT1 |
| 519 | TPPQFSSVKVIHVTSPQ | II | FAT1 |
| 520 | VPLPDIQEFPNY | II | FAT1 |
| 521 | GPQLFHMDPSGTFVQ | II | PSMA5 |
| 522 | DKNYFEGTGYARVPTQP | II | LAMA3 |
| 523 | DKNYFEGTGYARVPTQPH | II | LAMA3 |
| 524 | DSKPLYTPSSSFGVS | II | LAMA3 |
| 525 | IQRQVKEINSLQSDFT | II | LAMA3 |
| 526 | KNYFEGTGYARVPT | II | LAMA3 |
| 527 | KNYFEGTGYARVPTQP | II | LAMA3 |
| 528 | KNYFEGTGYARVPTQPH | II | LAMA3 |
| 529 | SPRVVPNESIPIIPIP | II | PTPRG |
| 530 | SPRVVPNESIPIIPIPD | II | PTPRG |
| 531 | SSPRVVPNESIPIIP | II | PTPRG |
| 532 | SSPRVVPNESIPIIPIP | II | PTPRG |
| 533 | SSPRVVPNESIPIIPIPD | II | PTPRG |
| 534 | DDKGYTLMHPSLTRPY | II | CACHD1 |
| 535 | DVGGAGYVVTISHTIHS | II | CACHD1 |
| 536 | GAGYVVTISHTIH | II | CACHD1 |
| 537 | GAGYVVTISHTIHS | II | CACHD1 |
| 538 | GGAGYVVTISHTIH | II | CACHD1 |
| 539 | GGAGYVVTISHTIHS | II | CACHD1 |
| 540 | VGGAGYVVTISHTIHS | II | CACHD1 |
| 541 | MTRTFHDLEGNAVKRDSG | II | ERMP1 |
| 542 | RTFHDLEGNAVKR | II | ERMP1 |
| 543 | RTFHDLEGNAVKRDSG | II | ERMP1 |
| 544 | SGTFFPYSSNPANPK | II | ERMP1 |
| 545 | SGTFFPYSSNPANPKP | II | ERMP1 |
| 546 | TRTFHDLEGNAVKR | II | ERMP1 |

The present invention furthermore generally relates to the peptides according to the present invention for use in the treatment of proliferative diseases, such as, for example, ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer and other tumors that show an overexpression of a protein from which a peptide SEQ ID No. 1 to SEQ ID No. 319 is derived from.

Particularly preferred are the peptides—alone or in combination—according to the present invention selected from the group consisting of SEQ ID NO: 1 to SEQ ID NO: 549. More preferred are the peptides—alone or in combination—selected from the group consisting of SEQ ID NO: 1 to SEQ ID NO: 319 (see Table 1 and 2), and their uses in the immunotherapy of ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, and bile duct cancer, and preferably ovarian cancer.

Thus, another aspect of the present invention relates to the use of the peptides according to the present invention for the—preferably combined—treatment of a proliferative disease selected from the group of ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, and bile duct cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 549.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expresses said peptide containing SEQ ID No. 1 to SEQ ID No.: 549, preferably containing SEQ ID No. 1 to SEQ ID No. 319, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, the medicament is active against cancer.

Preferably, said medicament is for a cellular therapy, a vaccine or a protein based on a soluble TCR or antibody.

The present invention further relates to a use according to the present invention, wherein said cancer cells are ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, and bile duct cancer, and preferably ovarian cancer cells.

The present invention further relates to biomarkers based on the peptides according to the present invention, herein called "targets" that can be used in the diagnosis of cancer, preferably ovarian cancer The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Both therapeutic and diagnostic uses against additional cancerous diseases are disclosed in the following more detailed description of the underlying expression products (polypeptides) of the peptides according to the invention.

BRIEF DESCRIPTION OF THE DRAWINGS

FIGS. 1A and 1B describe an embodiment as described herein.

DETAILED DESCRIPTION OF A PREFERRED EMBODIMENT

Figures 1, 1B:
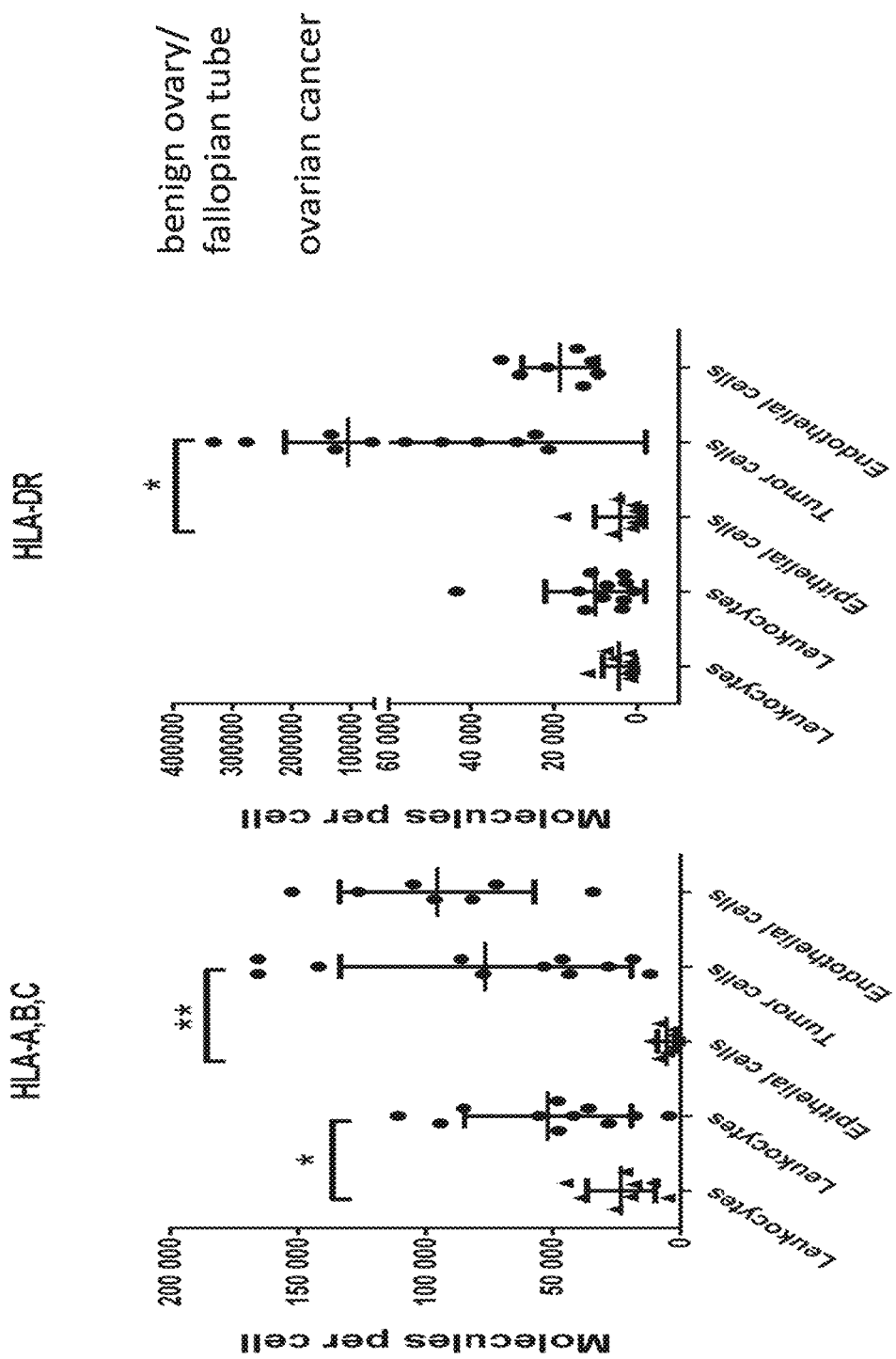

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The present invention further relates to a peptide according to the present invention, wherein said peptide is modified and/or includes non-peptide bonds as described herein below.

The present invention further relates to a peptide according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells, i.e. binds to dendritic cells.

The present invention further relates to a nucleic acid, encoding for a peptide according to the present invention. The present invention further relates to the nucleic acid according to the present invention that is DNA, cDNA, PNA, RNA or combinations thereof.

The present invention further relates to an expression vector capable of expressing, expressing, and/or presenting a nucleic acid according to the present invention.

The present invention further relates to a peptide according to the present invention, a nucleic acid according to the present invention or an expression vector according to the present invention for use in medicine.

The present invention further relates to antibodies as described further below, and methods of making them. Preferred are antibodies that are specific for the peptides of the present invention, and/or for the peptides of the present invention when bound to their MHC. Preferred antibodies can be monoclonal.

The present invention further relates to T-cell receptors (TCR), in particular soluble TCR (sTCRs) targeting the peptides according to the invention and/or the peptide—MHC complexes thereof, and methods of making them.

The present invention further relates to antibodies or other binding molecules targeting the peptides according to the invention and/or the peptide—MHC complexes thereof, and methods of making them.

The present invention further relates to a host cell comprising a nucleic acid according to the present invention or an expression vector as described before. The present invention further relates to the host cell according to the present invention that is an antigen presenting cell. The present invention further relates to the host cell according to the present invention, wherein the antigen presenting cell is a dendritic cell.

The present invention further relates to a method of producing a peptide according to the present invention, said method comprising culturing the host cell according to the present invention, and isolating the peptide from the host cell and/or its culture medium.

The present invention further relates to an in vitro method for producing activated T-cells, the method comprising contacting in vitro T cells with antigen loaded human class I or II MHC molecules expressed on the surface of a suitable antigen-presenting cell for a period of time sufficient to activate said T cells in an antigen specific manner, wherein said antigen is at least one peptide according to the present invention.

The present invention further relates to a method, wherein the antigen is loaded onto class I or II MHC molecules expressed on the surface of a suitable antigen-presenting cell by contacting a sufficient amount of the antigen with an antigen-presenting cell.

The present invention further relates to the method according to the present invention, wherein the antigen-presenting cell comprises an expression vector capable of expressing said peptide containing SEQ ID NO: 1 to SEQ ID NO: 549, or a variant amino acid sequence.

The present invention further relates to activated T cells, produced by the method according to the present invention, which selectively recognize a cell, which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated T-cell according to the present invention as a medicament or in the manufacture of a medicament.

The present invention further relates to a use according to the present invention, wherein said medicament is a vaccine, a cell, a cell population, such as, for example, a cell line, sTCRs and monoclonal antibodies.

The present invention further relates to a use according to the present invention, wherein the medicament is active against cancer.

The present invention further relates to a use according to the present invention, wherein said cancer cells are cells of ovarian cancer.

The present invention further relates to particular marker proteins and biomarkers based on the peptides according to the present invention that can be used in the diagnosis and/or prognosis of ovarian cancer.

Furthermore, the present invention relates to the use of these novel targets for cancer treatment.

Further, the present invention relates to a method for producing a personalized anti-cancer vaccine for an individual patient using a database (herein designated also as "warehouse") of pre-screened tumor associated peptides.

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

Tremendous progress in the field of cancer immunotherapy during the last years has led to its wide appreciation as a potentially curative addition or alternative to standard chemotherapeutic approaches. Several papers demonstrate the importance of HLA presented mutated and wild type tumor associated antigens as valuable tumor rejection antigens. Therefore, large scale identification of HLA presented cancer specific tumor antigens adds another important piece to the puzzle of our understanding how the immune system identifies and recognizes tumor cells.

In the present invention the inventors focused on epithelial ovarian cancer (EOC) with the goal to comprehensively characterize the immunopeptidome of EOC and evaluate the HLA presented antigens for their usefulness in clinical applications. So far, only few HLA presented antigens have been identified for EOC and most clinical studies have relied on predicted or established cancer testis antigens not necessarily also frequently presented by EOC, a fact that could be confirmed by our analysis.

The inventors demonstrate a consistent and high expression of HLA class I molecules on ovarian tumor cells in line with previously published data. Furthermore, the inventors show on a single cell level that EOC also display a strong expression of HLA-DR molecules. This strong expression was further underlined by our identification of large amounts of MHC class II ligands emanating from ovarian tumors as well as from highly enriched tumor cell fractions.

Profiling of the immunopeptidome of 34 ovarian tumors in comparison to more than 85 benign sources of different origin, revealed several hundred EOC associated antigens. Among the TOP100 HLA class I EOC antigens not presented on any of the tissues in our benign dataset MUC16 was clearly most exceptional. Concerning both the number of HLA ligands identified (>80) and the frequency of presentation in the patient cohort (~80%) this is unprecedented for any other tumor antigen and tumor entity the inventors have investigated so far. Moreover, the inventors could establish that more than 70% of HLA ligands derived from MUC16 are immunogenic and able to prime T cells in healthy individuals rendering mucin 16 an unparalleled first-class antigen for EOC immunotherapy. Immunopeptidome profiling further provides a showcase for apparent mechanistic insights into EOC, which are reflected in the HLA ligandome of both HLA class I and class II ligands. HLA ligands from important kinases and phosphatases (DDR1, EYA2), transcription factors (SOX9, SOX17), proteins associated with immunosuppression (IDO1, Galectin 1) as well as established and suspected molecular markers for EOC (MUC1, KLK10, FOLR1) are only a few to mention. Notably for HLA class II, mesothelin an established ligand of MUC16 has been identified as the TOP1 tumor associated antigen. Several studies have demonstrated the pivotal role of the MUC16/MSLN axis for cell invasion and metastasis in EOC as well as in other tumors such as pancreatic cancer or mesothelioma, suggesting that T-cell epitopes of these antigens should be further tested in other malignancies. The inventors could show that MSLN staining is directly correlated with MUC16 staining and high MSLN expression forms a negative prognostic factor in EOC.

For the first time several different benign tissues and cell types (PBMCs, bone marrow, liver, kidney, colon, ovary) have been used for this kind of selective immunopeptidome profiling. Due to restrictions in the number of different tissues available for investigation the inventors cannot completely exclude that individual antigens might also be presented by HLA molecules in other organs. The established functional relevance of those antigens for EOC and particularly the immunogenicity of the respective peptides in healthy individuals however, make a presentation of these antigens in other tissues unlikely.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 and in case of MHC class II peptides (elongated variants of the peptides of the invention) they can be as long as 15, 16, 17, 18, 19 or 20 amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "the peptides of the present invention" shall also include the peptides consisting of or comprising a peptide as defined above according to SEQ ID NO: 1 to SEQ ID NO: 549.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to different HLA types. A vaccine may also include pan-binding MHC class II peptides and peptides binding to other alleles, which will be helpful for, personalized medicines. Therefore, the vaccine of the invention can be used to treat cancer in patients that are A*02 positive, whereas no selection for MHC class II allotypes is necessary due to the pan-binding nature of these peptides.

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene, which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly disclosed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity}=100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 549 or a variant thereof which is 88% homologous to SEQ ID NO: 1 to SEQ ID NO: 549, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 549. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 549, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acids whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 6.

TABLE 6

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than four amino acids, preferably to a total length of 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 μM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 549.

"Consisting essentially of" shall mean that a peptide according to the present invention, in addition to the sequence according to any of SEQ ID NO: 1 to SEQ ID NO 549 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenyl-methoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure, which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from ovarian cancer samples with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from ovarian cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from ovarian cancer tissue samples were purified and HLA-associated peptides were isolated and analyzed by LC-MS (see examples). All TUMAPs contained in the present application were identified with this approach on primary ovarian cancer samples confirming their presentation on primary ovarian cancer.

TUMAPs identified on multiple ovarian cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention provides peptides that are useful in treating cancers/tumors, preferably ovarian cancer that over- or exclusively present the peptides of the invention. These peptides were shown by mass spectrometry to be naturally presented by HLA molecules on primary human ovarian cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy ovarian tissue cells or other normal tissue cells, demonstrating a high degree of tumor association of the source genes. Moreover, the peptides themselves are strongly over-presented on tumor tissue—"tumor tissue" in relation to this invention shall mean a sample from a patient suffering from ovarian cancer, but not on normal tissues.

HLA-bound peptides can be recognized by the immune system, specifically T lymphocytes. T cells can destroy the cells presenting the recognized HLA/peptide complex, e.g. ovarian cancer cells presenting the derived peptides.

The peptides of the present invention have been shown to be capable of stimulating T cell responses and/or are over-presented and thus can be used for the production of antibodies and/or TCRs, such as soluble TCRs, according to the present invention. Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are HAVCR1-001 peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an inventive peptide-HLA molecule complex with a binding affinity (KD) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for an HAVCR1-001 peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an inventive peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to an inventive peptide can be enhanced by methods well known in the art.

The present description further relates to a method of identifying and isolating a TCR according to the present description, said method comprising incubating PBMCs from HLA-A*02-negative healthy donors with A2/inventive peptide monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with an inventive peptide, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutics such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes, which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 549, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL (SEQ ID NO: 559), or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells, which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 μg and 1.5 mg, preferably 125 μg to 500 μg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMA-TRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-

MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, Celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or Virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labeling which provides that the bound scaffold can be detected by determining the presence or absence of a signal provided by the label. For example, the scaffold can be labeled with a fluorescent dye or any other applicable cellular marker molecule. Such marker molecules are well known in the art. For example a fluorescence-labeling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 549, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is regarded as "specific" in the context of the present invention.

The present invention relates to a peptide comprising a sequence that is selected from the group consisting of SEQ ID NO: 1 to SEQ ID NO: 549, or a variant thereof which is at least 88% homologous (preferably identical) to SEQ ID NO: 1 to SEQ ID NO: 549 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 549 or a variant thereof which is at least 88% homologous (preferably identical) to SEQ ID NO: 1 to SEQ ID NO: 549, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 549.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

Another embodiment of the present invention relates to a non-naturally occurring peptide wherein said peptide consists or consists essentially of an amino acid sequence according to SEQ ID No: 1 to SEQ ID No: 48 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, $KCl$, $NaCl$, and $CaCl_2$), such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrine, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of ovarian cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 549 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are ovarian cancer cells or other solid or hematological tumor cells such as pancreatic cancer, brain cancer, kidney cancer, colon or rectal cancer, leukemia.

The present invention further relates to particular marker proteins and biomarkers based on the peptides according to the present invention, herein called "targets" that can be used in the diagnosis and/or prognosis of ovarian cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a ovarian cancer marker polypeptide, delivery of a toxin to a ovarian cancer cell expressing a cancer marker gene at an increased level, and/or inhibiting the activity of a ovarian cancer marker polypeptide) according to the invention.

Whenever possible, the antibodies of the invention may be purchased from commercial sources. The antibodies of the invention may also be generated using well-known methods. The skilled artisan will understand that either full length ovarian cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 549, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the ovarian cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed lung cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source, which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intra tumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (µg/kg to up to 100 mg/kg of body weight or more per day, depending on the factors mentioned above. Following administration of an antibody, preferably for treating ovarian cancer, the efficacy of the therapeutic antibody can be assessed in various ways well known to the skilled practitioner. For instance, the size, number, and/or distribution of lung cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of lung cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 549, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e.g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 549.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Because the underlying polypeptides of the peptides of the invention as mentioned in the Tables above are highly expressed in ovarian cancer, and are expressed at rather to extremely low levels in normal cells, targeting peptides derived from the protein products of the following genes may preferably be integrated into a therapeutic strategy:

The present invention further provides a medicament that is useful in treating cancer, in particular ovarian cancer and other malignancies.

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 μg) and preferably not more than 3 mg/mL/peptide (=1500 μg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container. The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from ovarian cancer, the medicament of the invention is preferably used to treat ovarian cancer.

The present invention further includes a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides, which were highly overexpressed in the tumor tissue of ovarian cancer patients with various HLA-A HLA-B and HLA-C alleles. It may contain MHC class I and MHC class II peptides or elongated MHC class I peptides. In addition to the tumor associated peptides collected from several ovarian cancer tissues, the warehouse may contain HLA-A*02 and HLA-A*24 as well as HLAs with smaller abundance marker peptides. These peptides allow comparison of the magnitude of T-cell immunity induced by TUMAPS in a quantitative manner and hence allow important conclusion to be drawn on the capacity of the vaccine to elicit anti-tumor responses.

Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immuno-competence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, ovarian cancer samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (ovarian cancer) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from ovarian cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from ovarian cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for ovarian cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples, which describe preferred embodiments thereof, nevertheless, without being limited thereto. For the purposes of the present invention, all references as cited herein are incorporated by reference in their entireties.

FIGURES

FIGS. 1A and 1B show the HLA-A,B,C (FIG. 1A) and HLA-DR (FIG. 1B) expression of different cell subsets within ovarian cancer and benign ovarian tissue. For FIG. 1 the two-tailed unpaired Student's t-test with Welch's correction was used owing to unequal variance between the two comparison groups. HLA class I (FIG. 1A) and HLA-DR (FIG. 1B) expression on different cell types within EOC and benign ovarian tissue after enzymatic dissociation characterized by distinct cell surface markers (leukocyte compartments: CD45+, tumor cells/epithelial cell compartments: CD45-EpCam+, endothelial cell compartments: CD45-CD31+). Each data point represents the mean of triplicate experiments performed for each sample. Two sided t-tests were used to test for significance (*p<0.05; ** p<0.01).

FIGS. 2A to 2D show the comparative profiling of the immunopeptidome of EOC vs. benign tissues. (FIG. 2A) Comparative profiling of HLA class I ligand source proteins represented in EOC (n=34) and benign tissues. The frequency of HLA restricted presentation of source proteins is indicated on the y-axis separately for EOC (above x-axis) and benign sources (below x-axis). The source proteins were ranked (from left to right) according to their frequency of EOC specific presentation. The box on the left side highlights the TOP100 HLA ligand source proteins exclusively presented by EOC. (FIG. 2B) Word cloud of the TOP 100 EOC specific HLA class I ligand source proteins (uniprot recommended gene name). Font size (5-26) correlates with absolute number of cancer patients presenting HLA ligands of respective source proteins. (FIG. 2C) Comparative profiling of HLA class II ligand source proteins represented in EOC (n=22) and benign tissues. (FIG. 2D) Word cloud of the TOP 100 EOC specific HLA class II ligand source proteins (uniprot recommended gene name). Font size (3-11) correlates with absolute number of cancer patients presenting HLA ligands of respective source proteins.

Figure 3:
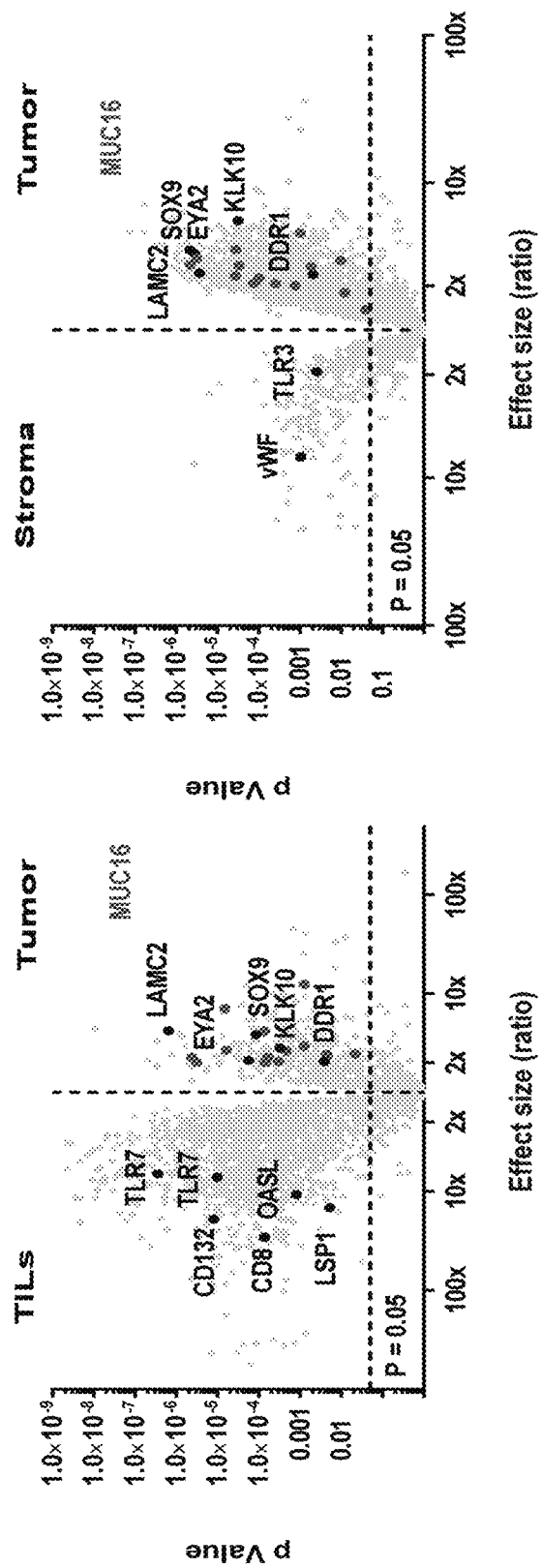
FIGS. 3A and 3B describe an embodiment as described herein.
Figure 3:
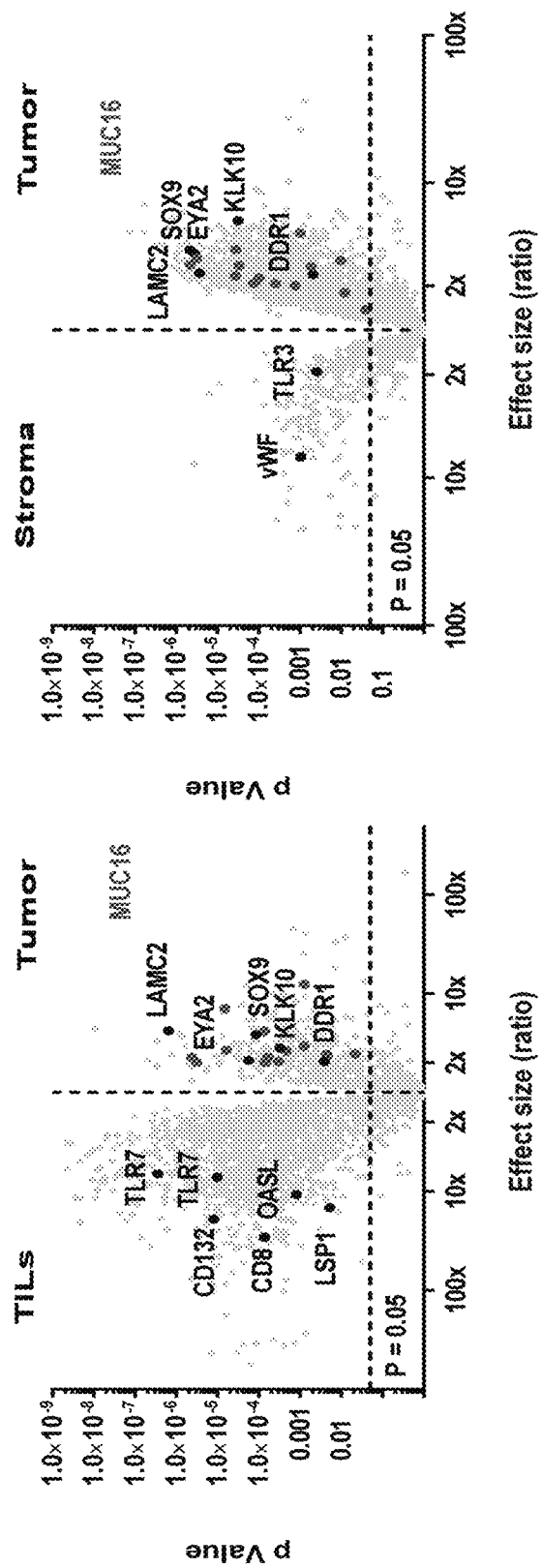

FIGS. 3A and 3B show the cellular origin of the TOP100 EOC associated HLA class I ligands. Volcano plots of the relative abundance of HLA ligands in the class I immunopeptidome of enriched cell populations of OvCa 84 analyzed by label free quantitation. Panels show on the left side (FIG. 3A) tumor infiltrating leukocytes (CD45+) vs. tumor cells (CD45-Epcam+) and on the right side (FIG. 3B) stroma cells (CD45-EpCam-) vs. tumor cells. The horizontal dashed line indicates significance threshold (p<0.05). TOP100 EOC exclusive ligands (MUC16 (red), DDR1, EYA2, SOX9, TLR7, OASL) as well as ligands derived from leukocyte associated antigens (CD132, CD8, LSP1) and stroma (endothelial cell) associated antigens (vWF) are highlighted.

Figure 4A:
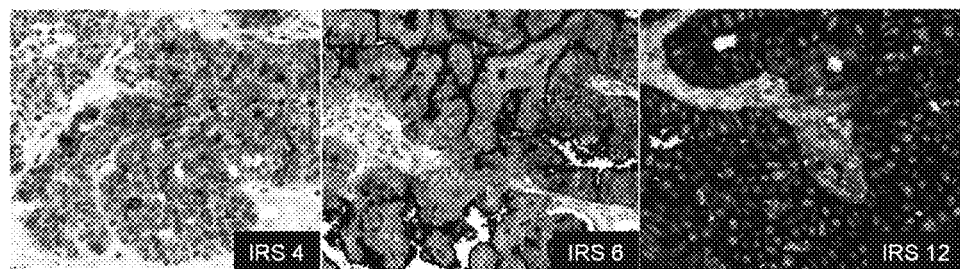
FIGS. 4A-4D describe an embodiment as described herein.
Figure 4B:
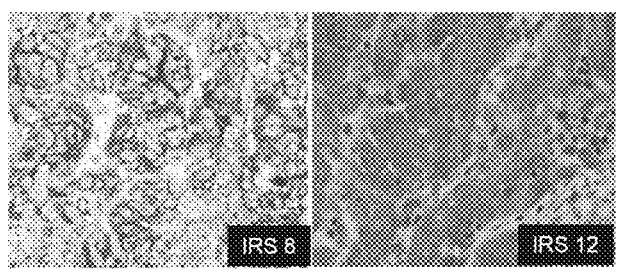
Figure 4C:
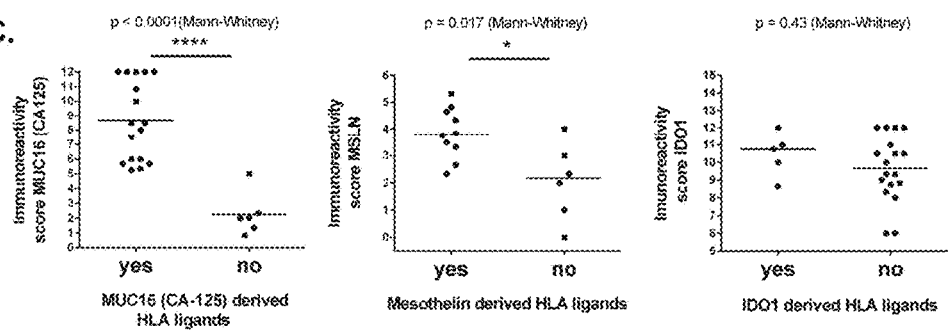
Figure 4D:
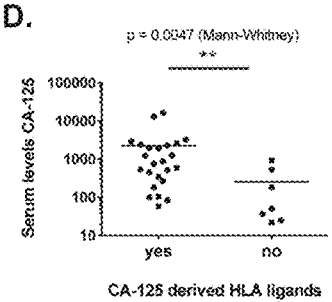

FIGS. 4A-4D show the immunohistochemical staining and serum levels as surrogate markers for ligand presentation. Immunohistochemical staining of high-grade serous ovarian carcinomas for MUC16 (CA-125) with low (IRS4), intermediate (IRS6) and high (IRS12) immunoreactivity score (FIG. 4A). Immunohistochemical staining for Mesothelin (right, IRS8) and IDO1 (left, IRS 12; all at 200× magnification) (FIG. 4B). Correlation of HLA ligand presentation and source protein expression of selected TOP100 EOC associated antigens. Expression of MUC16 (n=23), IDO1 (n=23) and MSLN (n=16) was analyzed by immunohistochemical staining (FIG. 4C) or serum marker analysis of CA-125 (n=30) at the day of surgery (FIG. 4D). For MSLN only the cases for which HLA class II immunopeptidome data were available were included. Non parametric Mann-Whitney test was employed to test for statistical significance (p<0.05 was considered significant).

Figure 5A:
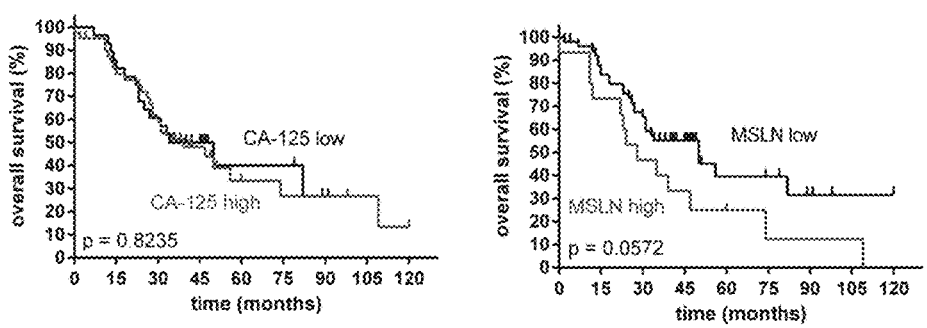
FIGS. 5A-5C describe an embodiment as described herein.
Figure 5B:
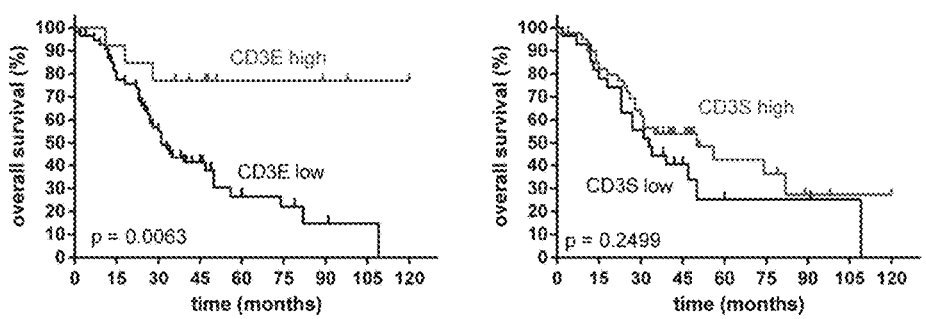
Figure 5C:
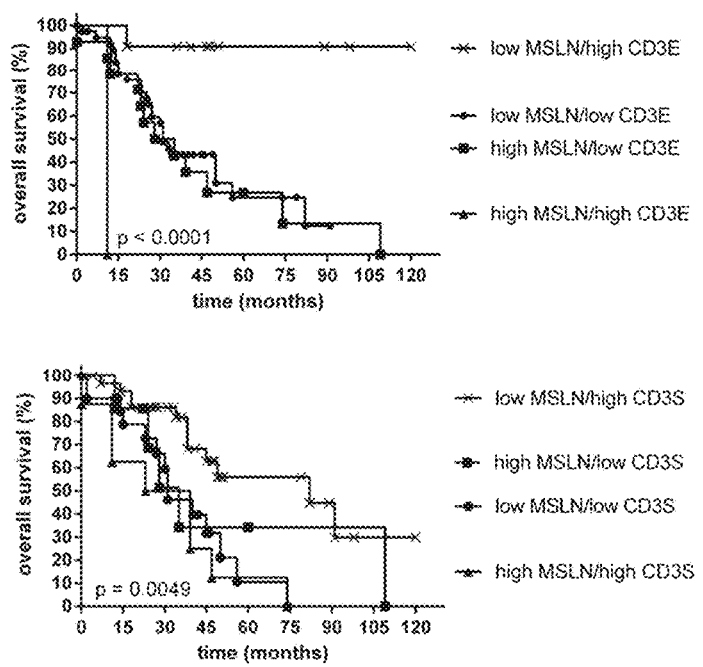

FIGS. 5A-5C show the prognostic relevance of MUC16 and MSLN. Immunohistochemical stainings were performed on TMAs with 71 high-grade serous EOC samples from patients with documented optimal tumor debulking. (FIG. 5A) Kaplan Meier plot depicting the influence of MUC16 expression (left panel, low expression score <7, n=41; high expression score ≥7, n=30) and MSLN expression (right panel, low expression <6, n=15; high expression ≥6, n=52) on overall survival. (FIG. 5B) Impact of CD3 T-cell infiltration into the intraepithelial compartment (left panel CD3E, low infiltration <7 cell/HPF, n=13; high infiltration 7, n=57) or the fibrovascular stroma (right panel, CD3S, low infiltration <7 cell/HPF, n=40; high infiltration ≥7, n=30) on overall survival of patients. (FIG. 5C) Subgroup analysis of combined CD3 and MLN staining (all scoring cutoffs as above) for intraepithelial CD3 T-cells (top panel, low MSLN/high CD3E, n=11; low MSLN/low CD3E, n=40; high MSLN/low CD3E, n=14; high MSLN/high CD3E, n=1) or fibrovascular CD3 T-cells (bottom panel, low MSLN/high CD3S, n=30; high MSLN/low CD3S, n=7; low MSLN/low CD3S, n=21; high MSLN/high CD3S, n=8).

Figure 6:
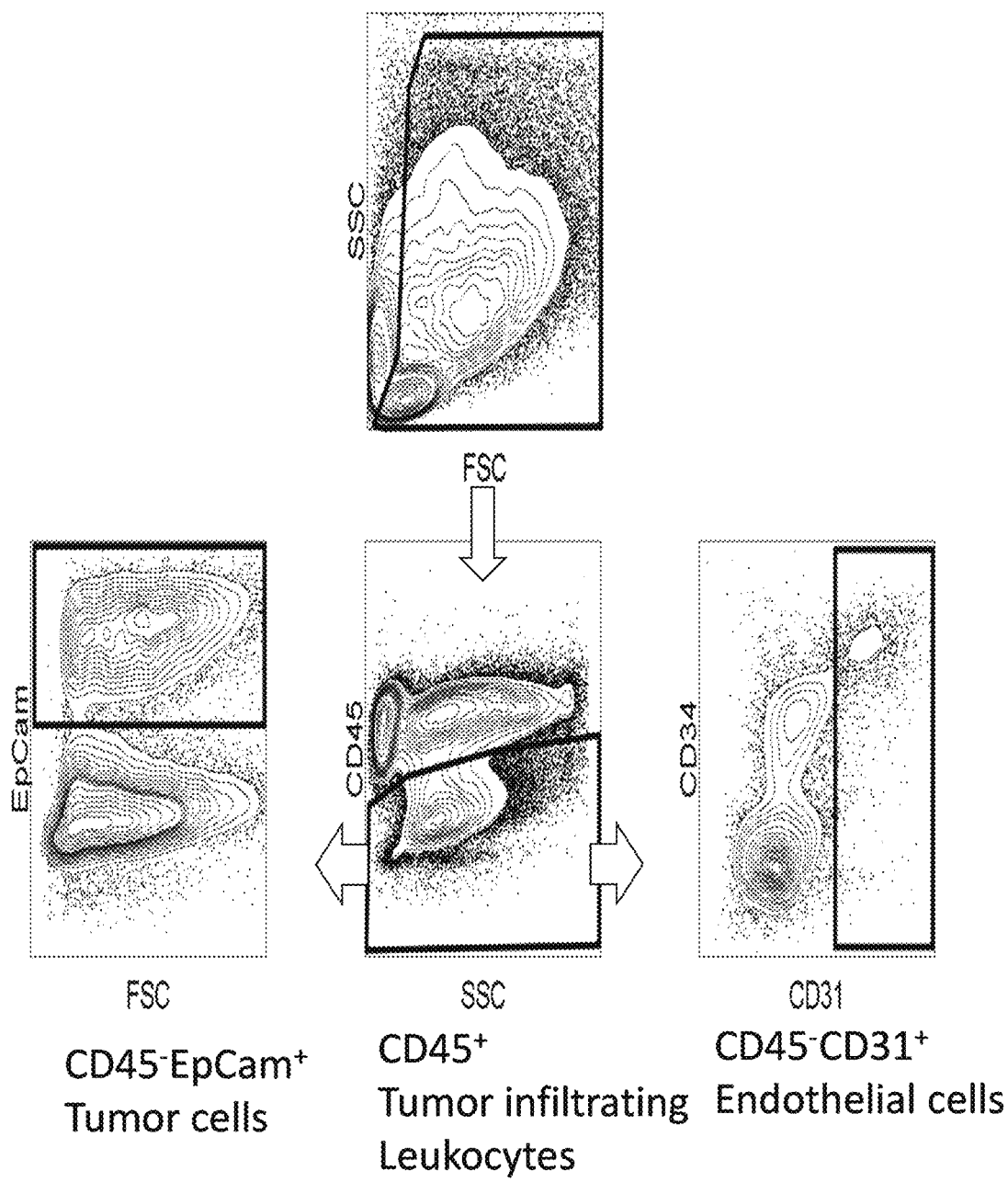
FIG. 6 describes an embodiment as described herein.

FIG. 6 shows the flow cytometric analysis of EOC and benign ovarian tissue. Exemplary presentation of the gating strategy for OvCa 48 showing the selection of CD45+ leukocytes, CD45-CD31+ endothelial cells and CD45-Ep-Cam+ tumor or epithelial cells.

Figure 7:
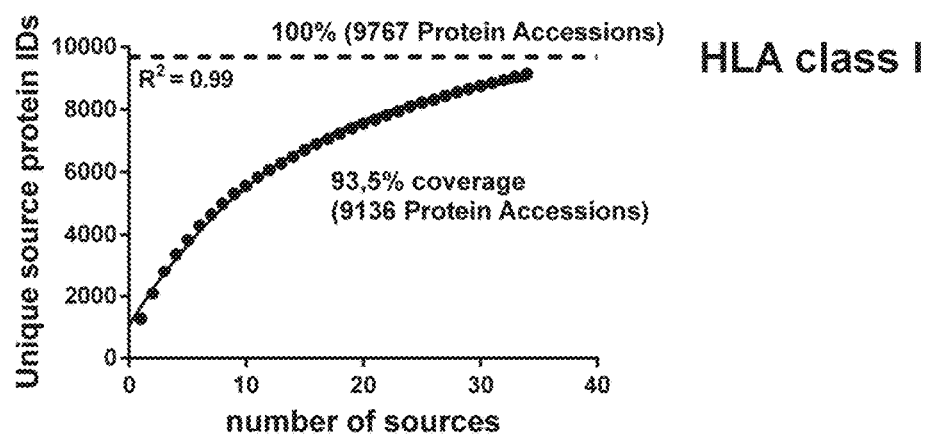
FIGS. 7A and 7B describe an embodiment as described herein.
Figure 7:
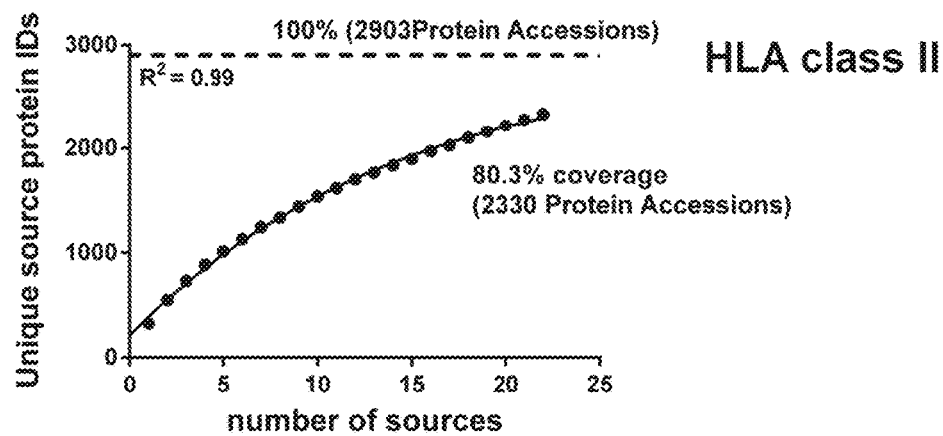

FIGS. 7A and 7B show the saturation analysis of HLA ligand source protein identifications for EOC. Saturation analysis for identifications of source proteins is depicted separately for HLA class I (FIG. 7A) and HLA class II (FIG. 7B) ligand proteins. The mean number of unique source proteins has been calculated for each source count by 1000 random samplings from the 34 EOC sources. Exponential regression was used to determine the calculated maximal attainable coverage of source protein accession (dotted lines) for EOC.

Figure 8:
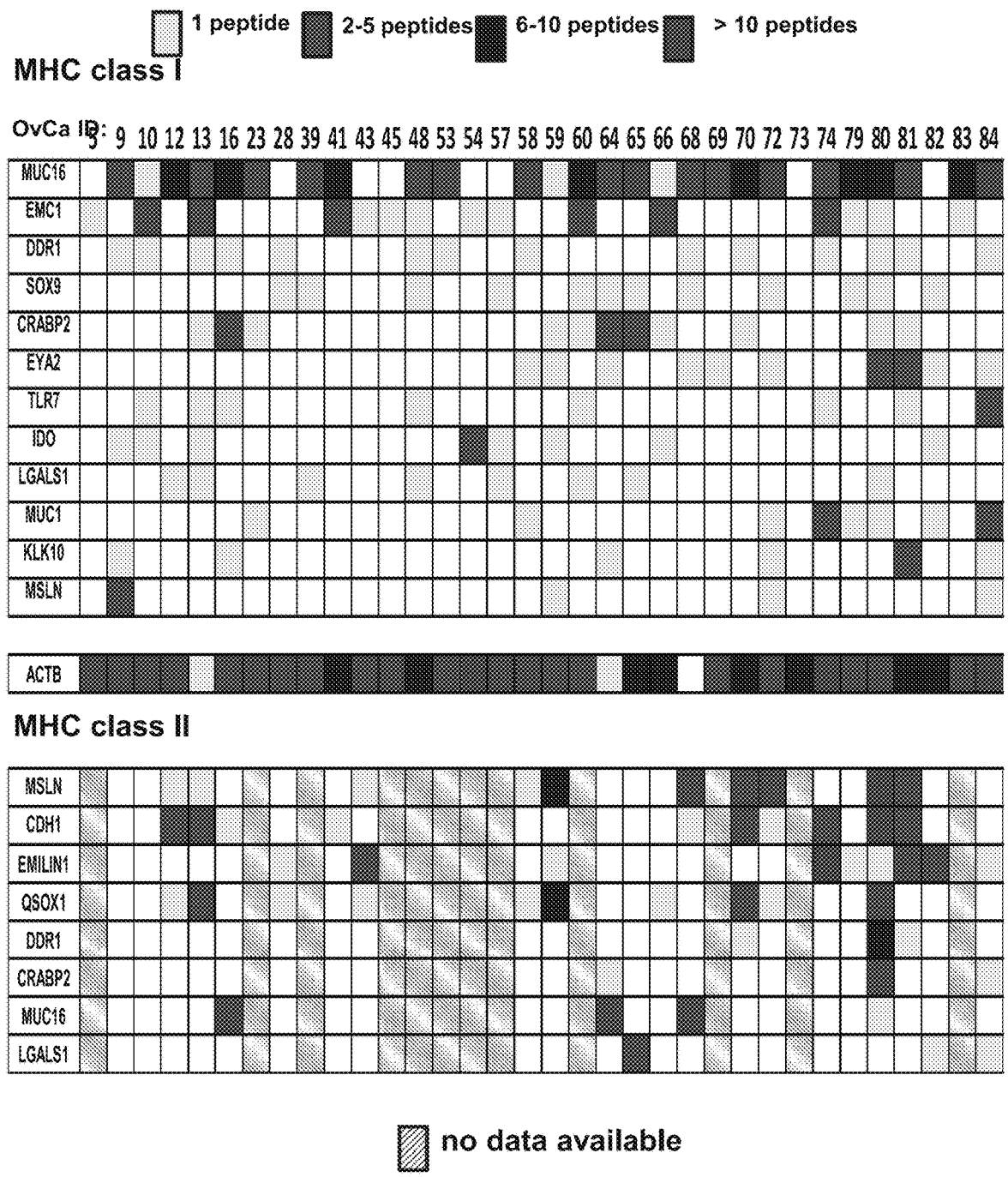
FIG. 8 describes an embodiment as described herein.

FIG. 8 shows the frequency and number of HLA ligand presentation among EOC samples. HLA presentation of selected EOC associated antigens as well as the number of different HLA presented peptides is visualized for each individual EOC (patient number on top of each column) both for class I (top) and class II (bottom) antigens.

EXAMPLES

Materials and Methods

Tissue Samples

All tissue samples were collected at the University Hospital of Tübingen after obtaining patient informed consent in accordance with the principles of the Declaration of Helsinki. All study protocols were approved by the local institutional review board. If not stated otherwise samples were stored at −80° C. until further usage. Two-digit HLA typing was performed by sequence specific primer (SSP) PCR using the HLA-Ready Gene System (Innotrain, Kronberg, Germany) and evaluated by SCORE Software (Olerup, Stockholm, Sweden) at the Department of Transfusion Medicine of the University Hospital of Tübingen. High resolution four-digit HLA typing was performed by next generation sequencing on a GS Junior Sequencer using the GS GType HLA Primer Sets (both Roche, Basel, Switzerland). Normal tissues were obtained from Bio-Options Inc, CA, USA; BioServe, Beltsville, Md., USA; Capital BioScience Inc, Rockville, Md., USA; Geneticist Inc., Glendale, Calif., USA; University Hospital of Geneva; University Hospital of Heidelberg; University Hospital Munich; ProteoGenex Inc., Culver City, Calif., USA; University Hospital of Tübingen. Written informed consents of all patients had been given before surgery or autopsy. Tissues were shock-frozen immediately after excision and stored until isolation of TUMAPs at −70° C. or below.

Tissue Dissociation

EOC as well as benign ovary and fallopian tube tissues were freshly collected from patients undergoing tumor resection/debulking or salpingoophorectomy. Tissues were minced into small pieces <2 mm$^3$ and transferred into an enzymatic dissociation solution containing 400 U/ml Collagenase Type IV, 5 U/ml Dispase (both life technologies, Carlsbad, Calif.) and 0.1 mg/ml DNAse (Roche, Basel, Switzerland) in DMEM (life technologies) with 10% fetal calf serum (Lonza, Basel, Switzerland). Dissociation was performed on a rotating shaker (Infors H T, Basel, Switzerland) for 3 hours at 37° C. Remaining tissue fragments (typically <1% of initial weight) were removed using a 100 µm cell strainer (BD, Franklin Lakes, N.J.). Single cell suspensions were washed twice with PBS and erythrocytes were lysed using ammonium chloride lysis buffer.

HLA Surface Molecule Quantification

HLA surface expression was determined using QIFIKIT quantification flow cytometric assay (Dako, Glostrup, Denmark) according to manufacturer's instructions. Cells were stained with either pan-HLA class I specific monoclonal antibody W6/32, HLA-DR specific L243 or respective isotype control. Discrimination of cell types was based on surface marker staining with fluorescently labeled antibodies directed against CD45 (AmCyan clone 2D1, BD), CD31 (PeCy7, clone WM59, Biolegend, San Diego, Calif.), EpCam (APC, clone HEA125, Miltenyi, Bergisch-Gladbach, Germany) and CD34 (APCCy7, clone 581, Biolegend). 7-AAD (BioLegend) was added as viability marker immediately before analysis on a LSR SORP Fortessa instrument (BD). Triplicates were recorded for each sample with median fluorescence intensities used for calculation of surface molecule expression.

Cell Separation:

Cell separation was performed using two consecutive magnetic activated cell separation (MACS) protocols according to manufacturer's instructions (Miltenyi). Separations were performed using XS columns and a superMACS separator (both Miltenyi). The first separation aimed at positive selection of CD45$^+$ leukocytes. The negative fraction was subsequently enriched for EpCam$^+$ tumor cells. The remaining CD45$^-$ EpCam$^-$ fraction was assumed to represent the stroma cell fraction.

HLA Ligand Isolation

HLA class I and II molecules were isolated by standard immunoaffinity purification as described previously[42]. Pan-HLA class I specific mAb W6/32 was employed for HLA class I isolation and pan-HLA class II mAb Tü39 as well as HLA-DR specific mAb L243 were used for HLA class II isolation.

Immunopeptidome Analysis by LC-MS/MS

Immunopeptidome analysis was performed on an LTQ OrbitrapXL mass spectrometer (Thermo Fisher, Waltham, Mass.) equipped with a nanoelectron spray ion source and coupled to an Ultimate 3000 RSLC Nano UHPLC System (Dionex, Sunnyvale, Calif.). Peptide samples were loaded with 3% of solvent B (20% H$_2$O, 80% acetonitrile and 0.04% formic acid) on a 2 cm PepMap 100 C18 Nanotrap column (Dionex) at a flow rate of 4 µL/min for 10 min. Separation was performed on a 50 cm PepMap C18 column with a particle size of 2 µm (Dionex) mounted in a column oven running at 50° C. The applied gradient ranged from 3 to 30% solvent B within 140 min at a flow rate of 175 nil/min. (Solvent A: 99% H$_2$O, 1% ACN and 0.1% formic acid; Solvent B: 20% H2O, 80% ACN and 0.1% formic acid). Mass spectrometry analysis was performed in data dependent acquisition mode employing a top five method (i.e. during each survey scan the five most abundant precursor ions were selected for fragmentation). Survey scans were recorded in the Orbitrap at a resolution of 60,000. MS/MS analysis was performed by collision induced dissociation (CID, normalized collision energy 35%, activation time 30 ms, isolation width 1.3 m/z) with subsequent analysis in the linear trap quadrupole (LTQ). Mass range for HLA class I ligands was limited to 400-650 m/z with possible charge states 2+ and 3+ selected for fragmentation. For HLA class II mass range was set to 300-1500 m/z allowing for fragmentation with positive charge states 2.

HLA class I samples were analyzed in 5 technical replicates while for HLA class II samples 3 technical replicates were typically acquired. Initial runs were performed without dynamic exclusion, whereas for consecutive runs a dynamic exclusion of 5 s was enabled.

Mass Spectrometry Data Processing and Analysis

MS data analysis was carried out using Proteome discoverer 1.3 (ThermoFisher). Peak lists were searched against the human proteome as comprised in the Swiss-Prot database (released Sep. 27, 2013; including 20,279 reviewed protein sequences) using Mascot search engine (Mascot 2.2.04, Matrix Science, Boston, Mass.). Mass tolerance for processing was 5 ppm for precursor ions and 0.5 Da for fragment ions. No cleavage specificity was selected and the only dynamic modification allowed was oxidized methionine. Peptide confidence was determined using percolator algorithm with a target value of q≤0.05 (5% FDR). Additional post processing filters were a Mascot Ionscore≥20, search engine rank=1 and peptide length of 8-12 amino acids for HLA class I ligands and 12-25 amino acids for HLA class II ligands. Protein grouping was disabled to ensure multiple annotations of peptides, if sequences map into multiple proteins due to conservation. HLA annotation was performed using HLA prediction algorithms hosted at SYFPEITHI and NETMHC 3.4. In case of ambiguous results multiple alleles are mentioned. For comparative profiling "one hit wonders" i.e. peptides only presented on one source with a PSM count ≤5 were removed from both of the datasets.

Label free quantitation of peptides on tumor vs. CD45$^+$ and tumor vs. stroma cells was performed using Sieve 2.1 (Thermo Fisher). At least 3 replicates of MS raw files for each cell enriched fraction as well as results from whole tissue MHC precipitations were aligned altogether with a maximum retention time (RT) shift of 2.5 mins. Frames were generated based on MS$^2$ scan events with a maximum RT width of 3.5 mins and 5 ppm mass tolerance. Identifications were imported from Proteome discoverer using Mascot search results (see above). Total ion current chromatogram normalization was used to accommodate for differences in sample intensities.

Immunogenicity Analysis of HLA Class I Ligands

Priming of peptide specific cytotoxic lymphocytes (CTLs) was conducted using an established protocol involving artificial antigen presenting cells (aAPCs) (30). aAPCs consisted of streptavidin-coated polystyrene beads (5.6 µm in diameter; Bangs Laboratories, Fishers, Ind.). Beads were resuspended at $2 \times 10^6$ particles per ml and incubated with 10 nM biotinylated peptide-MHC complexes and 10 nM stimulating anti-CD28 antibody (clone 9.3 derived from ATCC, Manassas, Va.) each for 30 min at ambient temperature. T cells were isolated from whole blood of healthy donors using a CD8 magnetic cell isolation kit (Miltenyi). One million T-cells per well were cultured in 96 well plates (Corning, Corning, N.Y., USA) and stimulated with the same number of loaded aAPCs in the presence of 5 ng/ml IL-12 (PromoCell, Heidelberg, Germany). T cells were stimulated 3 times in total with weekly stimulation interval. 40 U/ml IL-2 was added 2 days subsequent to each stimulation. T-cell priming was assessed by MHC-multimer staining one week after the last stimulation round.

Construction of Tissue Microarrays (TMA)

Consecutive paraffin embedded tumor samples of patients with high-grade serous carcinoma of the ovary or fallopian tube (EOC) with at least FIGO stage II-III and operated at the University Women's Hospital in Töbingen between 1999 and 2008 were retrieved from the archives of the Institute of Pathology. After confirmation of histological subtype and grading according to published criteria (43). 154 cases were initially included in the study. A tissue microarray (TMA) was constructed as described previously (44). We used six cores of 0.6 mm diameter of each patient (maximum three cores each from two different sites of the primary tumors—at least two separate cores). In addition we constructed a TMA using paraffin embedded tissue from the primary tumors of the prospectively collected cases for ligandome analysis. 3 µm thick sections were cut, rehydrated and subjected to specific pretreatment for immunohistochemistry. In total 23 cases were evaluable for immunoscoring and correlation with immunopeptidome data.

Immunohistochemistry

The following primary antibodies and dilutions were used for immunohistochemistry: CD3 (1:100, rat monoclonal SP7, DCS, Hamburg, Germany), CD8 (1:200, mouse monoclonal C8/144B, DAKO), MUC16 (1:450, mouse monoclonal M11, DAKO, Glostrup, Denmark), IDO1 (1:25, mouse monoclonal, ABCAM, Cambridge, UK) and MSLN (1:100, mouse monoclonal SPM143, GeneTex, Irvine, Calif., USA). The tissue sections were pre-treated with EDTA-buffer solution (pH 8.6) at 95° C. for 36 min. Immunohistochemical staining was performed on an automated immunostainer according to the manufacturer's instructions using the iView DAB detection kit (both Ventana, Tucson, Ariz., USA).

Immunoscoring

Quantification of TILs was carried out by first assessing the average number of immunostained cells per high power field (HPF=400×) by counting at least 2 HPF for each core. In a second step, the average number of lymphocytes per HPF for the left and right triple core set was calculated, and for all cores together. This bilateral average count was used for further calculations. The fibro vascular tumor stroma (CD3S and CD8S), and the intraepithelial compartment of the tumor (CD3E and CD8E) were evaluated separately.

For expression of CA 125, IDO1 and MSLN staining intensity was graded from 0-3, multiplied by a score from 1-4 for the percentage of tumor cells (1: 0-10%; 2: 10-50%; 3: 50-80%; 4: 80-100%). For all parameters the cases were separated in quartiles and the best separation between two quartiles defined as cut-off value between high and low expression. Of the 154 cases on the TMA 71 patients had undergone documented optimal tumor debulking (<1 cm residual tumor mass) and could be successfully evaluated for TILs and expression of proteins. Immunoscoring and clinical data analysis were performed by independent investigators.

Statistical Analysis/Visualization

If not mentioned otherwise all figures and statistical analyses were generated using Graphpad Prism 6.0 (Graphpad software, La Jolla, Calif., USA) or Microsoft Office 2010 (Microsoft). Word clouds were created using an online applet. Kaplan-Meier analysis was performed using SPSS statistical software (Version 21, IBM Corp., Armonk, N.Y., USA). Two-tailed unpaired student's t-test was performed unless otherwise specified. P values less than 0.05 were considered statistically significant. D'Agostino-Pearson omnibus test was used to verify normality and the F-Test was used to verify equal variance. For FIGS. 1A and 1B the two-tailed unpaired Student's t-test with Welch's correction was used owing to unequal variance between the two comparison groups. Non-parametric Mann-Whitney-test was used in FIGS. 4A-4D because normal distribution could not be assessed in all cases due to small sample sizes. Spearman correlation was used to correlate IHC scores of MSLN and MUC16 as the datasets were not showing normal distribution. P values comparing two Kaplan-Meier survival curves in FIGS. 5A-5C were calculated using the log-rank (Mantel-Cox) test in Graphpad Prism.

Example 1: HLA Count on Cell Surface and HLA Typing

A major prerequisite for the development of T-cell mediated immunotherapies is the expression of MHC molecules on the surface of tumor cells. Therefore, the inventors analyzed and quantified the number of HLA-A, B, C as well as HLA-DR molecules by flow cytometry on different cell subsets of ovarian tumors (n=11) as well as benign tissues from ovary and fallopian tube (n=8) obtained by enzymatic dissociation. The analysis aimed at the separate quantification of cell type specific HLA expression for leukocytes ($CD45^+$), tumor/epithelial cells (Epcam+), and endothelial cells ($CD31^+$; the latter only in a subset of 7 ovarian tumors). For the complete gating strategy see FIG. 6. The median number of HLA molecules per cell was heterogeneous both among different cell types and individual patients, ranging from ~5,000 to 150,000 HLA class I and ~500 to 330,000 HLA-DR molecules. The number of HLA-A, B, and C molecules was significantly higher (p=0.0205) on leukocytes isolated from tumor vs. benign tissue indicating an ongoing inflammatory reaction within the tumor. Strong differences in HLA class I expression were also seen when comparing tumor cells with epithelial cells derived from benign tissues. HLA class I molecule expression was significantly (p=0.0021) higher on tumor cells (~75,000 molecules/cell) but remained in the range of other stromal cells such as endothelial cells (~95,000 molecules/cell). Surprisingly the inventors evidenced a strong (~105,000 molecules/cell) to some extent extraordinarily high expression of HLA-DR on EOC cells (>300,000 molecules/cell), whereas benign epithelial cells were virtually negative for HLA-DR (p=0.0108). Altogether, the inventors could observe an increased MHC class I and class II expression within the tumors.

HLA ligandome analysis and comparative profiling reveal EOC specific antigen presentation. In order to map the HLA ligand repertoire of EOC the inventors isolated HLA molecules from bulk tumor tissue and performed mass spectrometry to characterize the HLA ligandome for a total of 34 EOCs (for patient characteristics and HLA typing see Table 7).

TABLE 7

| OvCa ID | Age | Tumor Type | TNM Staging | HLA typing MHC class I | HLA typing MHC class II |
|---|---|---|---|---|---|
| OvCa 9 | 65 | serous ovarian carcinoma | T3cNxM1G2 R1 | A*02:01, A*03:01, B*07:02, B*40:02, C*07:02, C*12:01 | DQB1*03:01, DQA1*03:01, DQA1*05:01, DRB1*11:01, DRB1*04:01, DRB3*02:02, DRB4*01:01, DPB1*02:01, DPB1*13:01 |
| OvCa 10 | 60 | serous ovarian carcinoma | T3bN1M1G2 R1 | A*02:01, A*11:01, B*44:05, B*51:01, C*02:02, C*15:02 | DQB1*02:02, DQB1*05:01, DQA1*01:01, DQA1*03:01, DRB1*01:01, DRB1*09:01, DRB4*01:01, DPB1*04:01, DPB1*05:01 |
| OvCa 12 | 62 | serous ovarian carcinoma | T3cN0G2R0 | A*24:02, A*31:01, B*35:03, B*49:01, C*07:01, C*12:03 | DQB1*03:01, DQB1*05:04, DQA1*01:02, DQA1*03:01, DRB1*01:01, DRB1*04:01, DRB4*01:01, DPB1*02:01, DPB1*05:01 |
| OvCa 13 | 62 | serous ovarian carcinoma | T1cN1G3R0 | A*02, B*35, B*40, C*03, C*04 | DQB1*04, DQB1*06, DRB1*08, DRB1*13 |
| OvCa 15 | 75 | serous ovarian carcinoma | T3cN0G3R0 | A*11:01, A*24:02, B*07:02, B*55:01, C*03:03, C*07:02 | DQB1*03:01, DQA1*05:01, DRB1*11:01, DRB1*03:17, DRB3*02:02, DPB1*03:01 |
| OvCa 16 | 45 | serous ovarian carcinoma | T3bN1G3R0 | A*02, B*40, B*44, C*03, C*05 | DQB1*06, DRB1*08, DRB1*13, DRB1*14, DRB3 |
| OvCa 23 | 29 | serous ovarian carcinoma | T3aN1G3R0 | A*01, A*03, B*08, B*35, C*04, C*07 | DQB1*02, DQB1*03, DRB1*03, DRB1*12, DRB3 |
| OvCa 28 | 66 | serous ovarian carcinoma | T2bN0G3R0 | A*01:01, A*02:01, B*27:05, B*52:01, C*01:02, C*02:02 | DQB1*05:01, DQB1*06:01, DQA1*01:01, DQA1*03:01, DRB1*01:03, DRB1*15:02, DRB5*01:02, DPB1*04:01 |
| OvCa 39 | 45 | serous ovarian carcinoma | T3cN1G3R1 | A*25:01, A*31:01, B*07:02, B*18:01, C*12:03, C*07:02 | DQB1*06:02, DQA1*01:02, DRB1*15:01, DRB1*16:09, DRB5*01:01, DRB5*01:11, DPB1*04:01, DPB1*04:02 |
| OvCa 41 | 66 | serous and endometrial ovarian carcinoma | T3cN0G3R1 | A*02, A*24, B*18, B*51, C*02, C*12 | DQB1*03, DQ7, DRB1*11, DRB3 |
| OvCa 43 | 61 | serous ovarian carcinoma | T3cN1G3R2 | A*02, A*32, B*18, B*35, C*04, C*07 | DQB1*03, DQB1*05, DQ9, DRB1*01, DRB1*07, DRB4 |
| OvCa 45 | 63 | mixed differentiated (mostly endometroid) ovarian carcinoma | T1cN0G3R0 | A*01, A*23, B*08, B*44, C*04, C*07 | DQB1*02, DRB1*03, DRB1*07, DRB3, DRB4 |
| OvCa 48 | 71 | serous ovarian carcinoma | T3cN1G3R0 | A*02:01, A*25:01, B*15:01, B*41:02, C*03:04, C*17:01 | DQB1*03:02, DQB1*03:04, DQA1*03:01, DRB1*04:01, DRB1*13:03, DRB3*01:01, DRB4*01:01, DPB1*02:01 |
| OvCa 53 | 48 | serous ovarian carcinoma | T3bN1G3R0 | A*02, A*03, B*27, B*35, C*02, C*04 | DQB1*02, DQB1*03, DQ7, DRB1*03, DRB1*11, DRB3 |

TABLE 7-continued

| OvCa ID | Age | Tumor Type | TNM Staging | HLA typing MHC class I | HLA typing MHC class II |
|---|---|---|---|---|---|
| OvCa 54 | 66 | serous ovarian carcinoma | T3cN1M1G3 R2 | A*02:01, A*11:01, B*35:01, B*35:03, C*04:01, C*12:03 | DQB1*05:01, DQB1*05:03, DQA1*01:01, DRB1*01:03, DRB1*14:01, DRB3*02:02, DPB1*04:01, DPB1*02:01 |
| OvCa 57 | 58 | endometrioid ovarian carcinoma | T1cN0G1R0 | A*25, A*32, B*15, B*18, C*03, C*12 | DQB1*05, DQB1*06, DRB1*01, DRB1*15, DRB5 |
| OvCa 58 | 74 | serous ovarian carcinoma | T3cN1G3R1 | A*02, A*03, B*35, C*03, C*04 | DQB1*05, DRB1*01 |
| OvCa 59 | 47 | serous ovarian carcinoma | T3cN1G3R2 | A*03, A*30, B*13, C*06 | DQB1*02, DDRB1*07, DRB4 |
| OvCa 60 | 50 | serous ovarian carcinoma | T3cN1G3R1 | A*24:02, A*25:01, B*13:02, B*18:01, C*12:03, C*06:02 | DRB1*08:01, DRB1*13:01, DQB1*04:02, DQB1*06:03, DQA1*04:01, DQA1*01:03, DPB1*02:01, DPB1*03:01 |
| OvCa 64 | 56 | serous ovarian carcinoma | T3cN1G3R1 | A*01, A*25, B*08, C*07 | DQB1*02, DRB1*03, DRB3 |
| OvCa 65 | 55 | serous ovarian carcinoma | T3cN1M1G3 R1 | A*01, A*24, B*15, B*35, C*04, C*14 | DQB1*03, DQB1*05, DRB1*10, DRB1*11, DRB3 |
| OvCa 66 | 73 | serous ovarian carcinoma | T2bN0G3R0 | A*11:01, A*29:02, B*18:01, B*44:03, C*05:01, C*16:01 | DRB1*03, DRB*0701, DRB3*0202, DRB4*0101, DQB1*02:01, DQB1*02:02, DQA1*02:01, DQA1*05:01, DPB1*02:02, DPB1*03:01 |
| OvCa 68 | 69 | serous ovarian carcinoma | T3cN1G3R1 | A*02:01, A*01:01, B*44:02, B*37:01, C*06:02, C*05:01 | DRB1*10:01, DRB1*04:01, DRB4*04:01, DQB1*05:01, DQB1*03:01, DQA1*01:01, DPB1*04:01 |
| OvCa 69 | 68 | serous ovarian carcinoma | T3cN0G1R1 | n/a | n/a |
| OvCa 70 | 48 | serous ovarian carcinoma | T3cN1M1G1 R1 | A*01, A*02, B*07, C*07 | DQB1*03, DQB1*05, DRB1*09, DRB1*14, DRB3, DRB4 |
| OvCa 72 | 53 | serous ovarian carcinoma | T3bN1G3R0 | A*03:01, A*01:01, B*08:01, B*07:02, C*07:02, C*07:01 | DRB1*01:01, DRB1*03:01, DRB3*01:01, DQB1*05:01, DQB1*02:01, DQA1*01:01, DPB1*04:01 |
| OvCa 73 | 69 | serous ovarian carcinoma | T3cN1G3R0 | A*01:01, B*08:01, C*07:01 | DRB1*03:01, DRB1*03:42, DRB3*01:01, DRB3*01:14, DQB1*02:01, DQA1*05:01, DPB1*04:01 |
| OvCa 74 | 79 | endometrioid ovarian carcinoma | T3bNxG1R1 | A*02:01, B*18:01, B*51:01, C*07:02, C*15:02 | DRB1*11:04, DRB1*07:01, DRB3*02:02, DRB4*01:01, DQB1*03:01, DQB1*02:02, DQA1*02:01, DQA1*05:01, DPB1*04:02, DPB1*02:01 |
| OvCa 79 | 57 | endometrioid ovarian carcinoma | T2bN0G2R0 | A*01:01, A*31:01, B*08:01, B*51:01, C*07:01, C*15:02 | DQB1*03:03, DQA1*02:01, DRB1*07:01, DRB1*09:01, DRB4*01:01, DPB1*13:01, DPB1*02:01 |
| OvCa 80 | 93 | serous ovarian carcinoma | T3cNxG3R2 | A*25:01, A*32:01, B*18:01, B*39:01, C*12:03 | DRB1*01:01, DRB1*12:01, DRB3*02:02, DQB1*03:01, DQB1*05:01, DQA1*01:01, DQA1*05:01, DPB1*04:01 |
| OvCa 81 | 78 | serous ovarian carcinoma | T3cNxG3R2 | A*02:01, B*45:01, B*56:01, C*07:02, C*01:02 | DRB1*04:02, DRBB1*11:01, DRB4*01:01, DRB3*02:02, DQB1*03:01, DQB1*03:02 |

TABLE 7-continued

| OvCa ID | Age | Tumor Type | TNM Staging | HLA typing MHC class I | HLA typing MHC class II |
|---|---|---|---|---|---|
| OvCa 82 | 48 | serous ovarian carcinoma | T3cN1G3R0 | A*01:01, A*03:01, B*08:01, B*38:01, C*07:01, C*12:03 | DRB1*04:02, DRB1*03:01, DRB4*01:01, DRB3*01:01, DQB1*02:01, DQB1*03:02, DQA1*03:01, DQA1*05:01, DPB1*04:01, DPB1*13:01 |
| OvCa 83 | 50 | serous ovarian carcinoma | T1cN0G2R0 | A*02, A*11, B*51, B*55, C*03, C*15 | DQB1*03, DQB1*05, DRB1*09, DRB1*14, DRB3, DRB4 |
| OvCa 84 | 70 | serous ovarian carcinoma | T3cN1G3R1 | A*02:01, B*07:02, B*44:02, C*07:02, C*05:01 | DRB1*15:01, DRB5*01:01, DQB1*06:02, DQA1*01:02, DPB1*04:01, DPB1*4:02 |

For MHC class I the inventors could identify 22,920 unique peptides (mean 1,263/sample) emanating from 9,136 different source proteins (mean 1,239/sample) reaching >90% of the estimated maximal attainable coverage (see FIG. 7A).

Example 2, Identification of Top Cancer Associated HLA Ligands

Aiming to extract the most specific HLA ligands for EOC from this vast catalogue of data the inventors compared the HLA ligand source proteins with an in-house database of benign sources ("HLA benign ligandome database") consisting of samples from PBMCs (n=30), bone marrow (n=10), liver (n=15), colon (n=12), ovary (n=4) and kidney (n=16). The HLA benign ligandome database contains 31,032 peptides representing 10,012 source proteins and was established using blood or bone marrow from healthy donors as well as histopathologically evaluated normal tissues, all analyzed with exactly the same pipeline as used for EOCs. For comparative profiling "one hit wonders" (i.e. peptides only presented on one source with low PSM count) were removed from both datasets to accommodate for false positive hits. Comparative analysis of the two respective datasets (see FIG. 2A) revealed 379 MHC class I source proteins to be presented exclusively by EOC in at least three of the tested patients, highlighting an EOC specific HLA peptide repertoire. The TOP100 EOC specific source proteins ranked according to their frequency of presentation are visualized in FIG. 2B. The most important EOC specific HLA ligand source protein yielded by this analysis was mucin 16 (MUC16) also known as cancer antigen 125 (CA-125). Overall more than 80 different MUC16 derived HLA ligands (see Table 8) were presented in nearly 80% of patients (26/34).

TABLE 8

| Sequence | ID No. | Sources | HLA |
|---|---|---|---|
| AHSKITTAM | 3 | OvCa 80 | B*39:01 |
| AVKTETSTSER | 4 | OvCa 12, OvCa 79 | A*31:01 |
| AVTNVRTSI | 5 | Ovca 59, OvCa 60 | B*13 |
| DALTPLVTI | 6 | OvCa 74 | B*51:01 |
| DALVLKTV | 7 | OvCa 41, OvCa 74, OvCa 79, OvCa 83 | B*51 |
| DPYKATSAV | 8 | OvCa 10, OvCa 41, OvCa 69 OvCa 74, OvCa 79, OvCa 83 | B*51 |
| EPETTTSFITY | 9 | OvCa 65 | B*35 |
| ERSPVIQTL | 10 | OvCa 80 | B*39:01 |
| ETILTFHAF | 11 | OvCa 48, OvCa 64, OvCa 80 | A*25 |
| EVISSRGTSM | 12 | OvCa 48, OvCa 60, OvCa 64, OvCa 80 | A*25 |
| EVITSSRTTI | 13 | OvCa 60, Ovca 64 | A*25 |
| EVTSSGRTSI | 14 | OvCa 60, Ovca 64, OvCa 80 | A*25 |
| FPEKTTHSF | 15 | OvCa 65 | B*35 |
| FPHSEETTTM | 16 | OvCa 13, OvCa 65 | B*35 |
| FPHSEITTL | 17 | OvCa 12, OvCa 13, OvCa 53 | B*35 |

TABLE 8-continued

| Sequence | ID No. | Sources | HLA |
|---|---|---|---|
| FQRQGQTAL | 18 | OvCa 48 | B*15:01 |
| GDVPRPSSL | 19 | OvCa 72 | B*08:01 |
| GHESHSPAL | 20 | OvCa 80 | B*39:01 |
| GHTTVSTSM | 21 | OvCa 80 | B*39:01 |
| GTHSPVTQR | 22 | OvCa 39, OvCa 79 | A*31:01 |
| GTSGTPVSK | 23 | OvCa 83 | A*11 |
| HPDPQSPGL | 24 | OvCa 65 | B*35 |
| IITEVITRL | 547 | OvCa 83 | A*02 |
| IPRVFTSSI | 25 | OvCa 41, OvCa 74 | B*51 |
| ISDEVVTRL | 26 | OvCa 16 | C*05 |
| ISIGTIPRI | 27 | OvCa 65 | B*15:17 |
| ISKEDVTSI | 28 | OvCa 65 | B*15:17 |
| ITETSAVLY | 29 | OvCa 65 | A*01 |
| ITRLPTSSI | 30 | OvCa 65 | B*15:17 |
| KDTAHTEAM | 31 | OvCa 68 | B*44:02 |
| KEDSTALVM | 32 | OvCa 16 | B*40/B*44 |
| KEVTSSSSVL | 33 | OvCa 16, OvCa 70 | B*40/B*44/? |
| KMISAIPTL | 548 | OvCa 81, OvCa 83 | A*02 |
| LPHSEITTL | 34 | OvCa 12, OvCa 13 | B*35 |
| LTISTHKTI | 35 | OvCa 65 | B*15:17 |
| LTKSEERTI | 36 | OvCa 65 | B*15:17 |
| QFITSTNTF | 1 | OvCa 60 | A*24:02 |
| RDSLYVNGF | 37 | OvCa 68 | B*44:02 |
| RETSTSQKI | 38 | OvCa 60 | B*18:01 |
| RSSGVTFSR | 39 | OvCa 79 | A*31:01 |
| SAFESHSTV | 40 | OvCa 41, OvCa 74, OvCa 79, OvCa 83 | B*51 |
| SATERSASL | 41 | OvCa 13, OvCa 16, OvCa 70 | C*03/? |
| SENSETTAL | 42 | OvCa 16, OvCa 70 | B*40/B*44/? |
| SEQRTSPSL | 43 | OvCa 70 | n.a. |
| SESPSTIKL | 44 | OvCa 13, OvCa 70 | B*40/? |
| SPAGEAHSL | 45 | OvCa 72, OvCa 81, OvCa 84 | B*07/B*56 |
| SPAGEAHSLLA | 46 | OvCa 81 | B*56:01 |
| SPHPVSTTF | 47 | OvCa 84 | B*07:02 |
| SPHPVTALL | 48 | OvCa 9, OvCa 72, OvCa 84 | B*07:02 |
| SPLFQRSSL | 49 | Ovca 72 | B*0702 |
| SPQNLRNTL | 50 | OvCa 23, OvCa 72, OvCa 84 | B*35/B*07:02 |
| SPRLNTQGNTAL | 51 | OvCa 72, Ovca 84 | B*07:02 |
| SPSEAITRL | 52 | Ovca 84 | B*07:02 |

TABLE 8-continued

| Sequence | ID No. | Sources | HLA |
|---|---|---|---|
| SPSKAFASL | 53 | OvCa 9, OvCa 23, OvCa 39, OvCa 69, OvCa 72, OvCa 84 | B*35/B*07:02 |
| SPSSPTPKV | 54 | OvCa 72 | B*07:02 |
| SPSSQAPVL | 55 | OvCa 84 | B*07:02 |
| SQGFSHSQM | 56 | OvCa 48 | B*15:01 |
| SRTEVISSR | 57 | OvCa 53 | B*27 |
| SSAVSTTTI | 58 | OvCa 65 | B*15:17 |
| SSPLRVTSL | 59 | OvCa 69 | n.a. |
| STASSSLSK | 60 | OvCa 83 | A*11 |
| STETSTVLY | 2 | OvCa 64, OvCa 65, OvCa 68 | A*01 |
| STQRVTTSM | 61 | OvCa 72 | n.a. |
| STSQEIHSATK | 62 | OvCa 83 | A*11 |
| SVLADLVTTK | 63 | OvCa 72 | A*03:01 |
| SVPDILSTSW | 64 | OvCa 60 | A*24:02 |
| TAGPTTHQF | 65 | OvCa 58 | C*03 |
| TEISSSRTSI | 66 | OvCa 12 | B*49:01 |
| TENTGKEKL | 67 | OvCa 16 | B*40/B*44 |
| TETEAIHVF | 68 | OvCa 41, OvCa 80 | B*18 |
| TEVSRTEVI | 69 | OvCa 12 | B*49:01 |
| TExVLQGLL | 70 | OvCa 16, OvCa 66, OvCa 70 | B*40/B*44/? |
| TPGGTRQSL | 71 | OvCa 9, OvCa 23, OvCa 39, OvCa 72, OvCa 84 | B*07:02/B*35 |
| TPGNRAISL | 72 | OvCa 23, OvCa 72, OvCa 84 | B*07:02/B*35 |
| TPNSRGETSL | 73 | OvCa 72 | B*07:02 |
| TSGPVTEKY | 74 | OvCa 58 | B*35 |
| TSPAGEAHSL | 75 | OvCa 81 | n.a. |
| TTLPESRPS | 324 | OvCa 70 | n.a. |
| TYSEKTTLF | 549 | OvCa 12, OvCa 41, OvCa 60, OvCa 65 | A*24 |
| VHESHSSVL | 76 | OvCa 80 | B*39:01 |
| VPRSAATTL | 77 | OvCa 23, OvCa 72, OvCa 84 | B*07:02/B*35 |
| VTSAPGRSI | 78 | OvCa 65 | B*15:17 |
| VTSSSRTSI | 79 | OvCa 65 | B*15:17 |
| YPDPSKASSAM | 80 | OvCa 65 | B*35 |

Those data highlight the frequent processing and presentation of MUC16 by a multitude of different HLA allotypes unparalleled by any other EOC specific antigen and mirrored only by frequently (>95%) presented house-keeping proteins such as beta actin (overall 149 different peptides identified). Among the TOP100 EOC specific source proteins other well established tumor associated antigens like MUC1 or KLK10 as well as antigens with well documented immune-evasive functions like Indoleamine-2,3-dioxygenase (IDO1) or Galectin 1 (LGALS1) were identified.

Figure 2A:
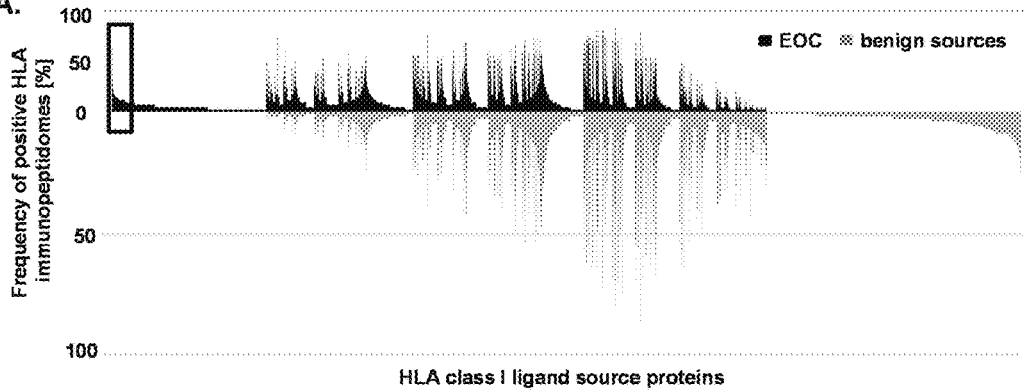
FIGS. 2A-2D describe an embodiment as described herein.
Figure 2B:
Figure 2C:
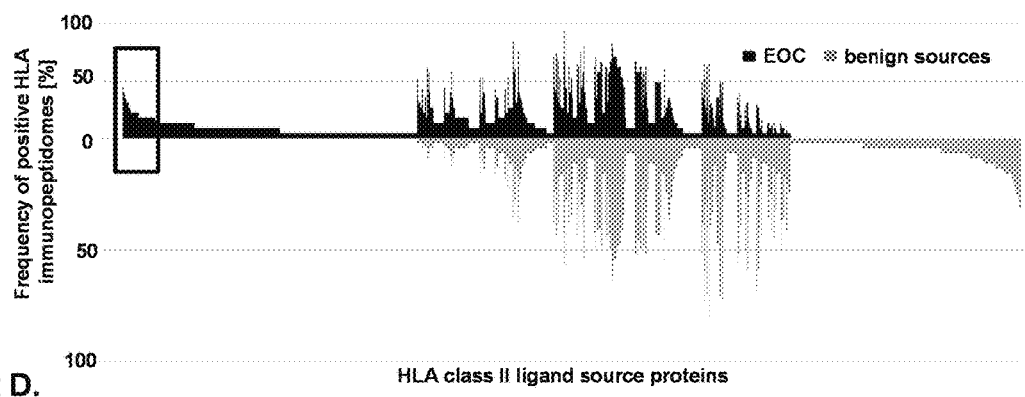
Figure 2D:

Owing to the power of CD4 T cells in supporting or driving an anti-tumor immune response the inventors used the same approach to further analyze MHC class II presented peptides in EOC (n=22) yielding 9,162 peptides (mean 598/sample) representing 2,330 source protein (mean 319/sample) reaching >80% of attainable coverage (see FIG. 7B). The HLA benign ligand dataset for MHC class II contained 7,267 peptides representing 1,719 source proteins derived from bone marrow (n=5), PBMCs (n=13), colon (n=2), liver (n=7) and kidney (n=17). Analysis of the TOP100 MHC class II presented antigens revealed a more heterogeneous and complex picture (FIG. 2C). Notably, MHC presented peptides of mesothelin (MSLN) an established ligand of MUC16, could be identified in nearly 50% of patients (10/22; FIG. 2D). MUC16 itself was not among the TOP100 class II antigens but respective ligands could nevertheless be detected in four patients.

Besides the TOP100 EOC specific HLA ligand source proteins, the inventors further looked for established cancer-testis and tumor associated antigens that have been previously employed for clinical application to verify their abundance (Her2neu, WT1, NY-ESO-1, hTert and p53). Although the inventors could identify HLA presented peptides for all antigens except for NY-ESO-1, none of them were exclusively presented on EOC (Table 9). The only ligands showing EOC specific presentation, albeit with low frequency (3/34), were HLA class I ligands (but not HLA class II) from Her2neu.

TABLE 9

| SEQ ID | Her2neu | HLA restriction | Sources of presentation |
|---|---|---|---|
| | ERBB2 (Receptor tyrosine-protein kinase erbB-2) | | |
| 554 | TYLPTNASLSF | A*23/A*24 | 2x OvCa |
| 153 | MPNPEGRYTF | B*35 | 1x OvCa |
| 152 | AARPAGATL | B*07 | 1x OvCa |
| 291 | AIKVLRENTSPKANKE | HLA class II | 1x OvCa |
| 292 | DPSPLQRYSEDPTVPLPS | HLA class II | 2x OvCa |
| 293 | DPSPLQRYSEDPTVPLPSE | HLA class II | 1x OvCa |
| 294 | ELVSEFSRMARD | HLA class II | 2x PBMCs |
| 295 | ELVSEFSRMARDPQ | HLA class II | 2x PBMCs, 1x Kidney |
| 296 | IPVAIKVLRENTSPKANKE | HLA class II | 1x OvCa |
| 297 | RRLLQETELVEPLTPS | HLA class II | 2x Liver |
| 298 | SPQPEYVNQPDVRPQPP | HLA class II | 1x OvCa |
| 291 | VKPDLSYMPIWKFPDE | HLA class II | 1x OvCa |
| | WT-1 Wilms tumor protein | | |
| 558 | RMFPNAPYL | A*02 | 8x PBMCs, 1x Liver |
| 557 | QRNMTKLQL | B*13 | 2x OvCa, 1x Liver, 1x PBMCs |
| 555 | GVFRGIQDV | B*13 | 2x OvCa |
| 550 | ALLPAVPSL | A*02 | 1x OvCa |
| | hTert Telomerase reverse transcriptase | | |
| 556 | LMSVYVVEL | A*02 | 2x PBMCs |
| | p53 Cellular tumor antigen p53 | | |
| 552 | RPILTIITL | B*07 | 4x PBMCs, 2x Liver, 2x Kidney, 3x OvCa |
| 553 | TYSPALNKMF | A*24 | 1x PBMCs, 1x Liver, 2x OvCa |

TABLE 9-continued

| SEQ ID | Her2neu | HLA restriction | Sources of presentation |
|---|---|---|---|
| 551 | GRNSFEVRV | B*27 | 1x PBMC, 1x Liver, 1x Kidney, 1x OvCa |

Example 3: Cellular Origin of EOC Associated HLA Presented Peptides

Since EOCs embody not only cancer cells but rather represent a heterogeneous mixture of different cell types the inventors asked, whether the MHC class I TOP100 antigens were indeed originally presented by cancer cells. For this purpose the inventors digested EOCs and separated CD45+ leukocytes, EpCam+ tumor cells as well as stroma cells negative for the two markers (for enrichment efficiencies see Table 10) and subsequently the inventors performed HLA ligandomics individually for each of the subsets.

TABLE 10

Cell enrichment efficiencies:
Percentage of cells are given in each fraction
before (PreSort) and after MACSorting

| OVCa | PreSort | | | CD45+ fraction | | |
|---|---|---|---|---|---|---|
| | CD45+ | EpCam+ | Viability | CD45+ | EpCam+ | Viability |
| 84 | 74.7 | 18.3 | 80.2 | 93.5 | 6.2 | 71.6 |
| 73 | 23.1 | 12.3 | 81.2 | 95.7 | 1.7 | 77.2 |
| 70 | 76.2 | 8.83 | 78.9 | 96 | 1.3 | 82.7 |
| 60 | 77.4 | 5.2 | 92.3 | 94.8 | 1.7 | 90.2 |
| 57 | 31.9 | 50.5 | 94.1 | 93.6 | 5.0 | 90.6 |

| OVCa | EpCam+ fraction | | | EpCam− fraction | | |
|---|---|---|---|---|---|---|
| | CD45+ | EpCam+ | Viability | CD45+ | EpCam+ | Viability |
| 84 | 10.7 | 85.7 | 88.2 | 4.5 | 22.1 | 64.0 |
| 73 | 3.4 | 73.3 | 87.6 | 1.7 | 3.2 | 87.4 |
| 70 | 3.4 | 94 | 66.4 | 3.1 | 4.5 | 65.4 |
| 60 | 5.2 | 79.7 | 88.7 | 3.8 | 10.7 | 89.5 |
| 57 | 1.4 | 95.3 | 96.7 | 0.8 | 7.2 | 95.3 |

The inventors used label free quantification to determine the source of each identified HLA ligand in a total of 5 EOCs (for a representative example see FIGS. 3A and 3B). As expected, MUC16 derived HLA ligands, identified on (4/5) EOC samples, were always found to be overrepresented on enriched cancer cells with a median 5 fold overrepresentation (range 1.8-135 fold) dependent on the efficiency of the enrichment. The same held true for several other frequently presented TOP100 antigens like DDR1, SOX9, CRABP1/2, EYA2, LAMC2, MUC1 or KLK10. However a number of other antigens especially those known to be upregulated by interferon such as toll like receptors (TLR3, TLR7) or 2'-5'-oligoadenylate synthase-like protein synthase (OASL) could not be unambiguously shown to be presented by tumor cells but rather displayed strong overrepresentation on CD45+ leukocytes and/or stroma cells. Apart from tumor associated antigens the inventors also recognized ligands from source proteins with cell type specific expression. For example ligands derived from CD8, CD132 or lymphocyte specific protein 1 (LSP1) were found highly overrepresented on CD45+ cells and van Willebrand factor (vWF) most likely expressed by endothelial cells in the stroma was found highly overrepresented within the stromal subset emphasizing the strength of this cell type specific approach.

Example 4: Immunogenicity Analysis of MUC16 Derived Ligands

For the applicability of peptide vaccines immunogenicity is a major imperative. In order to evaluate the immunogenic potential of the identified HLA ligands the inventors used a T-cell priming protocol involving artificial antigen presenting cells and T cells isolated from blood of healthy donors. The results of this analysis for the number one EOC associated antigen MUC16 are presented in Table 11. Among 23 different peptides tested so far, 18 were shown to be immunogenic in at least ⅓ donors. This nearly 80% recognition rate verifies the presence of naïve MUC16 recognizing T cells in the human population. Similar results have been obtained for other TOP100 antigens (e.g. IDO1, LGALS1).

TABLE 11

Immunogenicity analysis of EOC presented HLA
ligands from MUC16/CA-125

| HLA | Sequence | SEQ ID | positive/tested donors |
|---|---|---|---|
| A*01 | STETSTVLY | 2 | 0/2 |
| A*02 | IITEVITRL | 547 | 3/10 |
| A*02 | KMISAIPTL | 548 | 4/6 |
| A*03 | SVLADLVTTK | 63 | 0/1 |
| A*11 | STSQEIHSATK | 62 | 2/6 |
| A*11 | GTSGTPVSK | 23 | 0/5 |
| A*24 | TYSEKTLLF | 549 | 2/2 |
| A*24 | AVTNVRTSI | 5 | 1/3 |
| A*25 | ETILTFHAF | 11 | 2/2 |
| A*25 | EVITSSRTTI | 13 | 1/1 |
| A*25 | EVTSSGRTSI | 14 | 2/3 |
| A*25 | EVISSRGTSM | 12 | 1/3 |
| B*07 | SPHPVTALL | 48 | 0/1 |
| B*07 | SPQNLRNTL | 50 | 1/1 |
| B*07 | LPHSEITTL | 34 | 0/2 |
| B*07 | SPSKAFASL | 53 | 2/2 |
| B*07 | VPRSAATTL | 77 | 1/2 |
| B*07 | TPGNRAISL | 72 | 2/2 |
| B*15 | SQGFSHSQM | 56 | 4/5 |
| B*15 | FQRQGQTAL | 18 | 1/6 |
| B*27 | ERSPVIQTL | 10 | 1/2 |

TABLE 11-continued

Immunogenicity analysis of EOC presented HLA
ligands from MUC16/CA-125

| HLA | Sequence | SEQ ID | positive/ tested donors |
|---|---|---|---|
| B*51 | DALVLKTV | 7 | 1/3 |
| B*51 | DPYKATSAV | 8 | 3/3 |
| 8/10 allotypes | 18/23 HLA ligands | | 34/73 |

Example 5: Biomarkers for HLA Ligand Presentation

Antigen specific cancer immunotherapy (e.g. peptide vaccination, adoptive T-cell transfer) requires a stringent selection of candidate antigens within a short timeframe. HLA ligandome analysis however, is not always possible due to the lack of appropriate material. A feasible alternative would be the use of biomarkers to predict the presence of HLA ligands on the tumor cells. In order to evaluate whether, protein expression analyzed by immunohistochemistry (immunoreactivity score, IRS) could serve as a surrogate marker for HLA ligand presentation, the inventors analyzed the TOP100 MHC class I antigens MUC16 and IDO1 as well as the TOP100 MHC class II antigen MSLN by immunohistochemistry and correlated the staining intensity (FIG. 4A) to the presence or absence of HLA ligands on the same tumors. For both MUC16 and MSLN, staining scores were significantly higher on tumors, which presented HLA ligands of respective source proteins (FIG. 4C). The same was true for CA-125 serum levels determined at the day of surgery (FIG. 4D), indicating that these parameters could be used for a proper selection of candidate antigens for peptide vaccination. In contrast, IDO1 did not show a significant association with ligand presentation.

Example 6: Prognostic Relevance of the MUC16/MSLN Axis

Because of their importance as targets for immunotherapy the inventors wanted to assess whether MSLN and MUC16 are also of prognostic relevance in a patients similar to our immunopeptidome collective. For this purpose the inventors analyzed the expression of both antigens as well as the extent of T-cell infiltration by immunohistochemistry in a tissue microarray (TMA) of high grade serous ovarian cancers (FIGO stage II-III). In order to avoid prognostically relevant confounders the inventors restricted our analysis to 71 patients with optimally debulked cancers (residual mass below <1 cm).

While the inventors did not observe any prognostic effect for MUC16 staining, strong MSLN staining was associated with a notable borderline significant (p=0.0572) decrease of median overall survival from 50 to 28 months (FIG. 5A). Despite their different prognostic relevance, staining scores for MUC16 and MSLN showed a direct and highly significant correlation (Spearman correlation coefficient r=0.5237; 95% c.i.=0.3159-0.6835, two tailed significance p<0.001).

For the evaluation of T-cell infiltration the inventors assessed the number of CD3 T cells in the intraepithelial compartment of the tumor (CD3E) and the fibrovascular stroma (CD3S) separately. Notably only the number of intraepithelial T cells showed a significant (p<0.0063) prognostic impact, whereas infiltration of the surrounding stroma alone had no prognostic relevance (FIG. 5B). Only in a subgroup analysis combining MSLN and CD3 staining a significant prognostic benefit for tumors with low MSLN and high T-cell infiltration could be observed (FIG. 5C) for both CD3E (p<0.001) and CD3S (p<0.0049). Most strikingly, the combination of high intratumoral T-cell infiltration (CD3E) and low MSLN staining defined a subset of long term cancer survivors (10/11 patients with confirmed survival beyond 3 years).

REFERENCES AS CITED

Allison, J. P. et al., Science 270 (1995)
Andersen, R. S. et al., Nat. Protoc. 7 (2012)
Appay, V. et al., Eur. J Immunol. 36 (2006)
Banchereau, J. et al., Cell 106 (2001)
Beatty, G. et al., J Immunol 166 (2001)
Beggs, J. D., Nature 275 (1978)
Benjamini, Y. et al., Journal of the Royal Statistical Society. Series B (Methodological), Vol. 57 (1995)
Boulter, J. M. et al., Protein Eng 16 (2003)
Braumuller, H. et al., Nature (2013)
Brossart, P. et al., Blood 90 (1997)
Bruckdorfer, T. et al., Curr. Pharm. Biotechnol. 5 (2004)
Card, K. F. et al., Cancer Immunol. Immunother. 53 (2004)
Chanock, S. J. et al., Hum. Immunol. 65 (2004)
Cohen, C. J. et al., J Mol. Recognit. 16 (2003a)
Cohen, C. J. et al., J Immunol. 170 (2003b)
Cohen, S. N. et al., Proc. Natl. Acad. Sci. U.S.A 69 (1972)
Coligan J E et al., (1995)
Colombetti, S. et al., J Immunol. 176 (2006)
Dengjel, J. et al., Clin Cancer Res 12 (2006)
Denkberg, G. et al., J Immunol. 171 (2003)
Falk, K. et al., Nature 351 (1991)
Fong, L. et al., Proc. Natl. Acad. Sci. U.S.A 98 (2001)
Gabrilovich, D. I. et al., Nat. Med 2 (1996)
Gattinoni, L. et al., Nat. Rev. Immunol. 6 (2006)
Gnjatic, S. et al., Proc Natl. Acad. Sci. U.S.A 100 (2003)
Godkin, A. et al., Int. Immunol 9 (1997)
Green M R et al., 4th, (2012)
Greenfield E A, 2nd, (2014)
Hwang, M. L. et al., J Immunol. 179 (2007)
Jung, G. et al., Proc Natl Acad Sci USA 84 (1987)
Kibbe AH, rd, (2000)
Krieg, A. M., Nat. Rev. Drug Discov. 5 (2006)
Liddy, N. et al., Nat. Med. 18 (2012)
Ljunggren, H. G. et al., J Exp. Med 162 (1985)
Longenecker, B. M. et al., Ann N.Y. Acad. Sci. 690 (1993)
Lukas, T. J. et al., Proc. Natl. Acad. Sci. U.S.A 78 (1981)
Lundblad R L, 3rd, (2004)
Meziere, C. et al., J Immunol 159 (1997)
Morgan, R. A. et al., Science 314 (2006)
Mori, M. et al., Transplantation 64 (1997)
Mortara, L. et al., Clin Cancer Res. 12 (2006)
Mueller, L. N. et al., J Proteome. Res. 7 (2008)
Mueller, L. N. et al., Proteomics. 7 (2007)
Mumberg, D. et al., Proc. Natl. Acad. Sci. U.S.A 96 (1999)
Pinheiro J et al., (2015)
Plebanski, M. et al., Eur. J Immunol 25 (1995)
Porta, C. et al., Virology 202 (1994)
Rammensee, H. G. et al., Immunogenetics 50 (1999)
Rini, B. I. et al., Cancer 107 (2006)
Rock, K. L. et al., Science 249 (1990)
Rodenko, B. et al., Nat. Protoc. 1 (2006)
Saiki, R. K. et al., Science 239 (1988)
Seeger, F. H. et al., Immunogenetics 49 (1999)

Sherman F et al., (1986)
Singh-Jasuja, H. et al., Cancer Immunol. Immunother. 53 (2004)
Small, E. J. et al., J Clin Oncol. 24 (2006)
Sturm, M. et al., BMC. Bioinformatics. 9 (2008)
Teufel, R. et al., Cell Mol. Life Sci. 62 (2005)
Tran, E. et al., Science 344 (2014)
Walter, S. et al., J. Immunol. 171 (2003)
Walter, S. et al., Nat Med. 18 (2012)
Willcox, B. E. et al., Protein Sci. 8 (1999)
Zaremba, S. et al., Cancer Res. 57 (1997)
Siegel, R., Ma, J., Zou, Z. & Jemal, C A Cancer *J. Clin.* 64, 9-29 (2014).
Coleman, R. L. et al Nat. Rev. *Clin. Oncol.* 10, 211-224 (2013).
Herzog, T. J. & Pothuri, B. *Nat. Clin. Pract. Oncol.* 3, 604-611 (2006).
Kandalaft, L. E., Powell, D. J., Jr., Singh, N. & Coukos, G. *J. Clin. Oncol.* 29, 925-933 (2011).
Zhang, L., et al. *N. Engl. J. Med.* 348, 203-213 (2003).
Schlienger, K., et al. *Clin. Cancer Res.* 9, 1517-1527 (2003).
Matsuzaki, J., et al. *Proc. Natl. Acad. Sci. U.S.A* 107, 7875-7880 (2010).
Fisk, B., Blevins, T. L., Wharton, J. T. & Ioannides, C. G. *J. Exp. Med.* 181, 2109-2117 (1995).
Curie, T. J., et al. *Nat. Med.* 10, 942-949 (2004).
Vlad, A. M., et al. *Cancer Immunol. Immunother.* 59, 293-301 (2010).
Hodi, F. S., et al. *Proc. Natl. Acad. Sci. U.S.A* 105, 3005-3010 (2008).
Robert, C., et al. *Lancet* 384, 1109-1117 (2014).
Wolchok, J. D., et al. *N. Engl. J. Med.* 369, 122-133 (2013).
Rosenberg, S. A., et al. *Clin. Cancer Res.* 17, 4550-4557 (2011).
Walter, S., et al. *Nat. Med.* 18, 1254-1261 (2012).
Rosenberg, S. A. *Sci. Transl. Med.* 4, 127ps128 (2012).
Tran, E., et al. *Science* 344, 641-645 (2014).
Mantia-Smaldone, G. M., Corr, B. & Chu, C. S. *Hum. Vaccin. Immunother.* 8, 1179-1191 (2012).
Haridas, D., et al. *FASEB J.* 28, 4183-4199 (2014).
Deng, J., et al. *Cancer Metastasis Rev.* 32, 535-551 (2013).
Luo, L. Y., et al. *Cancer Res.* 63, 807-811 (2003).
Uyttenhove, C., et al. *Nat. Med.* 9, 1269-1274 (2003).
Sorensen, R. B., et al. *PLoS One* 4, e6910 (2009).
van den Brule, F., et al. *Lab. Invest.* 83, 377-386 (2003).
Rubinstein, N., et al. *Cancer Cell* 5, 241-251 (2004).
Perez-Diez, A., et al. *Blood* 109, 5346-5354 (2007).
Braumuller, H., et al. *Nature* 494, 361-365 (2013).
Hassan, R. & Ho, M. *Eur. J. Cancer* 44, 46-53 (2008).
Schoggins, J. W., et al. *Nature* 472, 481-485 (2011).
Walter, S., et al. *J. Immunol.* 171, 4974-4978 (2003).
Couzin-Frankel, J. Cancer immunotherapy. *Science* 342, 1432-1433 (2013).
Mellman, I., Coukos, G. & Dranoff, G. *Nature* 480, 480-489 (2011).
Perez, S. A., et al. *Cancer* 116, 2071-2080 (2010).
Matsushita, H., et al. *Nature* 482, 400-404 (2012).
Robbins, P. F., et al. *Nat. Med.* 19, 747-752 (2013).
Gubin, M. M., et al. *Nature* 515, 577-581 (2014).
Andersen, R. S., et al. *Cancer Res.* 72, 1642-1650 (2012).
Lu, Y. C., et al. *Clin. Cancer Res.* 20, 3401-3410 (2014).
Rolland, P., Deen, S., Scott, I., Durrant, L. & Spendlove, I. *Clin. Cancer Res.* 13, 3591-3596 (2007).
Cheng, W. F., et al. *Br. J. Cancer* 100, 1144-1153 (2009).
Berlin, C., et al. *Leukemia* (2014).
Blaustein, A. & Kurman, R. J. *Blaustein's pathology of the female genital tract,* (Springer, New York, N.Y., 2011).
Pham, D. L., et al. *Int. J. Gynecol. Pathol.* 32, 358-367 (2013).

The invention claimed is:

1. A method of treating a patient who has ovarian cancer, comprising administering to said patient a population of activated T cells that kill cancer cells that present a peptide consisting of the amino acid sequence of SEQ ID NO: 548.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the population of activated T cells are administered in the form of a composition.

7. The method of claim 6, wherein the composition further comprises an adjuvant.

8. The method of claim 7, wherein the adjuvant is selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The method of claim 1, wherein the activated T cells are cytotoxic T cells produced by contacting T cells with an antigen presenting cell that expresses the peptide in a complex with an MEW class I molecule on the surface of the antigen presenting cell, for a period of time sufficient to activate said T cell.

10. The method of claim 9, wherein the antigen presenting cell is infected with a recombinant virus expressing the peptide.

11. The method of claim 8, wherein the adjuvant is IL-2.

12. The method of claim 8, wherein the adjuvant is IL-7.

13. The method of claim 8, wherein the adjuvant is IL-15.

14. The method of claim 8, wherein the adjuvant is IL-21.

15. A method of eliciting an immune response in a patient who has ovarian cancer, comprising administering to said patient a population of activated T cells that kill cancer cells that present a peptide consisting of the amino acid sequence of SEQ ID NO: 548.

16. The method of claim 15, wherein the activated T cells are cytotoxic T cells produced by contacting T cells with an antigen presenting cell that expresses the peptide in a complex with an MHC class I molecule on the surface of the antigen presenting cell, for a period of time sufficient to activate said T cell.

17. The method of claim 15, wherein the activated T cells are expanded in vitro.

18. The method of claim 15, wherein the population of activated T cells are administered in the form of a composition.

19. The method of claim 18, wherein the composition further comprises an adjuvant.

20. The method of claim 19, wherein the adjuvant is selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

\* \* \* \* \*